United States Patent
Fang et al.

(10) Patent No.: US 11,352,358 B2
(45) Date of Patent: Jun. 7, 2022

(54) FXR AGONIST

(71) Applicant: XUANZHU BIOPHARMACEUTICAL CO., LTD., Shijiazhuang (CN)

(72) Inventors: Wenkui Ken Fang, Shandong (CN); Bo Chen, Shandong (CN); Tingzhong Wang, Shandong (CN); Jing Cheng, Shandong (CN)

(73) Assignee: XUANZHU BIOPHARMACEUTICAL CO., LTD., Shijiazhuang (CN)

( * ) Notice: Subject to any disclaimer, the term of this patent is extended or adjusted under 35 U.S.C. 154(b) by 44 days.

(21) Appl. No.: 16/628,169

(22) PCT Filed: Jul. 6, 2018

(86) PCT No.: PCT/CN2018/094813
§ 371 (c)(1),
(2) Date: Jan. 2, 2020

(87) PCT Pub. No.: WO2019/007418
PCT Pub. Date: Jan. 10, 2019

(65) Prior Publication Data
US 2021/0024522 A1    Jan. 28, 2021

(30) Foreign Application Priority Data
Jul. 6, 2017 (CN) .................. 201710547157.X

(51) Int. Cl.
*C07D 417/14* (2006.01)
*A61K 31/428* (2006.01)
*C07D 471/08* (2006.01)

(52) U.S. Cl.
CPC .................. *C07D 471/08* (2013.01)

(58) Field of Classification Search
CPC .. C07D 417/14; C07D 413/14; A61K 31/428; A61K 31/422; A61K 31/439; A61P 3/00; A61P 9/00; A61P 35/00; A61P 1/16
USPC ......... 546/112; 548/152, 162, 215; 514/299, 514/367, 374
See application file for complete search history.

(56) References Cited

U.S. PATENT DOCUMENTS

| | | |
|---|---|---|
| 9,751,874 B2 | 9/2017 | Gege et al. |
| 2013/0331349 A1 | 12/2013 | Tully et al. |
| 2015/0366856 A1 | 12/2015 | Tully et al. |

FOREIGN PATENT DOCUMENTS

| | | |
|---|---|---|
| CN | 103443099 A | 12/2013 |
| WO | 00/37077 A1 | 6/2000 |
| WO | 2011020615 A1 | 2/2011 |
| WO | 2012087519 A1 | 6/2012 |
| WO | 2012087520 A1 | 6/2012 |
| WO | 2016096115 A1 | 6/2016 |
| WO | 2018039386 A1 | 3/2018 |

OTHER PUBLICATIONS

International Search Report and Written Opinion issued in Application No. PCT.CN2018/094813 dated Aug. 31, 2018, 10 pages (with English Translation).
Office Action for related European Patent Application No. 18829134.8-1110/3650449, dated Mar. 4, 2021, 8 pages.

*Primary Examiner* — Charanjit Aulakh
(74) *Attorney, Agent, or Firm* — Ditthavong, Steiner & Mlotkowski

(57) ABSTRACT

The present invention belongs to the technical field of pharmaceuticals, and particularly relates to a compound of formula (I), a pharmaceutically acceptable salt thereof, an ester thereof or a stereoisomer of the compound, the salt or the ester, wherein $R^1$, $X_1$, $X_2$, M, Ar, ring A, ring B and L are as defined in the specification. The present invention also relates to: a preparation method for the compound, a pharmaceutically acceptable salt thereof, an ester thereof or a stereoisomer of the compound, the salt or the ester; a pharmaceutical composition and pharmaceutical formulation containing the compound, the pharmaceutically acceptable salt, the ester or the stereoisomer of the compound, the salt or the ester; and a use of the compound, the pharmaceutically acceptable salt, the ester or the stereoisomer of the compound, the salt or the ester in the preparation of a medicament for treating and/or preventing FXR-mediated diseases.

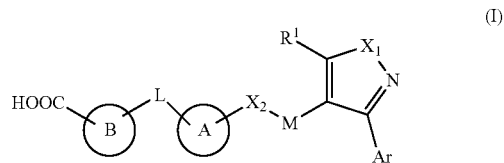

6 Claims, No Drawings

FXR AGONIST

CROSS REFERENCE TO RELATED APPLICATION

This application is a 35 U.S.C. § 371 National Stage of International Application No. PCT/CN2018/094813, filed Jul. 6, 2018, which claims priority from Chinese Application No. 201710547157.X, filed on Jul. 6, 2017, the entire contents and disclosures of each are hereby incorporated by reference.

FIELD OF THE INVENTION

The present invention belongs to the technical field of pharmaceuticals, and particularly relates to an FXR agonist, a preparation method of the FXR agonist, a pharmaceutical formulation containing the FXR agonist, and a use of the FXR agonist.

BACKGROUND OF THE INVENTION

The farnesoid X receptor (FXR) is a member of the nuclear receptor family of ligand-activated transcription factors, and has a typical nuclear receptor structure, namely, a highly conserved amino-terminal DNA-binding domain (DBD), a carboxyl-terminal ligand-binding domain (LBD), an amino-terminal ligand-independent transcriptional activation function domain (AF1), a carboxyl-terminal ligand-dependent transcriptional activation function domain (AF2), and a hinge region. The FXR and a retinoid X receptor (RXR) can form a heterodimer. After a ligand binds to the LBD region of the FXR, the conformation of the FXR can be changed, and the DNA-binding domain of the FXR binds to the FXR response element (JR-1) of a target gene promoter to release co-repressors (such as NCOR) and recruit co-activators, thereby playing the role of transcriptional regulation.

The FXR is expressed in various tissues and organs including adipose tissue, liver, gastrointestinal tract and kidney, wherein the liver has the most abundant FXR expression. The signal pathway of the FXR can regulate the expression of multiple downstream genes, such as BSEP, SHP, CYP7A1, FGFR4, OSTα/β, SREBP-1C, so as to regulate a variety of metabolic pathways, such as the metabolism of triglyceride, cholesterol, blood sugar and cholic acid for energy stability metabolism, and therefore the FXR has the function of treating cancers, nonalcoholic fatty liver diseases (NAFLD), metabolic disorders, inflammations and other diseases. As a main regulator for the cholic acid homeostasis, the FXR can regulate the metabolism of the cholic acid by inhibiting its synthesis, binding and transport.

Some natural cholic acid compounds, such as chenodeoxycholic acid (CDCA), deoxycholic acid (DCA), and lithocholic acid (LCA), and taurine and glycine conjugates thereof, can activate FXR. Apart from natural compounds, FXR agonists currently developed in the world can be divided into two major categories. One category is comprised of steroids as represented by the obeticholic acid (OCA) of Intercept which was approved in May 2016 for the treatment of primary cholangetic cirrhosis and nonalcoholic fatty liver disease and is under phase III clinical trials. However, pruritus and other adverse reactions were observed in the clinical studies of steroids. The other category is novel molecular entities, including compounds early developed such as GW4604 (WO2000/037077). While GW4604 has strong agonistic activity, it exhibits photolability and low bioavailability. PX-104 (WO2011020615A1) of Phenex has been transferred to Gilead, and is under Phase II clinical trials.

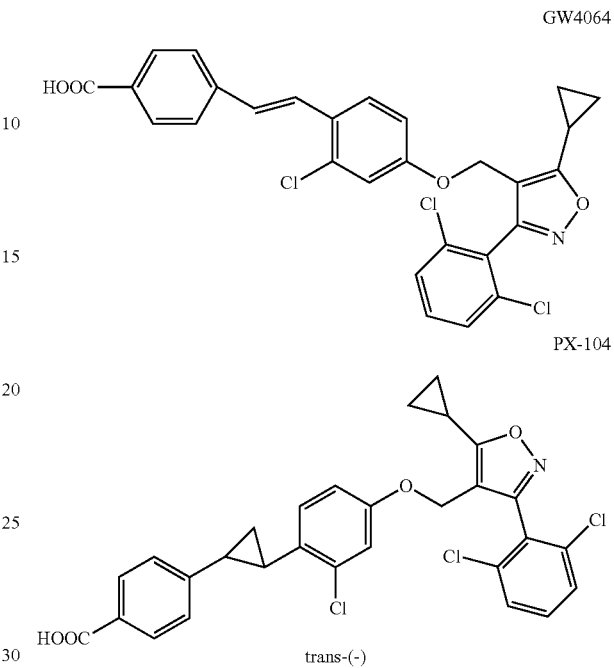

GW4064

PX-104 trans-(-)

In addition, GS-9674 developed by Gilead and LJN-452 developed by Novartis, the structures of which are unknown, are under phase II clinical trials, and their indications comprise primary cholangetic cirrhosis, primary sclerosing cholangitis and nonalcoholic fatty liver disease.

A category of FXR agonists (see patent application WO2012087519A1) was disclosed by Tully et al, and specifically compounds 30-70 were disclosed.

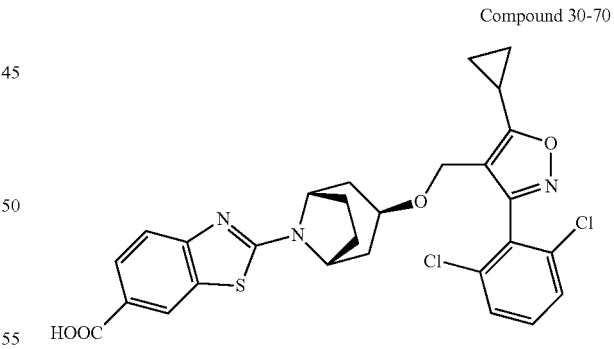

Compound 30-70

At present, it is of great clinical significance to develop novel FXR agonists that have high efficiencies, low toxicities and good stabilities, thus enriching the drug varieties.

SUMMARY OF THE INVENTION

The present invention relates to a compound with a novel molecular entity, which can effectively agitate the FXR, increase the expression levels of BSEP and SHP genes, and meanwhile suppress the expression of CYP7A1 gene efficiently.

In one aspect, the present invention provides a compound as an FXR agonist.

The present invention provides a compound of general formula (I), a pharmaceutically acceptable salt thereof, an ester thereof, or a stereoisomer of the compound, the salt or the ester,

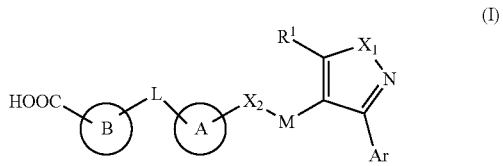

wherein, $R^1$ is selected from a group consisting of halogen, hydroxyl, amino, cyano, $C_{1-6}$ alkyl, halo$C_{1-6}$ alkyl, hydroxy$C_{1-6}$ alkyl, amino$C_{1-6}$ alkyl, $C_{1-6}$ alkoxy, $C_{1-6}$ alkylamino, $C_{1-6}$ alkylcarbonyl, $C_{1-6}$ alkoxy $C_{1-6}$ alkyl, 3-8 membered cycloalkyl, 3-8 membered cycloalkyl $C_{1-6}$ alkyl, 3-8 membered cycloalkyl $C_{1-6}$ alkoxy, 3-8 membered heterocyclyl, 3-8 membered heterocyclyl $C_{1-6}$ alkyl, and 3-8 membered heterocyclyl $C_{1-6}$ alkoxy;

$X_1$ and $X_2$ are each independently selected from a group consisting of N, $NR^2$, O, S and $CR^3R^4$; $R^2$, $R^3$ and $R^4$ are each independently selected from a group consisting of hydrogen, halogen, hydroxyl, amino, cyano, $C_{1-6}$ alkyl, halo$C_{1-6}$ alkyl, $C_{1-6}$ alkoxy and $C_{1-6}$ alkylamino;

M is selected from $C_{1-6}$ alkylene, wherein any one or more carbon atoms in the $C_{1-6}$ alkylene are optionally replaced by a heteroatom or a group, and the heteroatom or the group is selected from a group consisting of N, NH, O, CO, S, SO and $SO_2$;

ring A is selected from 7-membered bridged cyclyl or 7-membered bridged heterocyclyl;

ring B is selected from a group consisting of 6-10 membered aryl, 5-10 membered heteroaryl, 3-14 membered heterocyclyl and 3-8 membered cycloalkyl that are optionally substituted by one or more $Q_1$;

each $Q_1$ is independently selected from a group consisting of halogen, hydroxyl, amino, cyano, $C_{1-6}$ alkyl, halo$C_{1-6}$ alkyl, hydroxy$C_{1-6}$ alkyl, amino$C_{1-6}$ alkyl, $C_{1-6}$ alkoxy, $C_{1-6}$ alkylamino, $C_{1-6}$ alkylcarbonyl, $C_{1-6}$ alkylsulfonyl, $C_{1-6}$ alkylsulfinyl, 3-8 membered cycloalkyl, 3-8 membered cycloalkyl $C_{1-6}$ alkyl, 3-8 membered cycloalkyl $C_{1-6}$ alkoxy, 3-8 membered heterocyclyl, 3-8 membered heterocyclyl $C_{1-6}$ alkyl, and 3-8 membered heterocyclyl $C_{1-6}$ alkoxy;

L is absent or $C_{1-6}$ alkylene, wherein any one or more carbon atoms in the $C_{1-6}$ alkylene are optionally replaced by a heteroatom or a group, and the heteroatom or the group is selected from a group consisting of N, NH, O, CO, S, SO and $SO_2$;

Ar is selected from a group consisting of 6-10 membered aryl, 6-10 membered aryl $C_{1-6}$ alkyl, 6-10 membered aryl $C_{1-6}$ alkoxy, 5-10 membered heteroaryl, 5-10 membered heteroaryl $C_{1-6}$ alkyl, 5-10 membered heteroaryl $C_{1-6}$ alkoxy, 3-8 membered cycloalkyl and 3-8 membered heterocyclyl that are optionally substituted by one or more $Q_2$; and each $Q_2$ is independently selected from a group consisting of halogen, hydroxyl, amino, cyano, $C_{1-6}$ alkyl, halo$C_{1-6}$ alkyl, hydroxy$C_{1-6}$ alkyl, amino$C_{1-6}$ alkyl, $C_{1-6}$ alkoxy, $C_{1-6}$ alkylamino, $C_{1-6}$ alkylcarbonyl, $C_{1-6}$ alkylsulfonyl, $C_{1-6}$ alkylsulfinyl, 3-8 membered cycloalkyl, 3-8 membered cycloalkyl $C_{1-6}$ alkyl, 3-8 membered cycloalkyl $C_{1-6}$ alkoxy, 3-8 membered heterocyclyl, 3-8 membered heterocyclyl $C_{1-6}$ alkyl, and 3-8 membered heterocyclyl $C_{1-6}$ alkoxy.

In some embodiments, $R^1$ is selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkylamino, $C_{1-4}$ alkylcarbonyl, $C_{1-4}$ alkoxy $C_{1-4}$ alkyl, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy.

In some embodiments, $X_1$ and $X_2$ are each independently selected from a group consisting of N, $NR^2$, O, S and $CR^3R^4$; and $R^2$, $R^3$ and $R^4$ are each independently selected from a group consisting of hydrogen, halogen, hydroxyl, amino, cyano, $C_{1-4}$ alkyl, halo$C_{1-4}$ alkyl, $C_{1-4}$ alkoxy and $C_{1-4}$ alkylamino.

In some embodiments, M is $C_{1-4}$ alkylene, any one or more carbon atoms in the $C_{1-4}$ alkylene are optionally replaced by a heteroatom or a group, and the heteroatom or the group is selected from a group consisting of N, NH, O, CO, S, SO and $SO_2$.

In some embodiments, ring A is selected from 7-membered bridged cyclyl or 7-membered nitrogenous bridged heterocyclyl.

In some embodiments, ring B is selected from 8-10 membered fused heteroaryl and 7-14 membered fused heterocyclyl that are optionally substituted by 1 to 2 $Q_1$ and contain 1 to 3 heteroatoms or groups, and the heteroatom or the group is independently selected from a group consisting of N, NH, O, S, SO and $SO_2$.

In some embodiments, each $Q_1$ is independently selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkylamino, $C_{1-4}$ alkylcarbonyl, $C_{1-4}$ alkylsulfonyl, $C_{1-4}$ alkylsulfinyl, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy.

In some embodiments, L is absent or $C_{1-4}$ alkylene, wherein any one or more carbon atoms in the $C_{1-4}$ alkylene are optionally replaced by a heteroatom or a group, and the heteroatom or the group is selected from a group consisting of NH, O, CO, S, SO and $SO_2$.

In some embodiments, Ar is selected from a group consisting of 6-8 membered monocycloaryl, 8-10 membered fused aryl, 6-8 membered monocycloaryl $C_{1-4}$ alkyl, 8-10 membered fused aryl $C_{1-4}$ alkyl, 6-8 membered monocycloaryl $C_{1-4}$ alkoxy, 8-10 membered fused aryl $C_{1-4}$ alkoxy, 5-7 membered monocycloheteroaryl, 8-10 membered fused heteroaryl, 5-7 membered monocycloheteroaryl $C_{1-4}$ alkyl, 8-10 membered fused heteroaryl $C_{1-4}$ alkyl, 5-7 membered monocycloheteroaryl $C_{1-4}$ alkoxy, 8-10 membered fused heteroaryl $C_{1-4}$ alkoxy, 3-8 membered cycloalkyl and 3-8 membered heterocyclyl that are optionally substituted by 1 to 3 $Q_2$.

In some embodiments, each $Q_2$ is independently selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkoxy $C_{1-4}$ alkyl, $C_{1-4}$ alkylamino, $C_{1-4}$ alkylcarbonyl, $C_{1-4}$ alkylsulfonyl, $C_{1-4}$ alkylsulfinyl, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy.

The present invention further provides a compound of general formula (II), a pharmaceutically acceptable salt thereof, an ester thereof, or a stereoisomer of the compound, the salt or the ester,

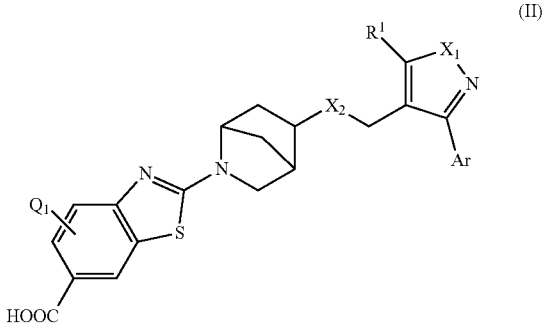

wherein,
$R^1$, $X_1$, $X_2$, $Q_1$ and Ar are as described in any one of the aforementioned embodiments.

In some embodiments, a compound of general formula (I) or (II), a pharmaceutically acceptable salt thereof, an ester thereof, or a stereoisomer of the compound, the salt or the ester, wherein, $R^1$ is selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkylamino, $C_{1-4}$ alkylcarbonyl, $C_{1-4}$ alkoxy$C_{1-4}$ alkyl, 3-4 membered cycloalkyl, 3-4 membered cycloalkyl $C_{1-4}$ alkyl, 3-4 membered cycloalkyl $C_{1-4}$ alkoxy, 3-4 membered monoheterocyclyl, 3-4 membered monoheterocyclyl $C_{1-4}$ alkyl, and 3-4 membered monoheterocyclyl $C_{1-4}$ alkoxy.

In some embodiments, a compound of general formula (I) or (II), a pharmaceutically acceptable salt thereof, an ester thereof, or a stereoisomer of the compound, the salt or the ester, wherein, $R^1$ is selected from a group consisting of halogen, methyl, ethyl, propyl, isopropyl, trifluoromethyl, trifluoroethyl, methoxy, ethoxy, propoxy, isopropoxy, methylamino, ethylamino, methoxymethyl, methoxyethyl, ethoxymethyl, cyclopropyl, cyclopropylmethyl, cyclopropylethyl, cyclopropylmethoxy, cyclobutyl, cyclobutylmethyl, cyclobutylethyl, cyclobutylmethoxy, epoxyethyl, epoxyethylmethyl, azacyclopropyl, azacyclopropylmethyl, oxacyclobutyl and azacyclobutyl.

In some embodiments, a compound of general formula (I) or (II), a pharmaceutically acceptable salt thereof, an ester thereof, or a stereoisomer of the compound, the salt or the ester, wherein, $R^1$ is selected from a group consisting of cyclopropyl, cyclopropylmethyl, cyclopropylethyl, cyclopropylmethoxy, cyclobutyl, cyclobutylmethyl, cyclobutylethyl, cyclobutylmethoxy, epoxyethyl, epoxyethylmethyl, azacyclopropyl, azacyclopropylmethyl, oxacyclobutyl and azacyclobutyl; and preferably, $R^1$ is selected from cyclopropyl or cyclobutyl.

In some embodiments, a compound of general formula (I) or (II), a pharmaceutically acceptable salt thereof, an ester thereof, or a stereoisomer of the compound, the salt or the ester, wherein, $X_1$ and $X_2$ are each independently selected from a group consisting of N, $NR^2$, O and S; $R^2$ is selected from a group consisting of hydrogen, halogen, hydroxyl, amino, methyl, ethyl, propyl, isopropyl and trifluoromethyl;

preferably, $X_1$ and $X_2$ are each independently selected from a group consisting of N, NH, O and S; and more preferably, $X_1$ and $X_2$ both are O.

In some embodiments, a compound of general formula (I), a pharmaceutically acceptable salt thereof, an ester thereof, or a stereoisomer of the compound, the salt or the ester, wherein, M is selected from a group consisting of —$CH_2$—, —$CH_2$—$CH_2$—, —$CH_2$—$CH_2$—$CH_2$—, —$CH_2$—NH—, —$CH_2$—$CH_2$—O— and —$CH_2$—NH—CO—; and preferably, M is selected from a group consisting of —$CH_2$—, —$CH_2$—$CH_2$— and —$CH_2$—$CH_2$—$CH_2$—.

In some embodiments, a compound of general formula (I), a pharmaceutically acceptable salt thereof, an ester thereof, or a stereoisomer of the compound, the salt or the ester, wherein, ring A is selected from 7 membered saturated bridged cyclyl or 7 membered saturated nitrogenous bridged heterocyclyl, and if ring A is saturated nitrogenous bridged heterocyclyl, ring A is preferably attached to L or ring B by a ring nitrogen atom.

In some embodiments, a compound of general formula (I), a pharmaceutically acceptable salt thereof, an ester thereof, or a stereoisomer of the compound, the salt or the ester, wherein, ring A is selected from 7 membered saturated bridged cyclyl or 7 membered saturated bridged heterocyclyl containing 1 nitrogen atom and additional 0 to 1 heteroatom or group, the heteroatom or the group is selected from a group consisting of N, NH, O, S, CO, SO and $SO_2$, and when ring A is 7 membered saturated bridged heterocyclyl containing 1 nitrogen atom and additional 0 to 1 heteroatom or group, ring A is preferably attached to L or ring B by a ring nitrogen atom;

preferably, ring A is selected from the following groups:

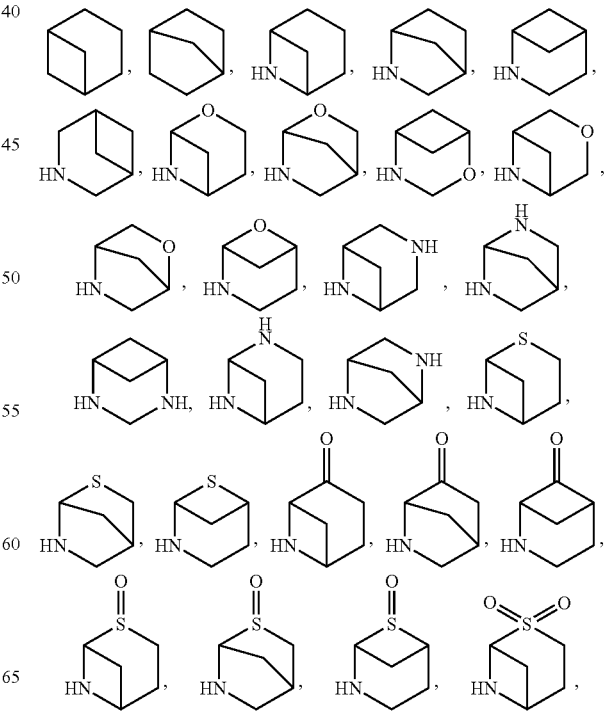

-continued

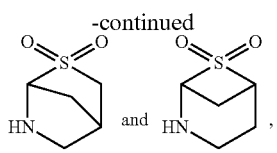

and when ring A is selected from saturated nitrogenous heterocyclyls among these groups, ring A is preferably attached to L or ring B by a ring nitrogen atom;
more preferably, ring A is selected from the following groups:

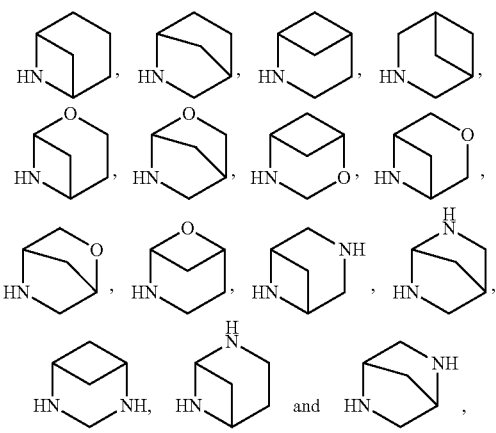

A is preferably attached to L or ring B by a ring nitrogen atom;
more preferably, ring A is selected from the following groups:

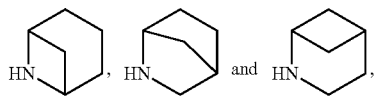

and ring A is preferably attached to L or ring B by a ring nitrogen atom.

In some embodiments, a compound of general formula (I), a pharmaceutically acceptable salt thereof, an ester thereof, or a stereoisomer of the compound, the salt or the ester, wherein,
ring B is 9-10 membered fused heteroaryl that contains 1 to 2 heteroatoms or groups and is optionally substituted by 1 to 2 $Q_1$, and the heteroatom or the group is independently selected from a group consisting of N, NH, O S, SO and $SO_2$; ring B is preferably attached to L or ring A by a ring carbon atom;
each $Q_1$ is independently selected from a group consisting of halogen, hydroxyl, amino, cyano, $C_{1-4}$ alkyl, halo$C_{1-4}$ alkyl, $C_{1-4}$ alkoxy, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy;
L is absent or $C_{1-2}$ alkylene, wherein any one or more carbon atoms in the $C_{1-2}$ alkylene are optionally replaced by a heteroatom or a group, and the heteroatom or the group is selected from a group consisting of NH, O, S and CO.

In some embodiments, a compound of general formula (I), a pharmaceutically acceptable salt thereof, an ester thereof, or a stereoisomer of the compound, the salt or the ester, wherein,
ring B is selected from the following groups optionally substituted by 1 $Q_1$:

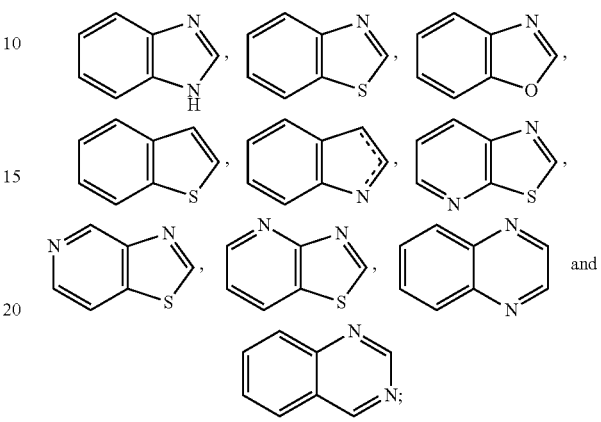

ring B is preferably attached to L or ring A by a ring carbon atom;
preferably, ring B is selected from the following groups optionally substituted by 1 $Q_1$:

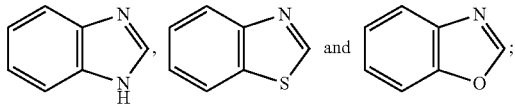

ring B is preferably attached to L or ring A by a ring carbon atom;
$Q_1$ is selected from a group consisting of fluorine, chlorine, bromine, hydroxyl, amino, cyano, methyl, ethyl, propyl, isopropyl, fluoromethyl, difluoromethyl, trifluoromethyl, 1-fluoroethyl, 2-fluoroethyl, 1,1-difluoroethyl, 1,2-difluoroethyl, 2,2-difluoroethyl, 2,2,2-trifluoroethyl, 3,3,3-trifluoropropyl, 1-trifluoromethylethyl, methoxy, ethoxy, propoxy, isopropoxy, cyclopropyl, cyclopropylmethyl, cyclopropylethyl, cyclopropylmethoxy, cyclobutyl, cyclobutylmethyl, cyclobutylethyl, cyclobutylmethoxy, cyclopentyl, cyclohexyl, epoxyethyl, epoxyethylmethyl, azacyclopropyl, azacyclopropylmethyl, oxacyclobutyl, azacyclobutyl, tetrahydrofuryl, pyrrolidyl, imidazolidinyl, pyrazolidinyl, thiazolidinyl, tetrahydropyranyl, tetrahydropyridinyl, piperazinyl andmorpholinyl;
preferably, $Q_1$ is selected from a group consisting of hydrogen, fluorine, chlorine, bromine, methyl, ethyl, propyl, isopropyl, trifluoromethyl, methoxy, ethoxy, propoxy and isopropoxy;
more preferably, $Q_1$ is at the meta-position of the carboxyl in the structure of the general formula; and
L is absent.

In some embodiments, a compound of general formula (II), a pharmaceutically acceptable salt thereof, an ester thereof, or a stereoisomer of the compound, the salt or the ester, wherein,
$Q_1$ is selected from a group consisting of hydrogen, halogen, hydroxyl, amino, cyano, $C_{1-4}$ alkyl, halo$C_{1-4}$ alkyl, $C_{1-4}$ alkoxy, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy;

preferably, $Q_1$ is selected from a group consisting of hydrogen, fluorine, chlorine, bromine, hydroxyl, amino, cyano, methyl, ethyl, propyl, isopropyl, fluoromethyl, difluoromethyl, trifluoromethyl, 1-fluoroethyl, 2-fluoroethyl, 1,1-difluoroethyl, 1,2-difluoroethyl, 2,2-difluoroethyl, 2,2,2-trifluoroethyl, 3,3,3-trifluoropropyl, 1-trifluoromethylethyl, methoxy, ethoxy, propoxy, isopropoxy, cyclopropyl, cyclopropylmethyl, cyclopropylethyl, cyclopropylmethoxy, cyclobutyl, cyclobutylmethyl, cyclobutylethyl, cyclobutylmethoxy, cyclopentyl, cyclohexyl, epoxyethyl, epoxyethylmethyl, azacyclopropyl, azacyclopropylmethyl, oxacyclobutyl, azacyclobutyl, tetrahydrofuryl, pyrrolidyl, imidazolidinyl, pyrazolidinyl, thiazolidinyl, tetrahydropyranyl, tetrahydropyridinyl, piperazinyl andmorpholinyl;

more preferably, $Q_1$ is selected from a group consisting of hydrogen, fluorine, chlorine, bromine, methyl, ethyl, propyl, isopropyl, trifluoromethyl, methoxy, ethoxy, propoxy and isopropoxy; and more preferably, the $Q_1$ is at the meta-position of the carboxyl in the structure of the general formula.

In some embodiments, a compound of general formula (I) or (II), a pharmaceutically acceptable salt thereof, an ester thereof, or a stereoisomer of the compound, the salt or the ester, wherein, Ar is selected from a group consisting of phenyl, phenyl$C_{1-4}$ alkyl, phenyl$C_{1-4}$ alkoxy, 5-6 membered monocycloheteroaryl, 5-6 membered monocycloheteroaryl $C_{1-4}$ alkyl and 5-6 membered monocycloheteroaryl $C_{1-4}$ alkoxy that are optionally substituted by 1 to 2 $Q_2$, and each $Q_2$ is independently selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkoxy $C_{1-4}$ alkyl and $C_{1-4}$ alkylamino;

and preferably, Ar is selected from a group consisting of phenyl, phenylmethyl, phenylethyl, phenylmethoxy, furyl, pyrryl, thienyl, pyrazolyl, imidazolyl, pyridyl and pyrimidinyl that are optionally substituted by 1 to 2 $Q_2$, and each $Q_2$ is independently selected from a group consisting of fluorine, chlorine, bromine, hydroxyl, amino, cyano, methyl, ethyl, propyl, isopropyl, trifluoromethyl, trifluoroethyl, methoxy, ethoxy, propoxy, isopropoxy, methylamino, ethylamino, methoxymethyl, methoxyethyl and ethoxymethyl.

In some embodiments, a compound of general formula (I) or (II), a pharmaceutically acceptable salt thereof, an ester thereof, or a stereoisomer of the compound, the salt or the ester, wherein, Ar is selected from phenyl and 6 membered monocycloheteroaryl that are optionally substituted by 1 to 2 $Q_2$;

preferably, Ar is selected from a group consisting of phenyl, pyridyl and pyrimidinyl that are optionally substituted by 1 to 2 $Q_2$; wherein each $Q_2$ is independently selected from a group consisting of fluorine, chlorine, bromine, hydroxyl, amino, cyano, methyl, ethyl, propyl, isopropyl, trifluoromethyl, trifluoroethyl, methoxy, ethoxy, propoxy, isopropoxy, methylamino, ethylamino, methoxymethyl, methoxyethyl and ethoxymethyl, and preferably, each $Q_2$ is independently selected from a group consisting of fluorine, chlorine, bromine, methyl, ethyl, propyl, isopropyl, trifluoromethyl, methoxy and ethoxy.

In some embodiments, a compound of general formula (II), a pharmaceutically acceptable salt thereof, an ester thereof, or a stereoisomer of the compound, the salt or the ester, wherein, $R^1$ is selected from cyclopropyl or cyclobutyl;

$X_1$ and $X_2$ both are O;

Ar is selected from a group consisting of phenyl, pyridyl and pyrimidinyl that are optionally substituted by 1 to 2 $Q_2$, wherein each $Q_2$ is independently selected from a group consisting of fluorine, chlorine, bromine, methyl, ethyl, propyl, isopropyl, methoxy and ethoxy; and $Q_1$ is selected from a group consisting of hydrogen, fluorine, chlorine, bromine, methyl, ethyl, propyl, isopropyl, trifluoromethyl, methoxy, ethoxy, propoxy and isopropoxy.

In some embodiments, a compound of general formula (II), a pharmaceutically acceptable salt thereof, an ester thereof, or a stereoisomer of the compound, the salt or the ester, wherein, $R_1$ is selected from a group consisting of cyclopropyl, cyclopropylmethyl, cyclopropylethyl, cyclopropylmethoxy, cyclobutyl, cyclobutylmethyl, cyclobutylethyl, cyclobutylmethoxy, epoxyethyl, epoxyethylmethyl, azacyclopropyl, azacyclopropylmethyl, oxacyclobutyl and azacyclobutyl;

$X_1$ and $X_2$ are each independently selected from a group consisting of N, NH, O and S;

$Q_1$ is selected from a group consisting of fluorine, chlorine, bromine, methyl, ethyl, propyl, isopropyl, trifluoromethyl, methoxy, ethoxy, propoxy and isopropoxy;

Ar is selected from a group consisting of phenyl, pyridyl and pyrimidinyl that are optionally substituted by 1 to 2 $Q_2$; and each $Q_2$ is independently selected from a group consisting of methyl, ethyl, propyl, isopropyl, ethoxy and trifluoromethoxy.

In some embodiments, a compound of general formula (II), a pharmaceutically acceptable salt thereof, an ester thereof, or a stereoisomer of the compound, the salt or the ester, wherein, $R^1$ is cyclopropyl;

$X_1$ and $X_2$ both are O;

Ar is phenyl optionally substituted by 1 to 2 $Q_2$; each $Q_2$ is independently selected from a group consisting of chlorine, methoxy and trifluoromethoxy; and $Q_1$ is selected from a group consisting of hydrogen, fluorine, methyl and methoxy.

In some embodiments, a compound of general formula (I), a pharmaceutically acceptable salt thereof, an ester thereof, or a stereoisomer of the compound, the salt or the ester, wherein, $R^1$ is selected from a group consisting of cyclopropyl, cyclopropylmethyl, cyclopropylethyl, cyclopropylmethoxy, cyclobutyl, cyclobutylmethyl, cyclobutylethyl, cyclobutylmethoxy, epoxyethyl, epoxyethylmethyl, azacyclopropyl, azacyclopropylmethyl, oxacyclobutyl and azacyclobutyl;

$X_1$ and $X_2$ are each independently selected from a group consisting of N, NH, O and S;

M is —$CH_2$—;

ring A is

ring B is selected from the following groups:

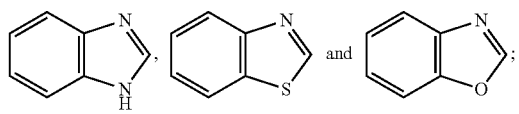

L is absent;
Ar is selected from a group consisting of phenyl, pyridyl and pyrimidinyl that are optionally substituted by 1 to 2 $Q_2$; and each $Q_2$ is independently selected from a group consisting of fluorine, chlorine, bromine, methyl, ethyl, propyl, isopropyl, methoxy, ethoxy, trifluoromethyl and trifluoromethoxy.

In some embodiments, a compound of general formula (I), a pharmaceutically acceptable salt thereof, an ester thereof, or a stereoisomer of the compound, the salt or the ester, wherein, $R^1$ is cyclopropyl;
$X_1$ and $X_2$ both are O;
M is —$CH_2$—;
ring A is

ring B is

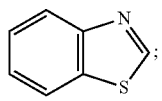

L is absent;
Ar is phenyl optionally substituted by 1 to 2 $Q_2$; and each $Q_2$ is independently selected from chlorine and methoxy.

Any combination can be achieved among the aforementioned embodiments and among the features involved in the embodiments, and all the resultant technical solutions are recited herein, and belong to the technical solutions of the present invention.

Some compounds of the present invention are as follows:

| No. | Structural Formula |
| --- | --- |
| 1 | 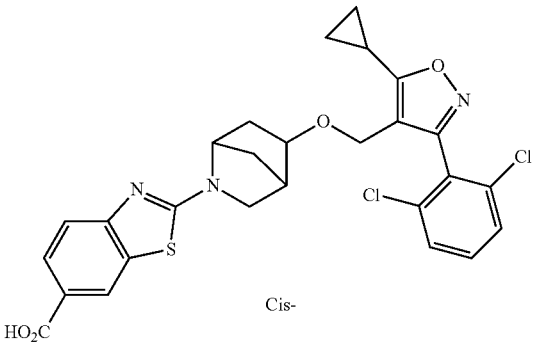 [SMILES: O=C(O)c1ccc2nc(N3CC4CC3CC4OCc3c(-c4c(Cl)cccc4Cl)noc3C3CC3)sc2c1] Cis- |
| 2 | 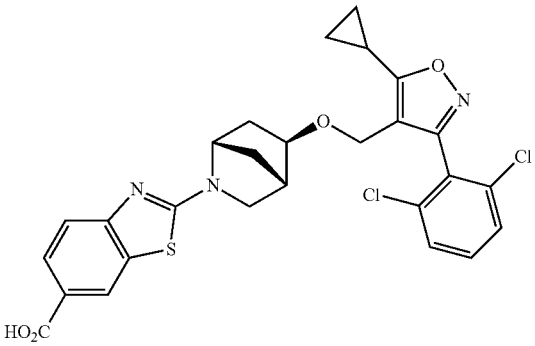 [SMILES: O=C(O)c1ccc2nc(N3C[C@@H]4C[C@H]3C[C@H]4OCc3c(-c4c(Cl)cccc4Cl)noc3C3CC3)sc2c1] Cis- |
| 2-1 |  |
| 2-2 | 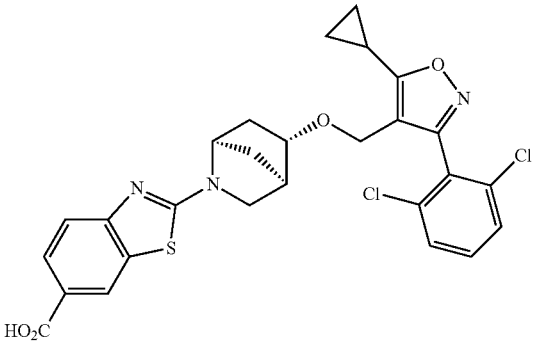 [SMILES: O=C(O)c1ccc2nc(N3C[C@H]4C[C@@H]3C[C@@H]4OCc3c(-c4c(Cl)cccc4Cl)noc3C3CC3)sc2c1] |
| 3 | 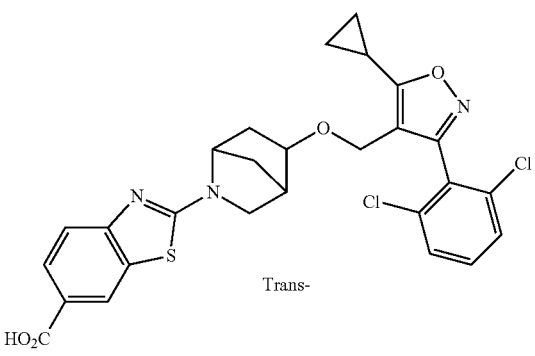 [SMILES: O=C(O)c1ccc2nc(N3CC4CC3CC4OCc3c(-c4c(Cl)cccc4Cl)noc3C3CC3)sc2c1] Trans- |

-continued

| No. | Structural Formula |
|---|---|
| 4 | 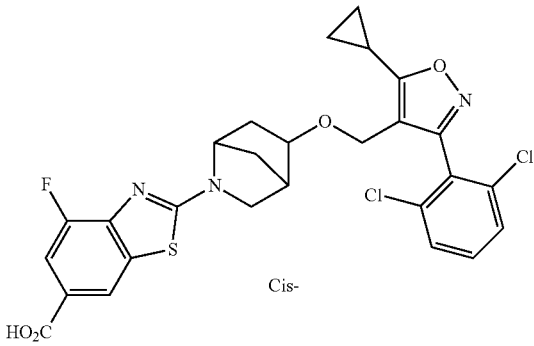 [SMILES: O=C(O)c1cc(F)c2nc(N3CC4CC3CC4OCc3c(-c4c(Cl)cccc4Cl)noc3C3CC3)sc2c1] Cis- |
| 5 | 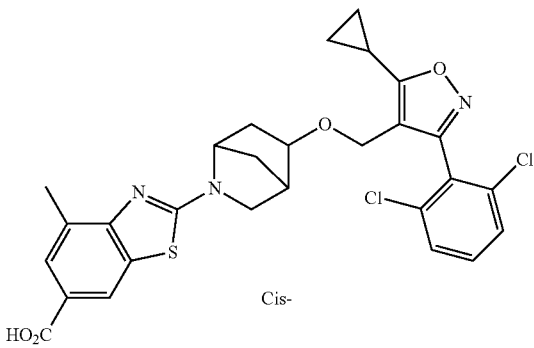 [SMILES: Cc1cc(C(=O)O)cc2sc(N3CC4CC3CC4OCc3c(-c4c(Cl)cccc4Cl)noc3C3CC3)nc12] Cis- |
| 6 | 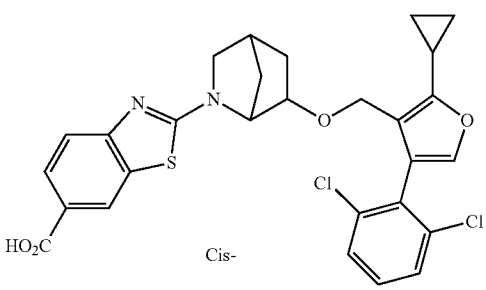 [SMILES: O=C(O)c1ccc2nc(N3CC4CC(OCc5c(-c6c(Cl)cccc6Cl)coc5C5CC5)C3C4)sc2c1] Cis- |
| 7 | 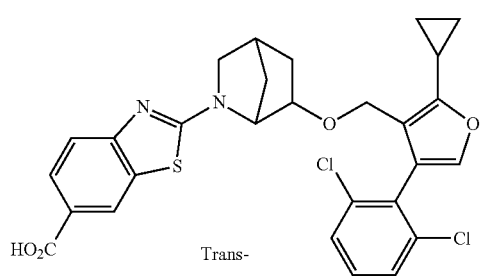 [SMILES: O=C(O)c1ccc2nc(N3CC4CC(OCc5c(-c6c(Cl)cccc6Cl)coc5C5CC5)C3C4)sc2c1] Trans- |

-continued

| No. | Structural Formula |
|---|---|
| 8 | 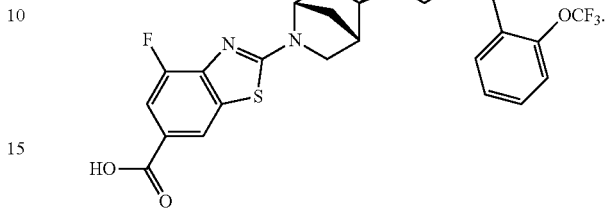 |

In another aspect, the present invention relates to a pharmaceutical composition containing a compound of general formula (I), a pharmaceutically acceptable salt thereof, an ester thereof, or a stereoisomer of the compound, the salt or the ester.

In another aspect, the present invention relates to a pharmaceutical formulation that contains a compound of general formula (I), a pharmaceutically acceptable salt thereof, an ester thereof or a stereoisomer of the compound, the salt or the ester, as well as one or more pharmaceutically acceptable carriers and/or diluents, and the pharmaceutical formulation can be of any pharmaceutically acceptable dosage form. The pharmaceutical formulation can be administered to a patient in need of such treatment via oral, parenteral, rectal or pulmonary administration. For oral administration, the pharmaceutical formulation can be prepared into a conventional solid formulation, such as tablet, capsule, pill, granule, or can be prepared into an oral liquid formulation, such as oral solution, oral suspension, syrup. When the pharmaceutical formulation is prepared into an oral formulation, suitable filler, binder, disintegrant, lubricant and so on can be added. For parenteral administration, the pharmaceutical formulation can be prepared into an injection formulation, including injection, sterile powder for injection and concentrated solution for injection. The injection formulation can be prepared by a conventional method known in the pharmaceutical field, and during the preparation, additives may be not added, or suitable additives can be added according to the properties of the drug. For rectal administration, the pharmaceutical formulation can be prepared into a suppository and so on. For pulmonary administration, the pharmaceutical formulation can be prepared into an inhalant or spray and so on.

In another aspect, the present invention further relates to a use of a compound of general formula (I), a pharmaceutically acceptable salt thereof, an ester thereof or a stereoisomer of the compound, the salt or the ester in the preparation of medicaments for preventing and/or treating FXR-mediated diseases and related diseases in subjects.

The present invention further provides a method for treating and/or preventing FXR-mediated diseases and related diseases in subjects, and the method comprises administering to a subject in need thereof a therapeutically and/or preventively effective amount of the compound, a pharmaceutically acceptable salt thereof, an ester thereof or a stereoisomer of the compound, the salt or the ester in the present invention or a pharmaceutical composition in the present invention.

As used herein, the term "effective amount" refers to an amount sufficient to achieve or at least partially achieve a desired effect. For example, a preventively effective amount for a disease refers to an amount sufficient to prevent, halt or delay the occurrence of a disease; and an therapeutically effective amount for a disease refers to an amount sufficient to cure or at least partially halt a disease and complications thereof in a patient suffering from the disease. Determining such an effective amount is completely within the ability of those skilled in the art. For example, an effective amount for treatment depends on the severity of a disease to be treated, the overall state of the immune system of a patient, the patient profile (such as age, body weight and gender), the administration method of the drug, other therapies simultaneously administered and so on.

In another aspect, the present invention further relates to a use of a compound of general formula (I), a pharmaceutically acceptable salt thereof, an ester thereof, or a stereoisomer of the compound, the salt or the ester, for preventing and/or treating FXR-mediated diseases and related diseases in subjects.

In the present invention, the FXR-mediated diseases and related diseases include but are not limited to:

(1) disorders of lipid or lipoprotein metabolism, such as atherosclerosis, disorder of bile acid metabolism, primary sclerosing cholangitis, cholesterol calculus, fibrosis-related diseases, fatty liver (alcoholic fatty liver disease, non-alcoholic fatty liver disease, etc.), cirrhosis (primary biliary cirrhosis, primary cholangetic cirrhosis, etc.), hepatitis (chronic hepatitis, non-viral hepatitis, alcoholic steatohepatitis, non-alcoholic steatohepatitis, etc.), hepatic failure, cholestasis (benign intrahepatic cholestasis, progressive familial intrahepatic cholestasis, extrahepatic cholestasis, etc.), cholelithiasis, myocardial infarction, stroke, thrombus, etc., acute hepatic failure, cholelithiasis and/or inflammatory bowel diseases.

(2) clinical complications of type I or type II diabetes, including diabetic nephropathy, diabetic neuropathy, diabetic retinopathy and other observed results of clinical overt chronic diabetes.

(3) hyperproliferative diseases, including non-malignant hyperproliferative diseases and malignant hyperproliferative diseases, such as hepatocellular carcinoma, colonic adenoma, polyposis, colonic adenocarcinoma, breast cancer, pancreatic cancer, esophageal carcinoma, and other forms of gastrointestinal and hepatic neoplastic diseases.

In the present invention, subjects or patients can be any animals, and preferably mammals, such as bovines, equids, suidaes, canids, felids, rodents and primates. In particular, subjects are preferably humans.

The present invention also provides a kit that is used to agitate the FXR in cells, increase the BSEP expression and SHP expression in cells and/or suppress the CYP7A1 expression in cells. The kit comprises the compound of the present invention, a pharmaceutically acceptable salt thereof, an ester thereof or a stereoisomer of the compound, the salt or the ester, and optionally includes a manual.

The present invention also provides a use of the compound of the present invention, a pharmaceutically acceptable salt thereof, an ester thereof or a stereoisomer of the compound, the salt or the ester in the preparation of a formulation for agitating the FXR in cells, increasing the BSEP expression and SHP expression in cells and/or suppressing the CYP7A1 expression in cells. In some embodiments, the formulation is used for in-vivo or in-vitro administration. For example, the formulation can be administered into the body of a subject (for example, a mammal, such as bovine, equid, suidae, canid, felid, rodent and primate (such as a human)); or the formulation can be administered to in-vitro cells (for example, cell lines or cells derived from a subject).

The present invention also provides a method for agitating the FXR in cells, increasing the BSEP expression and SHP expression in cells and/or suppressing the CYP7A1 expression in cells, and the method comprises administering to the cells an effective amount of the compound of the present invention, a pharmaceutically acceptable salt thereof, an ester thereof or a stereoisomer of the compound, the salt or the ester. In some embodiments, the method is adopted in vivo, for example, the cells are in-vivo cells of a subject (for example, a mammal, such as bovine, equid, suidae, canid, felid, rodent and primate (such as a human)); or the method is adopted in vitro, for example, the cells are in-vitro cells (for example, cell lines or cells derived from a subject).

The present invention also provides the compound of the present invention, a pharmaceutically acceptable salt thereof, an ester thereof or a stereoisomer of the compound, the salt or the ester, used for agitating the FXR in cells, increasing the BSEP expression and SHP expression in cells and/or suppressing the CYP7A1 expression in cells.

In some embodiments, the cells are cells derived from the liver (for example, liver cells derived from a subject). In some embodiments, the cells are liver cancer cells or hepatocytes. In some embodiments, the cells are HepG2 cells or AML12 cells.

In the specification and claims of the present application, all the compounds are named according to their chemical structural formulas, and if a compound name is not consistent with its chemical structural formula for the same compound, the chemical structural formula or a chemical equation shall prevail.

Definitions of Terms

In the present application, unless otherwise specified, the scientific and technological terms used herein have meanings generally understood by those skilled in the art. However, definitions and explanations for some of the related terms are provided below for better understanding of the present invention. In addition, if the definitions and explanations of the terms provided in the present application are not consistent with the meanings generally understood by those skilled in the art, the definitions and explanations of the terms provided in the present application shall prevail.

"Halo-" described in the present invention refers to being substituted by a "halogen atom", and the "halogen atom" described in the present invention comprises fluorine, chlorine, bromine and iodine atoms.

"$C_{1-6}$ alkyl" described in the present invention refers to a linear or branched alkyl that contains 1 to 6 carbon atoms, including, for example, "$C_{1-5}$ alkyl", "$C_{1-4}$ alkyl", "$C_{1-3}$ alkyl", "$C_{1-2}$ alkyl", "$C_{2-4}$ alkyl", "$C_{2-3}$ alkyl" and "$C_{3-4}$ alkyl", and specific examples include but are not limited to methyl, ethyl, n-propyl, isopropyl, n-butyl, isobutyl, sec-butyl, tert-butyl, n-pentyl, isopentyl, 2-methylbutyl, neopentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc. "$C_{1-4}$ alkyl" described in the present invention refers to a specific example containing 1 to 4 carbon atoms for the $C_{1-6}$ alkyl.

"Halo$C_{1-6}$ alkyl" described in the present invention refers to a group derived from substituting one or more hydrogen atoms in a $C_{1-6}$ alkyl with one or more halogen atoms, and the "halogen atom" and the "$C_{1-6}$ alkyl" are as defined above. "Halo$C_{1-4}$ alkyl" described in the present invention refers to a specific example containing 1 to 4 carbon atoms for the halo$C_{1-6}$ alkyl.

"Hydroxy$C_{1-6}$ alkyl" described in the present invention refers to a group derived from substituting one or more hydrogen atoms in a $C_{1-6}$ alkyl with one or more hydroxyls, and the "$C_{1-6}$ alkyl" is as defined above. "Hydroxy$C_{1-4}$ alkyl" described in the present invention refers to a specific example containing 1 to 4 carbon atoms for the hydroxy$C_{1-6}$ alkyl.

"Amino$C_{1-6}$ alkyl" described in the present invention refers to a group derived from substituting one or more hydrogen atoms in a $C_{1-6}$ alkyl with one or more amino groups, and the "$C_{1-6}$ alkyl" is as defined above. "Amino$C_{1-4}$ alkyl" described in the present invention refers to a specific example containing 1 to 4 carbon atoms for the amino$C_{1-6}$ alkyl.

"$C_{1-6}$ alkoxy, $C_{1-6}$ alkylamino, $C_{1-6}$ alkylcarbonyl, $C_{1-6}$ alkylsulfonyl and $C_{1-6}$ alkylsulfinyl" described in the present invention refer to groups having $C_6$ alkyl-O—, C6 alkyl-NH—, $C_{1-6}$ alkyl-C(O)—, $C_{1-6}$ alkyl-S(O)$_2$— and $C_{1-6}$ alkyl-S(O)— therein, wherein the "$C_{1-6}$ alkyl" is as defined above. "$C_{1-4}$ alkoxy, $C_{1-4}$ alkylamino, $C_{1-4}$ alkylcarbonyl, $C_{1-4}$ alkylsulfonyl and $C_{1-4}$ alkylsulfinyl" described in the present invention refer to specific examples containing 1 to 4 carbon atoms in the alkyl groups for the above examples.

"$C_{1-6}$ alkoxy $C_{1-6}$ alkyl" described in the present invention refers to a group derived from substituting one or more hydrogen atoms in a $C_{1-6}$ alkyl group with one or more $C_{1-6}$ alkoxy groups, and the "$C_{1-6}$ alkyl" is as defined above. "$C_{1-4}$ alkoxy $C_{1-4}$ alkyl" described in the present invention refers to a specific example containing 1 to 4 carbon atoms in each group for the $C_{1-6}$ alkoxy $C_{1-6}$ alkyl.

"$CR^3R^4$" described in the present invention refers to a group formed by substituting two hydrogen atoms in a methylene group respectively with $R^3$ and $R^4$, and the specific connection manner is as

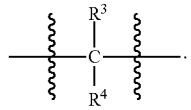

"$C_{1-6}$ alkylene" described in the present invention refers to a group derived from removing two hydrogen atoms on different carbon atoms from a linear alkane group containing 1 to 6 carbon atoms, including "$C_{1-5}$ alkylene", "$C_{1-4}$ alkylene", "$C_{1-3}$ alkylene" and "$C_{1-2}$ alkylene", and specific examples include but are not limited to —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CH$_2$CH$_2$CH$_2$CH$_2$—, etc.

"Any one or more carbon atoms in the $C_{1-6}$ alkylene are optionally replaced by a heteroatom or a group" described in the present invention means that any one or more carbon atoms in the "$C_{1-6}$ alkylene" can be optionally replaced by one or more heteroatoms or groups, that is, the carbon atoms in the $C_{1-6}$ alkylene may not be replaced by any heteroatom or group, one carbon atom in the $C_{1-6}$ alkylene may be replaced by a heteroatom or a group, or any two carbon atoms in the $C_{1-6}$ alkylene may be replaced by two heteroatoms or groups that are the same or different, or any multiple carbon atoms in the $C_{1-6}$ alkylene may be replaced by corresponding multiple heteroatoms or groups that are the same or different; and the heteroatom or the group is selected from a group consisting of N, NH, 0, CO, S, SO and SO$_2$.

"3-8 membered cycloalkyl" described in the present invention refers to a monocyclic saturated alkyl group that contains 3 to 8 carbon atoms, including, for example, "3-6 membered cycloalkyl", "3-5 membered cycloalkyl", "3-4 membered cycloalkyl", "4-5 membered cycloalkyl", "4-6 membered cycloalkyl", "4-7 membered cycloalkyl", "4-8 membered cycloalkyl", etc. Specific examples include but are not limited to cyclopropyl, cyclobutyl, cyclopentyl, cyclohexyl, cycloheptyl, cyclooctyl and the like. "3-6 membered cycloalkyl" refers to a saturated cyclic alkyl containing 3 to 6 carbon atoms. "3-4 membered cycloalkyl" refers to a saturated cyclic alkyl containing 3 to 4 carbon atoms.

"3-14 membered heterocyclyl" described in the present invention refers to a group obtained by removing one hydrogen atom from a monocyclic compound or a fused cyclic compound that is saturated or partially saturated and contains 3 to 14 ring atoms and at least one heteroatom (for example, 1, 2, 3, 4 or 5 heteroatoms). The "fused rings" refers to a group formed by two or more cyclic structures sharing two adjacent atoms with each other. The "3-14 membered heterocyclyl" includes, for example, "3-12 membered heterocyclyl", "3-10 membered heterocyclyl", "3-8 membered heterocyclyl", "3-7 membered heterocyclyl", "3-6 membered monoheterocyclyl", "3-4 membered monoheterocyclyl", "4-7 membered monoheterocyclyl", "4-6 membered monoheterocyclyl", "5-6 membered monoheterocyclyl", "7-10 membered fused heterocyclyl" and "7-14 membered fused heterocyclyl". "3-14 membered partially-saturated heterocyclyl" refers to a cyclic group containing double bonds and heteroatoms. "3-14 membered saturated heterocyclyl" refers to a cyclic group containing heteroatoms and no unsaturated bond. Specific examples include but are not limited to epoxyethyl, azacyclopropyl, diazacyclopropyl, oxacyclobutyl, azacyclobutyl, 1,4-dioxacyclohexyl, 1,3-dioxacyclohexyl, 1,3-dioxacyclopentyl, tetrahydrofuryl, tetrahydrothienyl, pyrrolidyl, imidazolidinyl, pyrazolidinyl, piperazinyl, morpholinyl, benzodihydrofuryl, benzodihydropyranyl, benzo1,4-dioxacyclohexenyl, benzo1,3-dioxacyclohexenyl, benzotetrahydropyridyl, benzodihydrooxazinyl, benzotetrahydropyrazinyl, 1,2,3,4-tetrahydroquinazolinyl, 1,2,3,4-tetrahydrocinnolinyl or tetrahydronaphthyl. "3-6 membered heterocyclyl" refers to a specific example containing 3 to 6 ring atoms for the 3-14 membered heterocyclyl. "3-4 membered monoheterocyclyl" refers to a specific example of a monocyclic heterocyclyl containing 3 to 4 ring atoms for the 3-14 membered heterocyclyl.

"3-8 membered cycloalkyl $C_{1-6}$ alkyl" and "3-8 membered cycloalkyl $C_{1-6}$ alkoxy" described in the present invention refer to groups obtained by substituting hydrogen atoms in a $C_{1-6}$ alkyl group and a $C_{1-6}$ alkoxy group with 3-8 membered cycloalkyl groups, and the "3-8 membered cycloalkyl", "$C_{1-6}$ alkyl" and "$C_{1-6}$ alkoxy" are as defined above.

"3-8 membered heterocyclyl $C_{1-6}$ alkyl" and "3-8 membered heterocyclyl $C_{1-6}$ alkoxy" described in the present invention refer to groups obtained by substituting hydrogen atoms in a $C_{1-6}$ alkyl group and a $C_{1-6}$ alkoxy group with 3-8 membered heterocyclyl groups, and the "3-8 membered heterocyclyl", "$C_{1-6}$ alkyl" and "$C_{1-6}$ alkoxy" are as defined above.

"3-6 membered cycloalkyl $C_{1-4}$ alkyl", "3-4 membered cycloalkyl $C_{1-4}$ alkyl", "3-6 membered monoheterocyclyl $C_{1-4}$ alkyl" and "3-4 membered monoheterocyclyl $C_{1-4}$ alkyl" described in the present invention refer to groups obtained by substituting a hydrogen atom in a $C_{1-4}$ alkyl group with a 3-6 membered cycloalkyl group, a 3-4 membered cycloalkyl group, a 3-6 membered monoheterocyclyl group and a 3-4 membered monoheterocyclyl group respectively, and the "3-6 membered cycloalkyl", "3-4 membered cycloalkyl", "3-6 membered monoheterocyclyl", "3-4 membered monoheterocyclyl" and "$C_{1-4}$ alkyl" are as defined above.

"3-6 membered cycloalkyl $C_{1-4}$ alkoxy", "3-4 membered cycloalkyl $C_{1-4}$ alkoxy", "3-6 membered monoheterocyclyl $C_{1-4}$ alkoxy" and "3-4 membered monoheterocyclyl $C_{1-4}$ alkoxy" described in the present invention refer to groups obtained by substituting a hydrogen atom in a $C_{1-4}$ alkoxy group with a 3-6 membered cycloalkyl group, a 3-4 membered cycloalkyl group, a 3-6 membered monoheterocyclyl group and a 3-4 membered monoheterocyclyl group, and the "3-6 membered cycloalkyl", "3-4 membered cycloalkyl", "3-6 membered monoheterocyclyl", "3-4 membered monoheterocyclyl" and "$C_{1-4}$ alkoxy" are as defined above.

"6-10 membered aryl" described in the present invention refers to an aromatic monocyclic or polycyclic group containing 6 to 10 ring carbon atoms. For example, "6-10 membered aryl" includes "6-8 membered monocycloaryl", "6-7 membered monocycloaryl", "8-10 membered fused aryl", etc. Specific examples include but are not limited to phenyl, cyclooctanetetraenyl, naphthyl, etc. "6-8 membered monocycloaryl" refers to a specific example of a monocyclic group containing 6 to 8 ring carbon atoms for the 6-10 membered aryl. "6-7 membered monocycloaryl" refers to a specific example of a monocyclic group containing 6 to 7 ring carbon atoms for the 6-10 membered aryl. "8-10 membered fused aryl" refers to a specific example of a polycyclic group containing 8 to 10 ring carbon atoms for the 6-10 membered aryl.

"5-10 membered heteroaryl" described in the present invention refers to an aromatic monocyclic or polycyclic group that contains 5 to 10 ring atoms, wherein at least one of the ring atoms is a heteroatom, and the heteroatom is a nitrogen atom, an oxygen atom and/or a sulfur atom. "5-10 membered heteroaryl" includes, for example, "5-7 membered monocycloheteroaryl", "5-6 membered monocycloheteroaryl", "6 membered monoheteroaryl", "7-10 membered fused heteroaryl", "8-10 membered fused heteroaryl" and "9-10 membered fused heteroaryl". Specific examples include but are not limited to furyl, pyrryl, thienyl, pyrazolyl, imidazolyl, thiazolyl, isothiazolyl, thiadiazolyl, oxazolyl, isooxazolyl, oxadiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, benzofuryl, benzoisofuryl, benzothienyl, indolyl, isoindolyl, benzooxazolyl, benzoimidazolyl, indazolyl, benzotriazolyl, quinolyl, isoquinolyl, etc. "5-6 membered monocycloheteroaryl" refers to a specific example of a monocyclic group containing 5 to 6 ring atoms for the 5-10 membered heteroaryl. "7-10 membered fused heteroaryl", "8-10 membered fused heteroaryl" and "9-10 membered fused heteroaryl" refer to specific examples of polycyclic groups containing 7 to 10 ring atoms, 8 to 10 ring atoms and 9 to 10 ring atoms respectively for the 5-10 membered heteroaryl.

"6-10 membered aryl $C_{1-6}$ alkyl" and "5-10 membered heteroaryl $C_{1-6}$ alkyl" described in the present invention refer to groups obtained by substituting a hydrogen atom in a $C_{1-6}$ alkyl group with a 6-10 membered aryl group and a 5-10 membered heteroaryl group respectively. The "6-10 membered aryl", "5-10 membered heteroaryl" and "$C_{1-6}$ alkyl" are as described above.

"6-10 membered aryl $C_{1-6}$ alkoxy" and "5-10 membered heteroaryl $C_{1-6}$ alkoxy" described in the present invention refer to groups obtained by substituting a hydrogen atom in a $C_{1-6}$ alkoxy group with a 6-10 membered aryl group and a 5-10 membered heteroaryl group respectively. "6-10 membered aryl", "5-10 membered heteroaryl" and "$C_{1-6}$ alkoxy" are as described above.

"6-8 membered monocycloaryl $C_{1-4}$ alkyl", "8-10 membered fused aryl $C_{1-4}$ alkyl", "6 membered monocycloaryl $C_{1-4}$ alkyl", "5-7 membered monocycloheteroaryl $C_{1-4}$ alkyl" and "8-10 membered fused heteroaryl $C_{1-4}$ alkyl" described in the present invention refer to groups obtained by substituting a hydrogen atom in a $C_{1-4}$ alkyl group with a 6-8 membered monocycloaryl group, an 8-10 membered fused aryl group, a 6 membered monocycloaryl group, a 5-7 membered monocycloheteroaryl group and an 8-10 membered fused heteroaryl group respectively. The "6-8 membered monocycloaryl", "8-10 membered fused aryl", "6 membered monocycloaryl", "5-7 membered monocycloheteroaryl", "8-10 membered fused heteroaryl" and "$C_{1-4}$ alkyl" are as defined above.

"6-8 membered monocycloaryl $C_{1-4}$ alkoxy", "8-10 membered fused aryl $C_{1-4}$ alkoxy", "6 membered monocycloaryl $C_{1-4}$ alkoxy", "5-7 membered monocycloheteroaryl $C_{1-4}$ alkoxy" and "8-10 membered fused heteroaryl $C_{1-4}$ alkoxy" described in the present invention refer to groups obtained by substituting a hydrogen atom in a $C_{1-4}$ alkoxy group with a 6-8 membered monocycloaryl group, an 8-10 membered fused aryl group, a 6 membered monocycloaryl group, a 5-7 membered monocycloheteroaryl group and an 8-10 membered fused heteroaryl group respectively. "6-8 membered monocycloaryl", "8-10 membered fused aryl", "6 membered monocycloaryl", "5-7 membered monocycloheteroaryl", "8-10 membered fused heteroaryl" and "$C_{1-4}$ alkoxy" are as defined above.

"L is absent" described in the present invention means that ring A and ring B are directly connected through a chemical bond when L is absent.

A dashed bond in a structural formula or a group of the present invention represents presence or absence, for example, for group

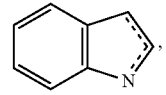

it encompasses

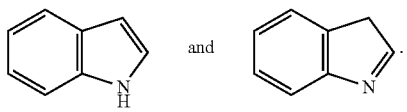 [SMILES: c1ccc2[nH]ccc2c1 ; C1=Nc2ccccc2C1]

"7 membered bridged cyclyl" described in the present invention refers to a saturated or partially-saturated cyclic structure that contains 7 ring carbon atoms and is formed by two or more cyclic structures sharing two non-adjacent ring atoms. For example, "7 membered bridged cyclyl" includes "7 membered saturated bridged cyclyl", and specific examples include but are not limited to

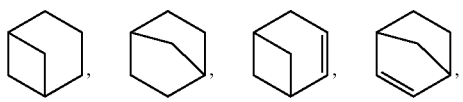

etc. The 7 membered saturated bridged cyclyl refers to a specific example of a saturated bridged cyclyl for the 7 membered bridged cyclyl.

"7 membered bridged heterocyclyl" described in the present invention refers to a saturated or partially-saturated cyclic structure that contains 7 ring atoms (wherein at least one of the ring atoms is a heteroatom or group, such as N, NH, O, S, CO, SO, $SO_2$) and is formed by two or more cyclic structures sharing two non-adjacent ring atoms, and the number of the heteroatoms or groups is preferably 1, 2, 3, 4 or 5, and further preferably 1 or 2. For example, the "7 membered bridged heterocyclyl" includes "7 membered saturated bridged heterocyclyl", "7 membered saturated nitrogenous bridged heterocyclyl" and the like. Specific examples include but are not limited to

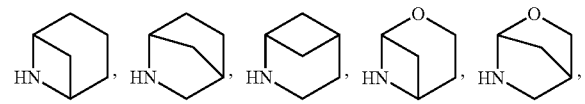

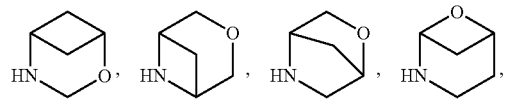

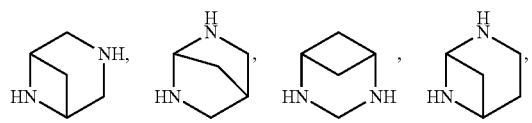

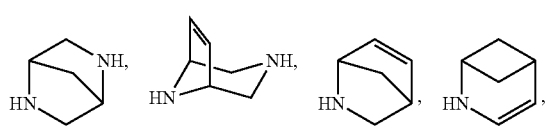

etc. "7 membered saturated nitrogenous bridged heterocyclyl" refers to a specific example of a saturated bridged cyclyl containing at least one nitrogen atom for the 7 membered bridged heterocyclyl.

"Cis-" or "trans-" shown in the structural formula of the compound of the present invention means the positional relationship between the main bridge (a bridge having the minimum carbon atoms) in the bridged ring A and the corresponding substituent in the structure. Taking compound 1 as an example, the compound 1 is of a cis-structure, and has a specific structural formula shown as follows:

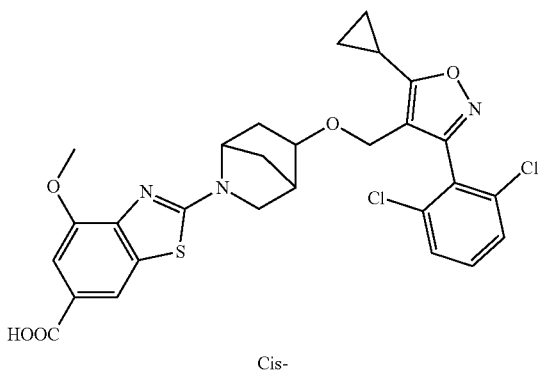 [SMILES: COc1cc(C(=O)O)cc2sc(N3CC4CC3CC4OCc3c(-c4c(Cl)cccc4Cl)noc3C3CC3)nc12]

Cis-wherein the structural formula means the compound 1 is a racemate containing two enantiomers with following structural formulas respectively:

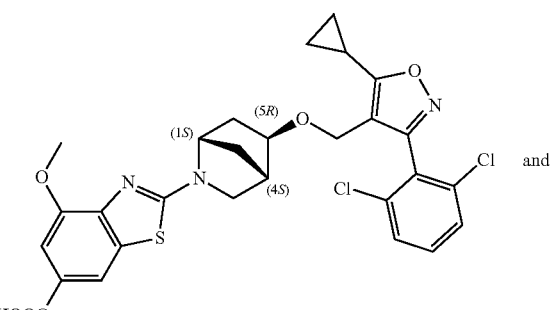

and

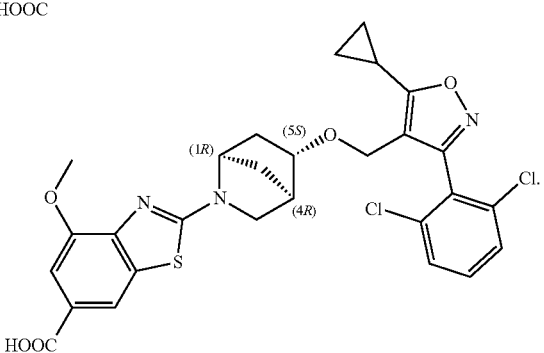

In the structural name of the compound of the present invention, "(1RS, 4RS, 5SR)" represents that the compound is a racemate comprising two enantiomers, wherein the absolute configurations of the two enantiomers are "1R, 4R, 5S" and "1S, 4S, 5R" respectively.

"Optionally" described in the present invention means that it may or may not exist. For example, "ring B is selected from . . . optionally substituted by one or more $Q_1$" described in the present invention includes the case that ring B is not substituted by any $Q_1$, and the case that ring B is substituted by one or more $Q_1$.

"Partially saturated" described in the present invention means that the related group contains at least one double bond or triple bond.

The present invention also provides a preparation method for the compound of formula (I), comprising but not limited to the following process route.

Each acronym is defined as follows:

DMA: N,N-dimethylacetamide; THF: tetrahydrofuran; DCM: dichloromethane; TFA: trifluoroacetic acid; EA: ethyl acetate; PE: petroleum ether; MeOH: methanol.

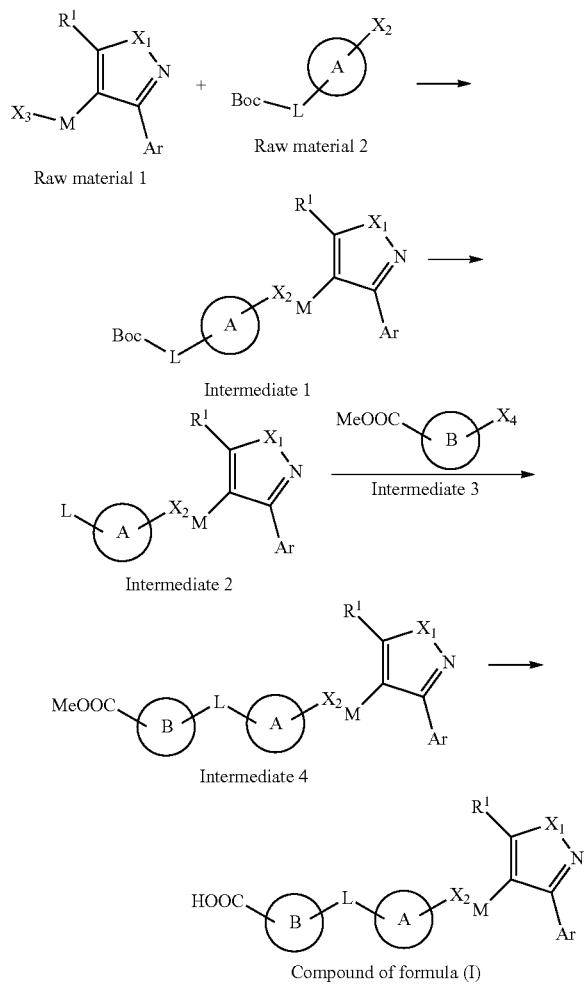

wherein $R^1$, $X_1$, $X_2$, L, M, ring A, ring B and Ar are as described above, and $X_3$ and $X_4$ represent Cl or Br respectively.

The specific exemplary steps are as follows:

(1) Preparation of Intermediate 1

Raw material 2, potassium tert-butoxide, 18-crown-6 and KI are added to an organic solvent, and raw material 1 is then added; the mixture solution reacts at 25-60° C.; and after the reaction is completed, the reaction solution is concentrated and purified by column chromatography to obtain intermediate 1. The organic solvent is preferably tetrahydrofuran.

(2) Preparation of Intermediate 2

Intermediate 1 is slowly added to a solution containing an acidic substance for reaction; after the reaction is completed, the pH of the reaction solution is adjusted to 7 to 8 with an alkaline solution; and the system is spin-dried and concentrated to obtain intermediate 2. The solution containing an acidic substance is preferably a solution of hydrochloric acid in ethanol, a solution of trifluoroacetic acid in dichloromethane, etc., and the alkaline solution is preferably a saturated sodium bicarbonate solution.

(3) Preparation of Intermediate 4

Intermediate 2, intermediate 3 and cesium carbonate are added to an organic solvent for microwave reaction or heating reaction; and after the reaction is completed, the reaction solution is purified by column chromatography to obtain intermediate 4. The organic solvent is preferably DMA.

(4) Preparation of Compound of Formula (I)

Intermediate 4 is added to an organic solvent, and an aqueous solution containing an alkaline substance is then added for heating reaction; after the reaction is completed, the pH of the reaction solution is adjusted to 4 to 6 with an solution of acidic substance; and the reaction solution is spin-dried, and purified by column chromatography to obtain a compound of formula (I). The organic solvent is preferably a mixture solution of methanol and tetrahydrofuran; the alkaline substance is preferably lithium hydroxide, sodium hydroxide, etc.; and the acidic solution is preferably hydrochloric acid.

Raw material 1 and raw material 2 of the present invention can be homemade or purchased.

The "pharmaceutically acceptable salt" of the compound of formula (I) in the present invention refers to: a salt obtained by a acidic functional group in the compound of formula (I) binding a suitable inorganic or organic cation (alkali), such as a salt obtained by the acidic functional group binding an alkali metal or alkaline-earth metal, an ammonium salt, a salt obtained by the acidic functional group binding a nitrogenous organic base; and a salt obtained by a alkaline functional group (such as —$NH_2$) in the compound of formula (I) binding a suitable inorganic or organic anion (acid) including an inorganic acid and organic carboxylic acid.

The "ester" of the compound of formula (I) in the present invention refers to: an ester formed by the esterification reaction between a compound of formula (I) and alcohol when there is a carboxyl group in the compound of formula (I); and an ester formed by the esterification reaction between the compound of formula (I) and an organic acid, an inorganic acid, an organic acid salt or the like when there is a hydroxyl group in the compound of formula (I). In the presence of acid or alkali, the ester can be hydrolyzed to produce a corresponding acid or alcohol. It can serve as a pharmaceutically acceptable ester of the compound of general formula (I), such as alkylacyloxyalkyl ester, alkoxycarbonyloxyalkyl ester, alkoxymethyl ester, alkylacylaminomethyl ester, cycloalkylacyloxyalkyl ester and cycloalkoxyacyloxyalkyl ester.

"Stereoisomerism" is divided into conformational isomerism and configurational isomerism, and the configurational isomerism can further be divided into cis-trans isomerism and optical isomerism. The conformational isomerism refers to a phenomenon that atoms or radicals of an organic molecule having a certain configuration are spatially arranged in a different way due to the rotation or distortion of carbon-carbon single bonds, and it is common in the structures of alkane and cycloalkane compounds, such as the chair conformation and boat conformation appeared in the cyclohexane structure. A "cis-trans isomer" refers to a cis- or a trans-isomer formed when a compound contains a functional group (such as a C=C double bond, a C≡C triple bond, a C=N double bond, a N=N double bond or an alicyclic ring) that is unable to rotate freely. According to the internationally unified "sequence rule", if two superior groups in the compound are on the same side of a 1 bond or an alicyclic ring, the compound is defined as a cis-isomer, and if two superior groups in the compound are on the different sides of a 1 bond or an alicyclic ring, the compound is defined as a trans-isomer. Specifically in the present invention, when the compound contains bridged cyclyl or bridged heterocyclyl, and the cis-form or trans-form means that the main bridge of the bridged cyclyl or bridged heterocyclyl and the groups attached to $X_2$ are on the same side or different sides of the bridged cyclyl or bridged heterocyclyl. An "optical isomer" means that the compound of the present invention can be a racemate or a racemic mixture, a single enantiomer, a mixture of diastereoisomer or a single diastereoisomer as the compound contains one or more asymmetric centers. As the compound of the present invention contains asymmetric centers and each asymmetric center can result in two optical isomers, the scope of the present invention encompasses all possible optical isomers, mixtures of diastereoisomers, and pure or partially-pure compounds. The compound of the present invention can exist in the form of a tautomer, and has different hydrogen connection points by one or more double-bond shifts. For example, ketone and its enolic form are tautomers of each other, known as keto-enol tautomerism. All tautomers and the mixture thereof are included in the compounds of the present invention. All enantiomers, diastereoisomers, racemates, mesomers, cis-trans isomers, tautomers, geometric isomers and epimers of the compound of general formula (I) or (II) as well as the mixture thereof are included in the scope of the present invention.

The present invention also relates to the following embodiments:

Embodiment 1: a compound of general formula (I), a pharmaceutically acceptable salt thereof, an ester thereof, or a stereoisomer of the compound, the salt or the ester,

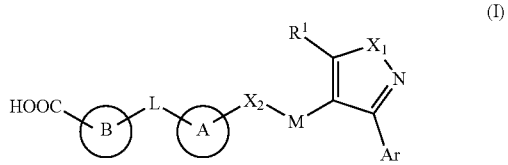

(I)

wherein, $R^1$ is selected from a group consisting of halogen, hydroxyl, amino, cyano, $C_{1-6}$ alkyl, halo$C_{1-6}$ alkyl, hydroxy$C_{1-6}$ alkyl, amino$C_{1-6}$ alkyl, $C_{1-6}$ alkoxy, $C_{1-6}$ alkylamino, $C_{1-6}$ alkylcarbonyl, $C_{1-6}$ alkoxy $C_{1-6}$ alkyl, 3-8 membered cycloalkyl, 3-8 membered cycloalkyl $C_{1-6}$ alkyl, 3-8 membered cycloalkyl $C_{1-6}$ alkoxy, 3-8 membered heterocyclyl, 3-8 membered heterocyclyl $C_{1-6}$ alkyl, and 3-8 membered heterocyclyl $C_{1-6}$ alkoxy;

$X_1$ and $X_2$ are each independently selected from a group consisting of N, $NR^2$, O, S and $CR^3R^4$; $R^2$, $R^3$ and $R^4$ are each independently selected from a group consisting of hydrogen, halogen, hydroxyl, amino, cyano, $C_{1-6}$ alkyl, halo$C_{1-6}$ alkyl, $C_{1-6}$ alkoxy and $C_{1-6}$ alkylamino;

M is $C_{1-6}$ alkylene, wherein any one of carbon atoms in the $C_{1-6}$ alkylene is optionally replaced by a heteroatom or a group, and the heteroatom or the group is selected from a group consisting of N, NH, O, CO, S, SO and $SO_2$;

ring A is selected from 7-membered bridged cyclyl or 7-membered bridged heterocyclyl;

ring B is selected from a group consisting of 6-10 membered aryl, 5-10 membered heteroaryl, 3-14 membered heterocyclyl and 3-8 membered cycloalkyl that are optionally substituted by one or more $Q_1$;

each $Q_1$ is independently selected from a group consisting of halogen, hydroxyl, amino, cyano, $C_{1-6}$ alkyl, halo$C_{1-6}$ alkyl, hydroxy$C_{1-6}$ alkyl, amino$C_{1-6}$ alkyl, $C_{1-6}$ alkoxy, $C_{1-6}$ alkylamino, $C_{1-6}$ alkylcarbonyl, $C_{1-6}$ alkylsulfonyl, $C_{1-6}$ alkylsulfinyl, 3-8 membered cycloalkyl, 3-8 membered cycloalkyl $C_{1-6}$ alkyl, 3-8 membered cycloalkyl $C_{1-6}$ alkoxy, 3-8 membered heterocyclyl, 3-8 membered heterocyclyl $C_{1-6}$ alkyl, and 3-8 membered heterocyclyl $C_{1-6}$ alkoxy;

L is absent or $C_{1-6}$ alkylene, wherein any one of carbon atoms in the $C_{1-6}$ alkylene is optionally replaced by a heteroatom or a group, and the heteroatom or the group is selected from a group consisting of N, NH, O, CO, S, SO and $SO_2$;

Ar is selected from a group consisting of 6-10 membered aryl, 6-10 membered aryl $C_{1-6}$ alkyl, 6-10 membered aryl $C_{1-6}$ alkoxy, 5-10 membered heteroaryl, 5-10 membered heteroaryl $C_{1-6}$ alkyl, 5-10 membered heteroaryl $C_{1-6}$ alkoxy, 3-8 membered cycloalkyl and 3-8 membered heterocyclyl that are optionally substituted by one or more $Q_2$; and each $Q_2$ is independently selected from a group consisting of halogen, hydroxyl, amino, cyano, $C_{1-6}$ alkyl, halo$C_{1-6}$ alkyl, hydroxy$C_{1-6}$ alkyl, amino$C_{1-6}$ alkyl, $C_{1-6}$ alkoxy, $C_{1-6}$ alkoxy $C_{1-6}$ alkyl, $C_{1-6}$ alkylamino, $C_{1-6}$ alkylcarbonyl, $C_{1-6}$ alkylsulfonyl, $C_{1-6}$ alkylsulfinyl, 3-8 membered cycloalkyl, 3-8 membered cycloalkyl $C_{1-6}$ alkyl, 3-8 membered cycloalkyl $C_{1-6}$ alkoxy, 3-8 membered heterocyclyl, 3-8 membered heterocyclyl $C_{1-6}$ alkyl, and 3-8 membered heterocyclyl $C_{1-6}$ alkoxy.

Embodiment 2: the compound, the pharmaceutically acceptable salt thereof, the ester thereof or the stereoisomer of the compound, the salt or the ester of embodiment 1, wherein, $R^1$ is selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkylamino, $C_{1-4}$ alkylcarbonyl, $C_{1-4}$ alkoxy $C_{1-4}$ alkyl, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy;

$X_1$ and $X_2$ are each independently selected from a group consisting of N, $NR^2$, O, S and $CR^3R^4$; $R^2$, $R^3$ and $R^4$ are each independently selected from a group consisting of hydrogen, halogen, hydroxyl, amino, cyano, $C_{1-4}$ alkyl, halo$C_{1-4}$ alkyl, $C_{1-4}$ alkoxy and $C_{1-4}$ alkylamino;

M is $C_{1-4}$ alkylene, wherein any one of carbon atoms in the $C_{1-4}$ alkylene is optionally replaced by a heteroatom or a group, and the heteroatom or the group is selected from a group consisting of N, NH, O, CO, S, SO and $SO_2$;

ring A is selected from 7-membered bridged cyclyl or 7-membered nitrogenous bridged heterocyclyl;

ring B is selected from 8-10 membered fused heteroaryl and 7-14 membered fused heterocyclyl that contain 1 to 3 heteroatoms or groups and are optionally substituted by 1 or 2 $Q_1$, and the heteroatom or the group is independently selected from a group consisting of N, NH, O, S, SO and $SO_2$;

each $Q_1$ is independently selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkylamino, $C_{1-4}$ alkylcarbonyl, $C_{1-4}$ alkylsulfonyl, $C_{1-4}$ alkylsulfinyl, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy;

L is absent or $C_{1-4}$ alkylene, wherein any one of carbon atoms in the $C_{1-4}$ alkylene is optionally replaced by a heteroatom or a group, and the heteroatom or the group is selected from a group consisting of NH, O, CO, S, SO and $SO_2$;

Ar is selected from a group consisting of 6-8 membered monocycloaryl, 8-10 membered fused aryl, 6-8 membered monocycloaryl $C_{1-4}$ alkyl, 8-10 membered fused aryl $C_{1-4}$ alkyl, 6-8 membered monocycloaryl $C_{1-4}$ alkoxy, 8-10 membered fused aryl $C_{1-4}$ alkoxy, 5-7 membered monocycloheteroaryl, 8-10 membered fused heteroaryl, 5-7 membered monocycloheteroaryl $C_{1-4}$ alkyl, 8-10 membered fused heteroaryl $C_{1-4}$ alkyl, 5-7 membered monocycloheteroaryl $C_{1-4}$ alkoxy, 8-10 membered fused heteroaryl $C_{1-4}$ alkoxy, 3-8 membered cycloalkyl and 3-8 membered heterocyclyl that are optionally substituted by 1 to 3 $Q_2$; and each $Q_2$ is independently selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkoxy $C_{1-4}$ alkyl, $C_{1-4}$ alkylamino, $C_{1-4}$ alkylcarbonyl, $C_{1-4}$ alkylsulfonyl, $C_{1-4}$ alkylsulfinyl, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy.

Embodiment 3: the compound, the pharmaceutically acceptable salt thereof, the ester thereof or the stereoisomer of the compound, the salt or the ester of any one of embodiments 1 to 2, wherein, M is selected from a group consisting of —$CH_2$—, —$CH_2$—$CH_2$—, —$CH_2$—$CH_2$—$CH_2$—, —$CH_2$—NH—, —$CH_2$—$CH_2$—O— and —$CH_2$—NH—CO—;

ring A is selected from 7 membered saturated bridged cyclyl or 7 membered saturated nitrogenous bridged heterocyclyl, and when ring A is 7 membered saturated nitrogenous bridged heterocyclyl, preferably, ring A is attached to L or ring B by a ring nitrogen atom.

Embodiment 4: the compound, the pharmaceutically acceptable salt thereof, the ester thereof or the stereoisomer of the compound, the salt or the ester of any one of embodiments 1 to 3, wherein, $R^1$ is selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkylamino, $C_{1-4}$ alkylcarbonyl, $C_{1-4}$ alkoxy $C_{1-4}$ alkyl, 3-4 membered cycloalkyl, 3-4 membered cycloalkyl $C_{1-4}$ alkyl, 3-4 membered cycloalkyl $C_{1-4}$ alkoxy, 3-4 membered monoheterocyclyl, 3-4 membered monoheterocyclyl $C_{1-4}$ alkyl, and 3-4 membered monoheterocyclyl $C_{1-4}$ alkoxy;

ring A is selected from the following groups:

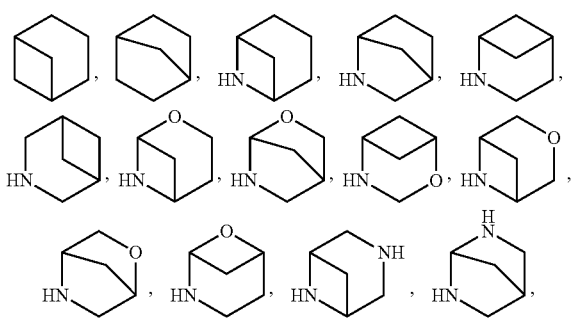

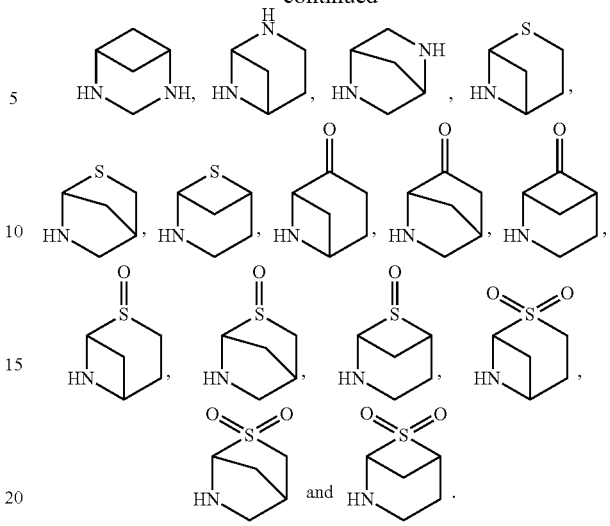

Embodiment 5: the compound, the pharmaceutically acceptable salt thereof, the ester thereof or the stereoisomer of the compound, the salt or the ester of any one of embodiments 1 to 4, wherein, ring B is selected from 9-10 membered fused heteroaryl that contains 1 to 2 heteroatoms or groups and is optionally substituted by 1 to 2 $Q_1$, and the heteroatom or the group is independently selected from a group consisting of N, NH, O, S, SO and $SO_2$; preferably, ring B is attached to L or ring A by a ring carbon atom;

each $Q_1$ is independently selected from a group consisting of halogen, hydroxyl, amino, cyano, $C_{1-4}$ alkyl, halo$C_{1-4}$ alkyl, $C_{1-4}$ alkoxy, 3-6 membered cycloalkyl, 3-6 membered cycloalkyl $C_{1-4}$ alkyl, 3-6 membered cycloalkyl $C_{1-4}$ alkoxy, 3-6 membered monoheterocyclyl, 3-6 membered monoheterocyclyl $C_{1-4}$ alkyl, and 3-6 membered monoheterocyclyl $C_{1-4}$ alkoxy;

L is absent or $C_{1-2}$ alkylene, wherein any one of carbon atoms in the $C_{1-2}$ alkylene is optionally replaced by a heteroatom or a group, and the heteroatom or the group is selected from a group consisting of NH, O, S and CO.

Embodiment 6: the compound, the pharmaceutically acceptable salt thereof, the ester thereof or the stereoisomer of the compound, the salt or the ester of any one of embodiments 1 to 5, wherein, Ar is selected from a group consisting of phenyl, phenyl$C_{1-4}$ alkyl, phenyl$C_{1-4}$ alkoxy, 5-6 membered monocycloheteroaryl, 5-6 membered monocycloheteroaryl $C_{1-4}$ alkyl and 5-6 membered monocycloheteroaryl $C_{1-4}$ alkoxy that are optionally substituted by 1 to 2 $Q_2$; and each $Q_2$ is independently selected from a group consisting of halogen, hydroxyl, amino, cyano, $C_{1-4}$ alkyl, halo$C_{1-4}$ alkyl, hydroxy$C_{1-4}$ alkyl, amino$C_{1-4}$ alkyl, $C_{1-4}$ alkoxy, $C_{1-4}$ alkoxy $C_{1-4}$ alkyl and $C_{1-4}$ alkylamino.

Embodiment 7: the compound, the pharmaceutically acceptable salt thereof, the ester thereof or the stereoisomer of the compound, the salt or the ester of any one of embodiments 1 to 6, wherein, $R^1$ is selected from a group consisting of halogen, methyl, ethyl, propyl, isopropyl, trifluoromethyl, trifluoroethyl, methoxy, ethoxy, propoxy, isopropoxy, methylamino, ethylamino, methoxymethyl, methoxyethyl, ethoxymethyl, cyclopropyl, cyclopropylmethyl, cyclopropylethyl, cyclopropylmethoxy, cyclobutyl, cyclobutylmethyl, cyclobutylethyl, cyclobutylmethoxy, epoxyethyl, epoxyethylmethyl, azacyclopropyl, azacyclopropylmethyl, oxacyclobutyl and azacyclobutyl;

$X_1$ and $X_2$ are each independently selected from a group consisting of N, NH, O and S;

M is selected from —$CH_2$—, —$CH_2$—$CH_2$— or —$CH_2$—$CH_2$—$CH_2$—;

ring A is selected from the following groups:

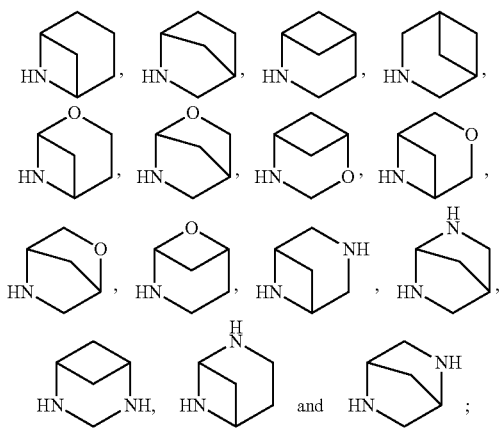

ring B is selected from the following groups optionally substituted by 1 $Q_1$:

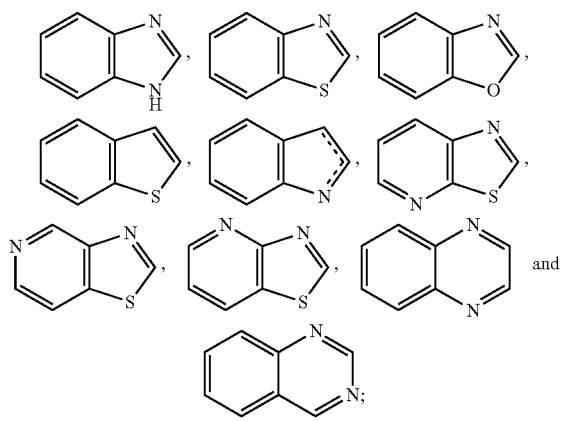

$Q_1$ is selected from a group consisting of fluorine, chlorine, bromine, hydroxyl, amino, cyano, methyl, ethyl, propyl, isopropyl, fluoromethyl, difluoromethyl, trifluoromethyl, 1-fluoroethyl, 2-fluoroethyl, 1,1-difluoroethyl, 1,2-difluoroethyl, 2,2-difluoroethyl, 2,2,2-trifluoroethyl, 3,3,3-trifluoropropyl, 1-trifluoromethylethyl, methoxy, ethoxy, propoxy, isopropoxy, cyclopropyl, cyclopropylmethyl, cyclopropylethyl, cyclopropylmethoxy, cyclobutyl, cyclobutylmethyl, cyclobutylethyl, cyclobutylmethoxy, cyclopentyl, cyclohexyl, epoxyethyl, epoxyethylmethyl, azacyclopropyl, azacyclopropylmethyl, oxacyclobutyl, azacyclobutyl, tetrahydrofuryl, pyrrolidyl, imidazolidinyl, pyrazolidinyl, thiazolidinyl, tetrahydropyranyl, tetrahydropyridinyl, piperazinyl and morpholinyl;

L is absent;

Ar is selected from a group consisting of phenyl, phenylmethyl, phenylethyl, phenylmethoxy, furyl, pyrryl, thienyl, pyrazolyl, imidazolyl, pyridyl and pyrimidinyl that are optionally substituted by 1 to 2 $Q_2$; and each $Q_2$ is independently selected from a group consisting of fluorine, chlorine, bromine, hydroxyl, amino, cyano, methyl, ethyl, propyl, isopropyl, trifluoromethyl, trifluoroethyl, methoxy, ethoxy, propoxy, isopropoxy, methylamino, ethylamino, methoxymethyl, methoxyethyl and ethoxymethyl.

Embodiment 8: the compound, the pharmaceutically acceptable salt thereof, the ester thereof or the stereoisomer of the compound, the salt or the ester of embodiment 7, wherein, $R^1$ is selected from a group consisting of cyclopropyl, cyclopropylmethyl, cyclopropylethyl, cyclopropylmethoxy, cyclobutyl, cyclobutylmethyl, cyclobutylethyl, cyclobutylmethoxy, epoxyethyl, epoxyethylmethyl, azacyclopropyl, azacyclopropylmethyl, oxacyclobutyl and azacyclobutyl;

ring A is selected from a group consisting of

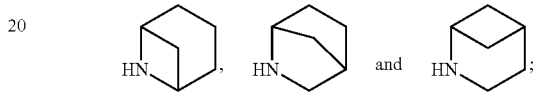

ring B is selected from the following groups optionally substituted by 1 $Q_1$:

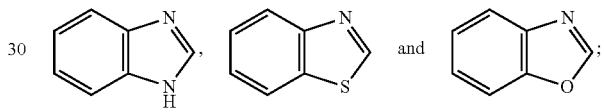

$Q_1$ is selected from a group consisting of fluorine, chlorine, bromine, methyl, ethyl, propyl, isopropyl, trifluoromethyl, methoxy, ethoxy, propoxy and isopropoxy;

Ar is selected from a group consisting of phenyl, pyridyl and pyrimidinyl that are optionally substituted by 1 to 2 $Q_2$; and each $Q_2$ is independently selected from a group consisting of fluorine, chlorine, bromine, methyl, ethyl, propyl, isopropyl, methoxy and ethoxy.

Embodiment 9: the compound, the pharmaceutically acceptable salt thereof, the ester thereof or the stereoisomer of the compound, the salt or the ester of any one of embodiments 1 to 8, having the following structure shown as general formula (II),

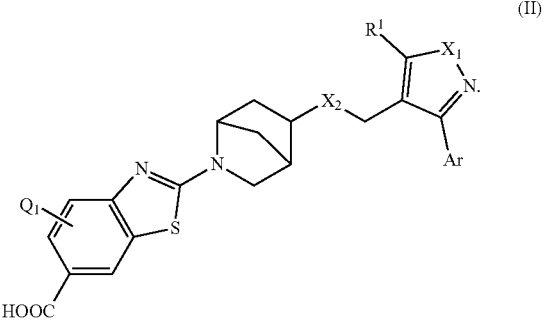

Embodiment 10: the compound, the pharmaceutically acceptable salt thereof, the ester thereof or the stereoisomer of the compound, the salt or the ester of embodiment 1, wherein the compound is selected from:

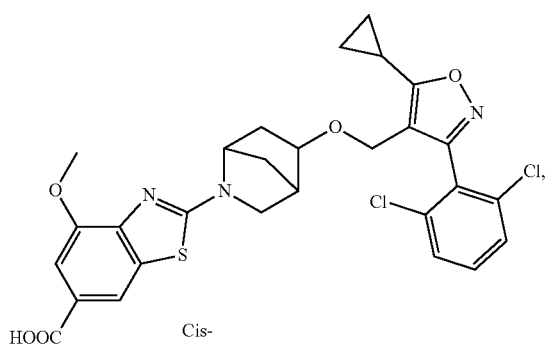
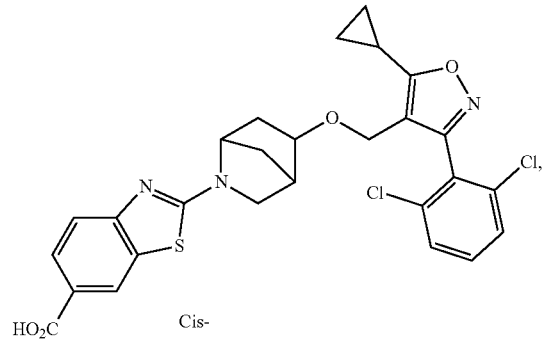
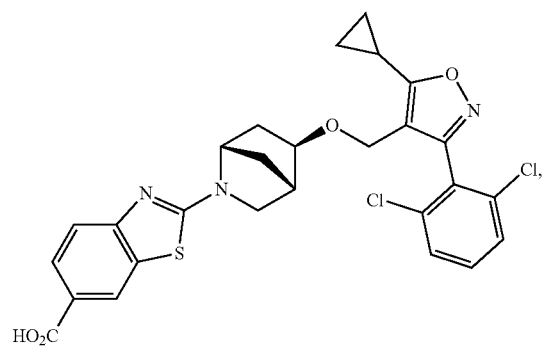
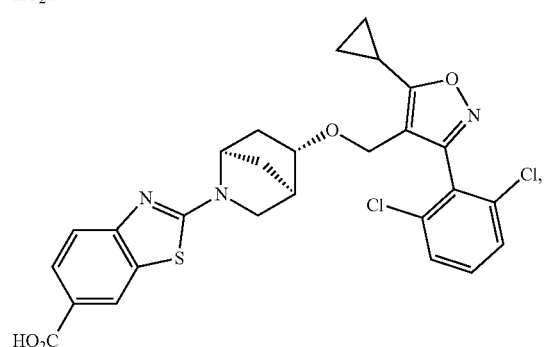
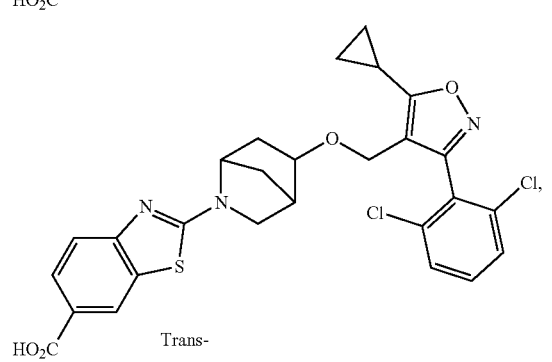
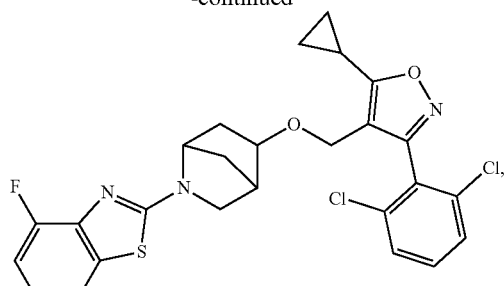
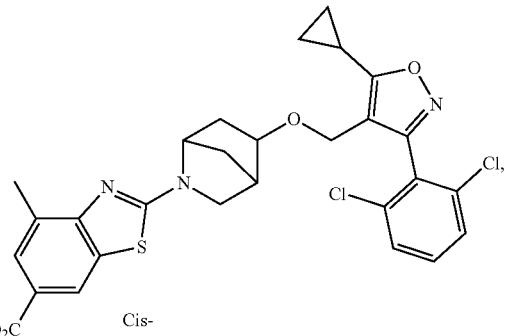
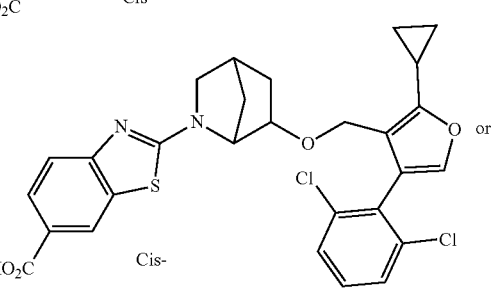
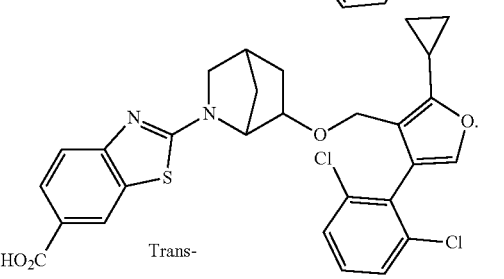

Embodiment 11: a pharmaceutical formulation containing the compound, a pharmaceutically acceptable salt thereof, an ester thereof or a stereoisomer of the compound, the salt or the ester of any one of embodiments 1 to 10, wherein the pharmaceutical formulation contains one or more pharmaceutically acceptable carriers and/or diluents, and can be of any pharmaceutically acceptable dosage form.

Embodiment 12: a use of the compound, a pharmaceutically acceptable salt thereof, an ester thereof or a stereoisomer of the compound, the salt or the ester of any one of embodiments 1-10 in the preparation of medicaments for preventing and/or treating FXR-mediated diseases, wherein the diseases comprise atherosclerosis, disorder of bile acid metabolism, primary sclerosing cholangitis, cholesterol calculus, fibrosis-related diseases, fatty liver, cirrhosis, hepatitis, hepatic failure, cholestasis, cholelithiasis, myocardial infarction, stroke, thrombus, clinical complications of type I or type II diabetes, hyperproliferative diseases and inflammatory bowel diseases.

Embodiment 13: the use of embodiment 12, wherein the diseases are selected from alcoholic fatty liver disease, nonalcoholic fatty liver disease, primary biliary cirrhosis, primary cholangitic cirrhosis, chronic hepatitis, non-viral hepatitis, alcoholic steatohepatitis, nonalcoholic steatohepatitis, benign intrahepatic cholestasis, progressive familial intrahepatic cholestasis, drug-induced cholestasis, cholestasis of pregnancy, gastrointestinal nutrition-related cholestasis, extrahepatic cholestasis, hypercholesteremia, neonatal jaundice, kernicterus, diabetic nephropathy, diabetic neuropathy, diabetic retinopathy, other observed results of clinical overt chronic diabetes, hepatocellular carcinoma, colonic adenoma, polyposis, colonic adenocarcinoma, breast cancer, pancreatic cancer, esophageal carcinoma and other forms of gastrointestinal and hepatic neoplastic diseases.

The compound of the present invention has one or more of the following advantages:

(1) The compound of the present invention, a pharmaceutically acceptable salt thereof, an ester thereof or a stereoisomer of the compound, the salt or the ester has an excellent FXR-agitating activity, and can be safely used to treat an/or prevent nonalcoholic fatty liver disease, primary biliary cirrhosis, disorder of lipid metabolism, diabetic complications, malignant tumors or related diseases.

(2) The compound of the present invention, a pharmaceutically acceptable salt thereof, an ester thereof or a stereoisomer of the compound, the salt or the ester exhibits good metabolic stability, longer effect and high bioavailability.

(3) The compound of the present invention, a pharmaceutically acceptable salt thereof, an ester thereof or a stereoisomer of the compound, the salt or the ester exhibits low toxicity, good drug tolerance and high safety.

EXPERIMENTAL SCHEMES

Exemplary experimental schemes for some compounds of the present invention are provided hereinafter to show the beneficial activity and beneficial technical effect of the compound of the present invention. However, it should be understood that the following experimental schemes are only illustrations for the present invention rather than limit the scope of the present invention. Under the teachings of the specification, those skilled in the art can appropriately modify or change the technical solutions of the present invention without departing from the spirit and scope of the present invention.

Experimental Example 1: Influence of Compounds of the Present Invention on the Relative Expression of BSEP mRNA in HepG2 Cells 1. Test Samples:

compounds of the present invention (for their chemical names and preparation methods, see the preparation example of each compound); compound PX-104 and compound 30-70 (for their structures, see the background of the invention, and for their preparation methods, see patent applications WO2011020615A1 and WO2012087519A1).

PBS represents phosphate buffer solution.

2. Experimental Method:

(1) Cell Plating, Compound Addition and Cell Collection

Cells were digested with pancreatin and collected, and the concentration of the cells was determined; according to the counting result, the cells were resuspended to a density of $7.5 \times 10^5$ cells/mL; 2 mL of the cell suspension was inoculated in each well of a 6-well cell culture plate; and the culture plate was placed in an incubator and cultured under the conditions of 37° C. and 5% $CO_2$ for 24 hrs.

The to-be-tested compounds were diluted to 0.3 mM and 3 mM with DMSO; and 5 µL of each stock solution diluted in the previous step was added to 5 mL of medium individually. The concentrations of the obtained working solutions were 0.3 µM and 3 µM respectively. In the control group, medium was prepared by using equivoluminal DMSO instead of the stock solutions; the cell culture plate was taken out from the incubator; the medium was removed from the cell culture plate, and the working solutions and the control medium were added correspondingly; and the culture plate was then put back into the incubator and cultured under the conditions of 37° C. and 5% $CO_2$ for 24 hrs.

after treatment for 24 hrs, the cell culture plate was taken out, and the medium was removed from the plate; the cells were rinsed three times with pre-cooled (4° C.) PBS; and 200 µL of pancreatin (preheated to 37° C.) was added to each well, and the plate was then gently shaken such that the pancreatin could evenly cover the plate bottom. The culture plate was then placed back into the incubator and incubated until the cells were separated from the plate bottom. 1 mL of medium was added to terminate digestion. The solution was gently pipetted and blown for several times with a pipettor, all the substances in each well were pipetted into a 1.5 mL Rnase-free centrifuge tube and centrifuged at 200×g for 5 mins; supernatants were removed to collect cell samples.

(2) Extraction and Purification of RNA from Cell Samples

Cell lysis: Fresh RNA lysis buffer was prepared (wherein 10 µL of 2-mercaptoethanol was added to 1 mL of lysis buffer); 600 µL of lysis buffer was added to each cell sample; the cells were lysed completely by 1 to 2 mins of vigorous vortexing; the cell lysates were centrifuged at 12,000×g for 5 mins; and the supernatants were transferred to 1.5 mL Rnase-free centrifuge tubes.

Extraction and purification of RNA: An equal amount of 70% ethanol was added to each cell lysate; the centrifuge tubes were then shaken vigorously, and the buffer was mixed sufficiently, so that the particulate precipitates that might be formed after the addition of ethanol were dispersed as even as possible; and adsorption columns were put into collecting tubes, and the mixtures were transferred to the adsorption columns. 700 µL was transferred at most each time; and the solutions were centrifuged at 12,000×g under room temperature for 15 secs. The solutions in the collecting tubes were discarded, and the adsorption columns were put into the collecting tubes once again; and all the remaining mixtures were then transferred into the adsorption columns. 700 µL of eluent I was added to the adsorption column; and the solutions were centrifuged at 12,000×g under room temperature for 15 secs. The adsorption columns were put into new collecting tubes; 500 µL of eluent II was added to the adsorption column; and the solutions were centrifuged at 12,000×g under room temperature for 15 secs. The solutions in the collecting tubes were discarded, and the adsorption columns were put into the collecting tubes once again; 500 L of eluent II was added to the adsorption column; the solutions were centrifuged at 12,000×g under room temperature for 1 to 2 mins, and the adsorption columns were put into RNA collecting tubes; 50 µL of RNase-free water was added to the center of the adsorption column, and the resulted solution was incubated at room temperature for 1 min; and RNA was eluted into the collecting tubes by centrifuging at 14,000×g under room temperature for 2 mins.

The concentration and weight of the extracted RNA were measured. The RNA was stored at −80° C.

(3) Reverse Transcription of RNA into cDNA

The RNA extracted in the second step was incubated at 70° C. for 5 mins, so that the RNA was denatured. The treated sample was put onto ice;

The RNA sample was diluted to 200 ng/μL with RNAse-free water; and 10 μL of reverse transcription solution was prepared according to the following table, and was mixed with 10 μL of denatured RNA. In the reverse transcription reaction, the total amount of RNA was 2 μg. In the process of the experiment, all the reagents were placed on ice.

| Reagent | Volume (μL) |
| --- | --- |
| 10 × RT Buffer | 2 |
| 25 × dNTP Mix | 0.8 |
| 10 × RT Random Primer | 2 |
| MultiScribe Reverse Transcriptase | 1 |
| Total RNA | 10 |
| H$_2$O | 4.2 |
| Total volume | 20 |

Reverse transcription was performed on a G-Storm GS1 PCR thermal cycler. The process of reverse transcription was set as follows: 25° C., 10 mins→37° C., 120 mins→85° C., 5 mins→4° C., ∞. The reverse transcription product (cDNA) was stored at −20° C.

(4) qPCR Experiment for a Sample

According to the efficiency of qPCR amplification, an appropriate cDNA concentration was selected for the qPCR experiment for a sample. 10 μL of the cDNA sample obtained by reverse transcription in the third step was diluted by 7 times with 60 μL of Rnase-free water.

80 μL of reaction mixture was prepared according to the following table, and 20 μL of the reaction mixture was pipetted to a 96-well PCR reaction plate, wherein there were three replications for the cDNA sample (7 μL 100 ng was added to each reaction well).

| Reagent | Volume (μL) |
| --- | --- |
| 2 × TaqMan ® Universal PCR Master Mix | 10 |
| 20 × GAPDH TaqMan probe/primer | 1 |
| 20 × BSEP Taqman probe/primers (FAM-MGB) | 1 |
| cDNA template | 7 |
| Nuclease free water | 1 |
| Total volume | 20 | qPCR was performed on an ABI7500 real-time quantitative PCR amplifier, and the procedure was set as follows: 50° C., 2 mins→95° C., 10 mins→95° C., 15 secs→60° C., 60 secs, wherein 40 cycles were set between 95° C., 15 secs and 60° C., 60 secs.

(5) Experimental Result and Conclusion:

TABLE 1

Assay result of the relative expression of BSEP mRNA in HepG2 cells treated by compound of the present invention

| Test Sample | PX-104 | Compound 30-70 | Compound 2 | Compound 2-1 |
| --- | --- | --- | --- | --- |
| % 0.3 μM | 60 | 105 | 145 | 166 |
| % 3 μM | 100 | 146 | 179 | 185 |

TABLE 2

Assay result of the relative expression of BSEP mRNA in HepG2 cells treated by compound of the present invention

| Test Sample | PX-104 | Compound 1 | Compound 5 | Compound 4 |
| --- | --- | --- | --- | --- |
| % 0.3 μM | 45 | 121 | 103 | 97 |
| % 3 μM | 100 | 102 | 123 | 96 |

Note: the relative expression data in table 1 and table 2 are shown with the expression under 3 μM of PX-104 as 100%, wherein the relative expression (%) under a concentration of a compound is shown as the ratio of the expression under the concentration of the compound to the expression under 3 μM of PX-104.

It can be known from the statistical results of table 1 and table 2, the compounds of the present invention have a good agitating effect on BSEP mRNA in HepG2 cells. BSEP is a direct downstream gene of the FXR and regulates the discharge of bile acid from the liver. The BSEP is a good index for preliminarily screening the FXR-agitating activities of compounds, and has a great significance for treating the nonalcoholic fatty liver disease.

Experimental Example 2: Experiment for the Liver Microsome Metabolism Stability of Compounds of the Present Invention in Different Species Test samples: the homemade compounds 1, 2, 4 and 5 of the present invention (for their chemical names and preparation methods, see the preparation example for each compound).

Experimental Materials:

a mixed liver microsomes of SD rat and human both purchased from XenoTech, with batch Nos.: 1410271 (SD rat) and 1410013 (human) respectively, wherein the microsomal protein concentrations both were 20 mg mL$^{-1}$;

experimental promoter β-NADPH purchased from Roche (batch No.: 524F0231); and a phosphate buffer solution (pH 7.4) made in the lab.

Preparation of Test Sample Solutions

An appropriate amount of the test sample powder was weighed accurately, and dissolved in an appropriate amount of dimethyl sulfoxide (DMSO) to a concentration of 1 mM; and the solution was then diluted by 20 times with methanol to yield a 50 μM working solution.

Experimental Method:

TABLE 3

Composition of the incubation system for liver microsome metabolism stability experiment

| Materials Required | Initial Concentration | Proportion (%) | Final Concentration |
|---|---|---|---|
| Phosphate buffer solution | 100 mM | 50 | 50 mM |
| Anhydrous magnesium chloride | 20 mM | 5 | 1 mM |
| Liver microsome | 20 mg protein/mL | 2.5 | 0.5 mg protein/mL |
| Water additionally required | — | 30.5 | — |
| Test sample | 50 μM | 2 | 1 μM |
| β-NADPH | 10 mM | 10 | 1 mM |

Operating Steps for the Experiment:

(1) According to the proportions in table 3 "Composition of the incubation system for liver microsome metabolism stability experiment" above, for each compound, 6 mL of PBS (100 mM), 0.6 mL of MgCl$_2$ solution (20 mM) and 3.66 mL of H$_2$O were made into a mixed solution 1 for the incubation system (not containing the microsomes, the test sample and β-NADPH).

(2) Liver microsomes (20 mg protein/mL) were taken from a refrigerator (−80° C.), and were placed on a thermostatic water bath oscillator (37° C.) and pre-incubated for 3 mins.

(3) For each compound, 1.88 mL of the mixed solution 1 for the incubation system was added with 55 μL of microsomes to obtain a mixed solution 2 for the incubation system (not containing the test sample and β-NADPH).

(4) Sample group (containing the microsomes and D-NADPH): 616 μL of mixed solution 2 for the incubation system was added with 14 μL of the test sample working solution (with a concentration of 50 μM), and with 70 μL of R-NADPH working solution (10 mM). The resulted solution was well mixed, and the resulted solution was then duplicated. The time points of sampling were at 0 min, 5th min, 10th min, 20th min, 30th min and 60th min.

(5) Control group (containing the microsomes, and water instead of D-NADPH): 264 μL of mixed solution 2 for the incubation system was added with 6 μL of the test sample working solution (50 μM), and with 30 μL of water. The resulted solution was well mixed, and the resulted solution was then duplicated. The time points of sampling were at 0 min and 60th min.

(6) 50 μL of sample was taken from an incubating sample tube at each predetermined time point, added to a terminating sample tube (containing 300 μL of cold terminator), and vortexed; and the reaction was terminated.

(7) after 10 mins of vortexing, the solution was centrifuged for 5 mins (12,000 rpm).

(8) 100 μL of supernatant was taken and added with 100 μL of water, and the mixture solution was thoroughly vortexed; and the solution was then analyzed by LC-MS/MS.

Data Analysis:

Percentages of residual contents were calculated according to the following formula.

$$\% \text{ residual content} = \frac{\text{Peak area ratio of test sample to internal standard at any time point}}{\text{Peak area ratio of test sample to internal standard at time 0}} \times 100\%$$

Experimental Result:

TABLE 4

In-vitro liver microsome metabolism stabilities of compounds of the present invention

| | Residual content (%) after 60 minutes of incubation | | | | | | |
|---|---|---|---|---|---|---|---|
| Species | Compound 1 | Compound 2 | Compound 4 | Compound 5 | Compound 8 | Compound 2-1 | Compound 30-70 |
| Human liver microsome | 49 | 55 | 54 | 31 | 96 | 69 | 20 |
| Rat liver microsome | 53 | 94 | 69 | 49 | 73 | 77 | — |

Experimental Conclusion:

The compounds of the present invention have a good liver microsome metabolism stability, facilitating the better pharmacological effect in vivo, and have a high clinical trial value and a good druggability.

Experimental Example 3: Influence of Compounds of the Present Invention on the Relative Expressions of BSEP mRNA, SHP mRNA and CYP7A1 mRNA in HepG2 Cells 1. Test Samples:

compounds of the present invention (for their chemical names and preparation methods, see the preparation example for each compound).

HepG2 cell: human liver cancer cell;

BSEP: bile salt export pump;

SHP: small heterodimer partner;

CYP7A1: cholesterol 7-alpha hydroxylase;

Control: compound 1-1B with a structure shown as follows, prepared according to a prior art method (for detailed information, see patent application WO2012087519A1).

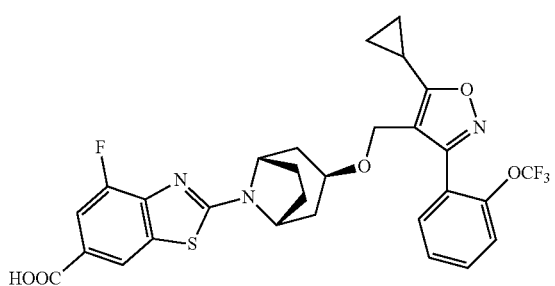

1-1B

2. Experimental Method:

(1) Cell Culture, Compound Treatment and Cell Collection

Cells were digested with pancreatin and collected, and the concentration of the cells was determined; according to the counting result, the cells were resuspended to a density of $7.5 \times 10^5$ cells/mL; 2 mL of the cell suspension was inoculated in each well of a 6-well cell culture plate; and the culture plate was placed in an incubator and cultured under the conditions of 37° C. and 5% $CO_2$ for 24 hrs.

The compounds were diluted to 3000, 1000, 200, 8, 1.6, 0.32, 0.0128, 0.00256 and 0.000512 μM with DMSO. Compound solutions of different concentrations obtained in the previous step were further diluted by 1,000 times with media to obtain working solutions, and a medium containing 0.1% of DMSO was adopted as a control group. The cell culture plate was taken out from the incubator, the medium was removed, and the working solutions and the control medium were added. The culture plate was placed back into the incubator and cultured under the conditions of 37° C. and 5% $CO_2$ for 24 hrs.

after treatment for 24 hrs, the cell culture plate was taken out from the incubator, and the medium was removed from the plate; the cells were rinsed three times with pre-cooled (4° C.) PBS (phosphate buffer solution); and 200 μL of pancreatin (preheated to 37° C.) was added to each well, and the plate was then gently shaken such that the pancreatin could evenly cover the plate bottom. The culture plate was then placed back into the incubator and incubated until the cells were separated from the plate bottom. 1 mL of medium was added to terminate digestion. The solution was gently pipetted and blown for several times with a pipettor, all the substances in each well were pipetted into a 1.5 mL Rnase-free centrifuge tube and centrifuged at 200×g for 5 mins; supernatants were removed to collect cell samples.

(2) Extraction and Purification of Cell RNA Samples

Cell lysis: Fresh RNA lysis buffer was prepared (wherein 10 μL of 2-mercaptoethanol was added to 1 mL of lysis buffer); 600 μL of lysis buffer was added to each cell sample; the cells were lysed completely by 1 to 2 mins of vigorous vortexing; the cell lysates were centrifuged at 12,000×g for 5 mins; and the supernatants were transferred to 1.5 mL Rnase-free centrifuge tubes.

Extraction and purification of RNA: An equal amount of 70% ethanol was added to each cell lysate; the centrifuge tubes were then shaken vigorously, and the buffer was mixed sufficiently, so that the particulate precipitates that might be formed after the addition of ethanol were dispersed as even as possible; and adsorption columns were put into collecting tubes, and the mixtures were transferred to the adsorption columns. 700 μL was transferred at most each time; and the solutions were centrifuged at 12,000×g under room temperature for 15 secs. The solutions in the collecting tubes were discarded, and the adsorption columns were put into the collecting tubes once again; and all the remaining mixtures were then transferred into the adsorption columns. 700 μL of eluent I was added to the adsorption column; and the solutions were centrifuged at 12,000×g under room temperature for 15 secs. The adsorption columns were put into new collecting tubes; 500 μL of eluent II was added to the adsorption column; and the solutions were centrifuged at 12,000×g under room temperature for 15 secs. The solutions in the collecting tubes were discarded, and the adsorption columns were put into the collecting tubes once again; 500 L of eluent II was added to the adsorption column; the solutions were centrifuged at 12,000×g under room temperature for 1 to 2 mins, and the adsorption columns were put into RNA collecting tubes; 50 μL of RNase-free water was added to the center of the adsorption column, and the resulted solution was incubated at room temperature for 1 min; and RNA was eluted into the collecting tubes by centrifuging at 14,000×g under room temperature for 2 mins.

The concentration and weight of the extracted RNA were measured. The RNA was stored at −80° C.

(3) Reverse Transcription of RNA into cDNA

The RNA extracted in the last step was incubated at 70° C. for 5 mins, so that the RNA was denatured. The treated sample was put onto ice; the RNA sample was diluted to 200 ng/μL with RNAse-free water; and 10 μL of reverse transcription solution was prepared according to the following table, and was mixed with 10 μL of denatured RNA. In the reverse transcription reaction, the total amount of RNA was 2 μg. In the process of the experiment, all the reagents were placed on ice.

| Reagent | Volume (μL) |
| --- | --- |
| 10 × RT Buffer | 2 |
| 25 × dNTP Mix | 0.8 |
| 10 × RT Random Primer | 2 |
| MultiScribe Reverse Transcriptase | 1 |
| Total RNA | 10 |
| $H_2O$ | 4.2 |
| Total volume | 20 |

Reverse transcription was performed on a G-Storm GS1 PCR thermal cycler. The process of reverse transcription was set as follows: 25° C., 10 mins→37° C., 120 mins→85° C., 5 mins→4° C., ∞. The reverse transcription product (cDNA) was stored at −20° C.

(4) qPCR Experiment for a Sample

According to the efficiency of qPCR amplification, an appropriate cDNA concentration was selected for the qPCR experiment for a sample. 10 μL of the cDNA sample obtained by reverse transcription in the third step was diluted by 7 times with 60 μL of Rnase-free water.

80 μL of reaction mixture was prepared according to the following table, and 20 μL of the reaction mixture was pipetted to a 96-well PCR reaction plate, wherein there were three replications for the cDNA sample (7 μL 100 ng was added to each reaction well).

| Reagent | Volume (μL) |
| --- | --- |
| 2 × TaqMan ® Universal PCR Master Mix | 10 |
| 20 × GAPDH TaqMan probe/primer | 1 |

| Reagent | Volume (μL) |
|---|---|
| 20 × BSEP/SHP/CYP7A1 Taqman probe/primers (FAM-MGB) | 1 |
| cDNA template | 7 |
| Nuclease free water | 1 |
| Total volume | 20 | qPCR was performed on an ABI7500 real-time quantitative PCR amplifier, and the procedure was set as follows: 50° C., 2 mins→95° C., 10 mins→95° C., 15 secs→60° C., 60 secs, wherein 40 cycles were set between 95° C., 15 secs and 60° C., 60 secs.

3. Experimental Result:

|  | Compound 1-1B | Compound 8 |
|---|---|---|
| BSEP-$EC_{50}$ (nM) | 0.75 | 0.35 |
| SHP-$EC_{50}$ (nM) | 0.26 | 0.09 |
| CYP7A1-$IC_{50}$ (nM) | 0.10 | 0.02 |

Note:

$EC_{50}$ refers to median effective concentration, and $IC_{50}$ refers to median inhibitory concentration.

4. Experimental Conclusion:

It can be known from the experimental result that the compounds of the present invention have a good agitating effect on BSEP mRNA and SHP mRNA in the HepG2 cells, and the corresponding $EC_{50}$ values are significantly smaller than that of the control compound 1-1B; and the compounds of the present invention have a good suppressing effect on CYP7A1 mRNA, and the corresponding $IC_{50}$ values are significantly smaller than that of the control compound 1-1B. As the BSEP and SHP are the direct downstream genes of the FXR, their expression-agitating effects directly reflect the FXR-agitating activity; and as CYP7A1 is the secondary downstream gene of the FXR, its expression-suppressing effect reflects the FXR-agitating activity indirectly. BSEP, SHP and CYP7A1 all are good indexes for preliminarily screening the FXR-agitating activities of compounds.

Experimental Example 4: Influence of Compounds of the Present Invention on the Relative Expression of SHP mRNA in AML12 Cells 1. Test Samples:

compounds of the present invention (for their chemical names and preparation methods, see the preparation example for each compound).

AML12 cells: mouse liver cells.

Control: compound 1-1B with a structure shown as follows, prepared according to a prior art method (for detailed information, see patent application WO2012087519A1).

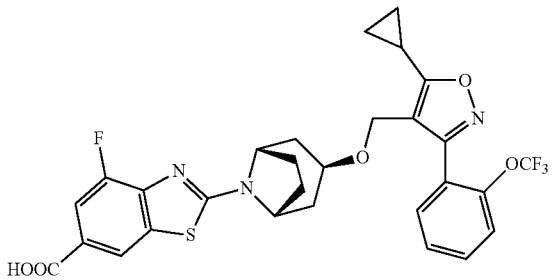

1-1B

2. Experimental Method:

(1) Cell Culture, Compound Treatment and Cell Collection

Cells were digested with pancreatin and collected, and the concentration of the cells was determined; according to the counting result, the cells were resuspended to a density of $7.5 \times 10^4$ cells/mL; 1 mL of the cell suspension was inoculated in each well of a 12-well cell culture plate; and the culture plate was placed in an incubator and cultured under the conditions of 37° C. and 5% $CO_2$ for 24 hrs.

The compound were diluted to 1000, 200, 8, 1.6, 0.32, 0.128, 0.0256 and 0.00512 μM with DMSO. Compound solutions of different concentrations obtained in the previous step were further diluted by 1000 times with media to obtain working solutions, and a medium containing 0.1% of DMSO was adopted as a control group. The cell culture plate was taken out from the incubator, the medium was removed, and the working solutions and the control medium were added. The culture plate was placed back into the incubator and cultured under the conditions of 37° C. and 5% $CO_2$ for 24 hrs.

after treatment for 24 hrs, the cell culture plate was taken out from the incubator, and the medium was removed from the plate; the cells were rinsed three times with pre-cooled (4° C.) PBS (phosphate buffer solution); and 200 μL of pancreatin (preheated to 37° C.) was added to each well, and the plate was then gently shaken such that the pancreatin could evenly cover the plate bottom. The culture plate was then placed back into the incubator and incubated until the cells were separated from the plate bottom. 1 mL of medium was added to terminate digestion. The solution was gently pipetted and blown for several times with a pipettor, all the substances in each well were pipetted into a 1.5 mL Rnase-free centrifuge tube and centrifuged at 200×g for 5 mins; supernatants were removed to collect cell samples.

(2) Extraction and Purification of Cell RNA Samples

Cell lysis: Fresh RNA lysis buffer was prepared (wherein 10 μL of 2-mercaptoethanol was added to 1 mL of lysis buffer); 600 μL of lysis buffer was added to each cell sample; the cells were lysed completely by 1 to 2 mins of vigorous vortexing; the cell lysates were centrifuged at 12,000×g for 5 mins; and the supernatants were transferred to 1.5 mL Rnase-free centrifuge tubes.

Extraction and purification of RNA: An equal amount of 70% ethanol was added to the cell lysate; the centrifuge tubes were then shaken vigorously, the buffer was mixed sufficiently, so that the particulate precipitates that might be formed after the addition of ethanol were dispersed as even as possible; and adsorption columns were put into collecting tubes, and the mixtures were transferred to the adsorption columns. 700 μL was transferred at most each time; and the solutions were centrifuged at 12,000×g under room temperature for 15 secs. The solutions in the collecting tubes were discarded, and the adsorption columns were put into the collecting tubes once again; and all the remaining mixtures were then transferred into the adsorption columns. 700 μL of eluent I was added to the adsorption column; and the solutions were centrifuged at 12,000×g under room temperature for 15 secs. The adsorption columns were put into new collecting tubes; 500 μL of eluent II was added to the adsorption column; and the solutions were centrifuged at 12,000×g under room temperature for 15 secs. The solutions in the collecting tubes were discarded, and the adsorption columns were put into the collecting tubes once again; 500 μL of eluent II was added to the adsorption column; the solutions were centrifuged at 12,000×g under room temperature for 1 to 2 mins, and the adsorption columns were put into RNA collecting tubes; 50 μL of RNase-free water was added to the center of the adsorption column, and the resulted solution was incubated at room temperature for 1 min; and RNA was eluted into the collecting tubes by centrifuging at 14,000×g under room temperature for 2 mins.

The concentration and weight of the extracted RNA were measured. The RNA was stored at −80° C.

(3) Reverse Transcription of RNA into cDNA

The RNA extracted in the last step was incubated at 70° C. for 5 mins, so that the RNA was denatured. The treated sample was put onto ice; the RNA sample was diluted to 100 ng/μL with RNAse-free water; and 10 μL of reverse transcription solution was prepared according to the following table, and was mixed with 10 μL of denatured RNA. In the reverse transcription reaction, the total amount of RNA was 1 μg. In the process of the experiment, all the reagents were placed on ice.

| Reagent | Volume (μL) |
| --- | --- |
| 10 × RT Buffer | 2 |
| 25 × dNTP Mix | 0.8 |
| 10 × RT Random Primer | 2 |
| MultiScribe Reverse Transcriptase | 1 |
| Total RNA | 10 |
| H$_2$O | 4.2 |
| Total volume | 20 |

Reverse transcription was performed on a G-Storm GS1 PCR thermal cycler. The process of reverse transcription was set as follows: 25° C., 10 mins→37° C., 120 mins→85° C., 5 mins→4° C., ∞. The reverse transcription product (cDNA) was stored at −20° C.

(4) qPCR Experiment for a Sample

According to the efficiency of qPCR amplification, an appropriate cDNA concentration was selected for the qPCR experiment for a sample. 20 μL of reaction solution was prepared with the cDNA sample obtained by reverse transcription in the third step according to the following table, and was added to a 96-well PCR reaction plate, with 4 μL of cDNA sample in each reaction well.

| Reagent | Volume (μL) |
| --- | --- |
| 2 × TaqMan ® Universal PCR Master Mix | 10 |
| 20 × GAPDH TaqMan probe/primer | 0.3 |
| 20 × SHP Taqman probe/primers (FAM-MGB) | 1 |
| cDNA template | 4 |
| Nuclease free water | 4.7 |
| Total volume | 20 | qPCR was performed on an ABI7500 real-time quantitative PCR amplifier, and the procedure was set as follows: 50° C., 2 mins→95° C., 10 mins→95° C., 15 secs→60° C., 60 secs, wherein 45 cycles were set between 95° C., 15 secs and 60° C., 60 secs.

3. Experimental Result:

$EC_{50}$ assay results for the influence of compounds of the present invention on the relative expression of SHP mRNA in AML12 cells

| | Compound 1-1B | Compound 2-1 | Compound 8 |
| --- | --- | --- | --- |
| $EC_{50}$ (nM) | 1.51 | 0.76 | 0.89 |

4. Experimental Conclusion:

It can be known from the experimental result that the compounds of the present invention have a good agitating effect on SHP mRNA in the AML12 cells, and the corresponding $EC_{50}$ values are significantly smaller than that of the control compound 1-1B. As SHP is a direct downstream gene of FXR, the expression of SHP mRNA directly reflects the FXR-agitating activity. SHP is a good index for preliminarily screening the FXR-agitating activities of the compounds, and the FXR agonist is expected to become a preference for treating the nonalcoholic fatty liver disease.

Experimental Example 5: Influence of Compounds of the Present Invention on High Fat-Induced NAFLD Mice 1. Experimental Method 1.1 Animal Modeling Build of NAFLD/NASH (non-alcoholic fatty liver disease/nonalcoholic steatohepatitis) mouse models: six-week-old $C_{57}BL/6J$ male mice were fed with high-fat feed, and were weighed each week to record the body weights of the mice; and after high-fat feeding for 8 weeks, the mice were weighed to determine whether the modeling is successful.

1.2 Administration in Groups and Endpoint Treatment

According to the body weight values (40 g was generally considered as a screening critical point), the successfully-modeled mice were divided into a blank control group, a model control group and the compound 2-1 (1 mg/kg) group, wherein the average body weights of all groups were consistent, without any significant difference. The mice were administered once every day (QD) (8 # intragastric syringe) for 3 weeks.

24 hrs after the last administration, blood was sampled from the inner canthus; the sampled blood stood at room temperature for 1 to 2 hrs, and was centrifuged at 4,000 rpm for 15 mins, and the serum was collected; the mice were euthanized thereafter, and a large liver lobe and a small liver lobe were cut off and put into 10% neutral formalin, and the remainings were stored in a refrigerator at −80° C. For the detailed administration method, administration dosage and administration route, see the table below.

Route, dosage and regimen of administration in experiment for influence of compounds of the present invention on high fat-induced NAFLD/NASH mice

| Group | Administered Group | Dosage (mg/kg) | Administered Volume (mL/10 g) | Administration Route |
|---|---|---|---|---|
| 1 | Blank control group | — | 0.1* | p.o. |
| 2 | Model control group | — | 0.1* | p.o. |
| 3 | Compound 2-1 | 1 | 0.1 | p.o. |

*2% HPC + 0.1% polysorbate 80 were used to replace the test compounds.

2 Experimental Evaluation Index
2.1 Experimental Observation Index
1) Body weight: Weighing was performed once every week from the beginning of modeling. Weighing was performed once every week after administration.
2) Analysis of morphological and pathological changes of livers: Liver tissues were separated, collected and photographed. The livers were weighed, and ratios of liver weight/body weight were calculated. The tissue was sliced and stained by H&E (NAFLD score, NAS).
3) Assay of biochemical indexes of livers: TG in the livers was extracted according to the manual of a tissue cell triglyceride assay kit (purchased from Applygen Technologies Inc. E1013), and assayed.
4) Assay of biochemical indexes of serums: LDL in serums was assayed with a full-automatic biochemical analyzer (Hitachi 7180, model: X594).

2.2 Statistical Treatment

Data were represented by mean±S.E.M., and one-way analysis of variance (ANOVA) followed LSD or independent-sample T test were performed on the statistical data with statistical software SPSS 16.0. Statistical differences were tested, and p<0.05 was defined as a significant difference.

3 Experimental Result

Experimental result of influence of compounds of the present invention on high fat-induced NAFLD/NASH mice

|  | $LDL^{p1}$ | TG | Liver Weight/Body Weight | NAFLD Activity Score$^{p2}$ |
|---|---|---|---|---|
| Model group | 0.31 | — | — | 3 |
| Compound 2-1 | 0.21 | −53%* | −9%* | 1 |

*an increased or decreased ratio of the experimental group to the model group, wherein the negative value represents a decrease, and the positive value represents an increase.

LDL represents low density lipoprotein; TG represents triglyceride; and p value has a statistical significance, wherein p1<0.01 and p2<0.001.

4 Conclusion

The compound 2-1 of the present invention exhibits a good improving effect on the NAFLD symptom of the mice at the administration dosage. An increase in liver weight is a common side effect caused by the FXR agonist. It can be known from the experimental result that the compounds of the present invention cause no an obvious increase in the liver weight/body weight ratio of the experimental animal, i.e. showing no obvious side effect, and therefore the compounds of the present invention are of high safety.

DETAILED DESCRIPTION OF THE INVENTION

The aforementioned content of the present invention is further described in detail below by the detailed description in the form of examples. However, the scope of the above subject matter of the present invention should not be construed as being limited to the following examples. Any technique achieved based on the aforementioned content of the present invention shall fall within the scope of the present invention.

Example 1: preparation of 2-((RS, 4RS, 5SR)-5-((5-cyclopropyl-3-(2,6-dichlorophenyl) isoxazol-4-yl)methoxy)-2-azabicyclo[2.2.1]heptan-2-yl)-4-methoxybenzo[d]thiazole-6-carboxylic acid (compound 1)

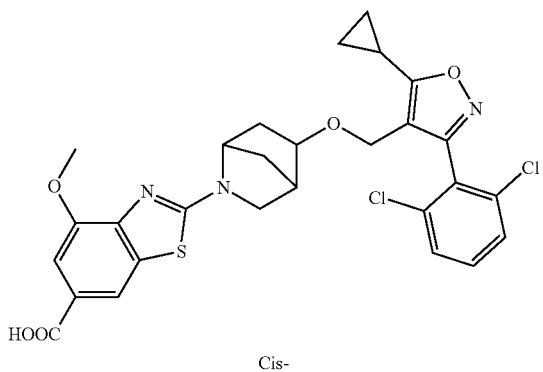 [SMILES: COc1cc(C(=O)O)cc2sc(N3CC4CC3CC4OCc3c(-c4c(Cl)cccc4Cl)noc3C3CC3)nc12]

Cis-

1. Preparation of tert-butyl (1RS, 4RS, 5SR)-5-((5-cyclopropyl-3-(2,6-dichlorophenyl) isoxazol-4-yl) methoxy)-2-azabicyclo[2.2.1]heptane-2-carboxylate

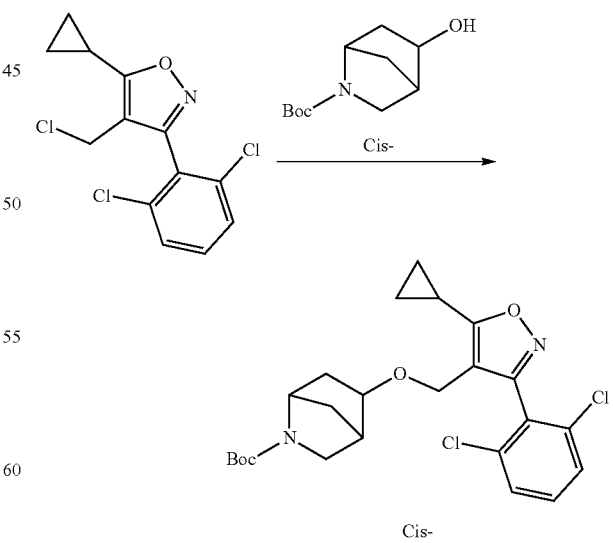

Tert-butyl (1RS, 4RS, 5SR)-5-hydroxy-2-azabicyclo[2.2.1]heptane-2-carboxylate (700 mg, 3.3 mol), potassium tert-butoxide (560 mg, 5.0 mmol), 18-crown-6 (1.32 g, 5.0 mmol) and KI (830 mg, 5.0 mmol) were added to THF (15 mL), 4-(chloromethyl)-5-cyclopropyl-3-(2,6-dichlorophenyl)isoxazole (1.20 g, 4.0 mmol) was then added, and the mixture solution reacted at 50° C. for 6 hrs. Water (100 mL) and ethyl acetate (100 mL) were added for extraction, and the organic phase was concentrated, and purified by silica-gel column chromatography (petroleum ether:ethyl acetate=8:1) to obtain the title compound (1.38 g, yield 87.3%).

2. Preparation of 4-((((1RS, 4RS, 5SR)-2-azabicyclo[2.2.1]heptan-5-yl)oxy)methyl)-5-cyclopropyl-3-(2,6-dichlorophenyl)isoxazole

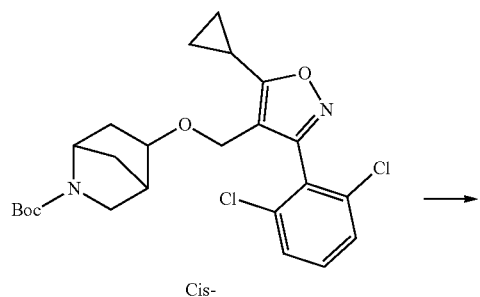

Cis-

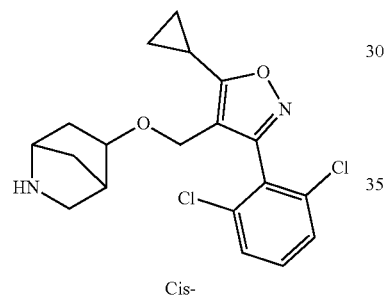

Cis-

Tert-butyl (1RS, 4RS, 5SR)-5-((5-cyclopropyl-3-(2,6-dichlorophenyl)isoxazol-4-yl) methoxy)-2-azabicyclo[2.2.1]heptane-2-carboxylate (1.18 g, 2.5 mmol) was added to DCM (15 mL), and then TFA (8 mL) was added. The mixture solution reacted under an ice water bath for 2 hrs. The pH of the reaction solution was adjusted to 8 with a saturated sodium bicarbonate solution under an ice water bath, and water (100 mL) and DCM (100 mL) were added for extraction. The organic phase was dried over anhydrous sodium sulfate and concentrated to obtain the title compound (900 mg, yield 96.4%).

3. Preparation of methyl 2-amino-4-methoxybenzo[d]thiazole-6-carboxylate

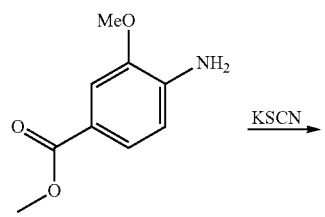

KSCN

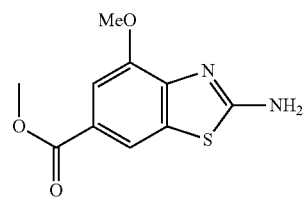

Methyl 4-amino-3-methoxybenzoate (1.81 g, 10.0 mmol) and KSCN (3.88 g, 40.0 mmol) were added to glacial acetic acid (10 mL), and 15 mins later, bromine (1.60 g, 10.0 mmol) was added. The mixture solution reacted at 25° C. for 16 hrs. The pH of the reaction solution was adjusted to 8 with ammonium hydroxide. After suction filtration, the solid was dried to obtain a crude title compound (2.40 g), which would be directly used in the next step without being purified.

4. Preparation of methyl 2-bromo-4-methoxybenzo[d]thiazole-6-carboxylate

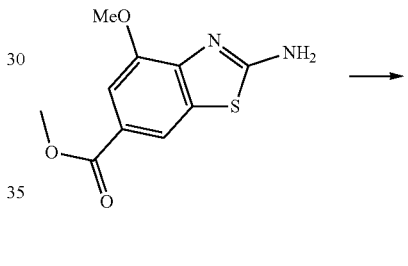

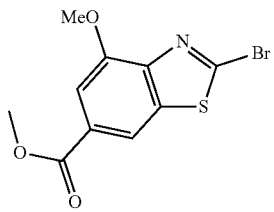

The crude methyl 2-amino-4-methoxybenzo[d]thiazole-6-carboxylate (2.40 g, 10.0 mmol) and copper bromide (3.35 g, 15.0 mmol) were added to acetonitrile (20 mL). Tert-butyl nitrite (1.55 g, 15.0 mmol) was added dropwise at 0° C., and after the addition was completed, the mixture solution was stirred and reacted at 25° C. for 0.5 hr. Water (100 mL) and ethyl acetate (100 mL) were added for extraction, and the organic phase was concentrated, and purified by silica-gel column chromatography (petroleum ether:ethyl acetate=10:1) to obtain the title compound (1.21 g, two-step total yield: 40.1%).

5. Preparation of methyl 2-((1RS, 4RS, 5SR)-5-((5-cyclopropyl-3-(2,6-dichlorophenyl) isoxazol-4-yl)methoxy)-2-azabicyclo[2.2.1]heptan-2-yl)-4-methoxybenzo[d]thiazole-6-carboxylate

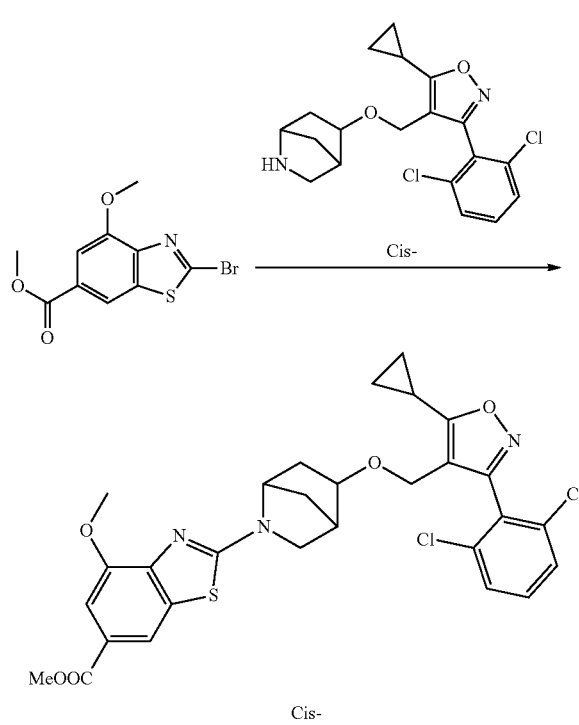

Methyl 2-bromo-4-methoxybenzo[d]thiazole-6-carboxylate (157 mg, 0.52 mmol), 4-((((1RS, 4RS, 5SR)-2-azabicyclo[2.2.1]heptan-5-yl)oxy)methyl)-5-cyclopropyl-3-(2,6-dichlorophenyl)isoxazole (100 mg, 0.26 mmol) and cesium carbonate (254 mg, 0.78 mol) were added to DMA (2 mL), and the mixture solution reacted at 110° C. for 16 hrs. Water (50 mL) and ethyl acetate (50 mL) were added for extraction, and the organic phase was concentrated, and purified by silica-gel column chromatography (petroleum ether:ethyl acetate=5:1) to obtain the title compound (80 mg, yield: 50.4%).

6. Preparation of 2-((1RS, 4RS, 5SR)-5-((5-cyclopropyl-3-(2,6-dichlorophenyl) isoxazol-4-yl)methoxy)-2-azabicyclo[2.2.1]heptan-2-yl)-4-methoxybenzo[d]thiazole-6-carboxylic acid

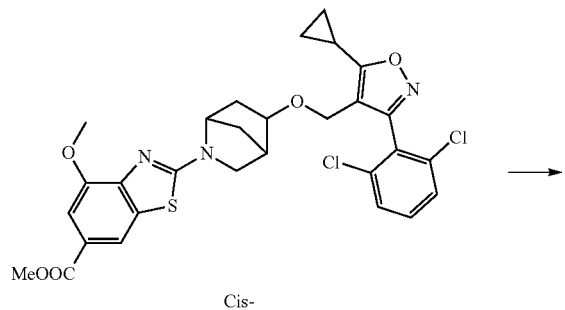

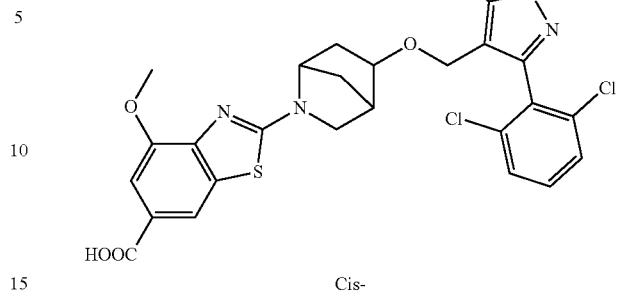

Methyl 2-((1RS, 4RS, 5SR)-5-((5-cyclopropyl-3-(2,6-dichlorophenyl)isoxazol-4-yl)methoxy)-2-azabicyclo[2.2.1]heptan-2-yl)-4-methoxybenzo[d]thiazole-6-carboxylate (80 mg, 0.13 mmol) was dissolved in the mixed solution of THF (1.5 mL) and methanol (1.5 mL), and then 2 M lithium hydroxide (0.65 mL) was added. The mixture solution was stirred and reacted at 40° C. for 1 hr. The pH of the reaction solution was adjusted to 6 with 1 M hydrochloric acid, and ethyl acetate (30 mL) was added for extraction. The organic phase was concentrated, and purified by silica gel column chromatography (dichloromethane:methanol=15:1) to obtain the title compound (40 mg, yield: 51.3%).

Molecular formula: $C_{28}H_{25}Cl_2N_3O_5S$ Molecular weight: 585.1 LC-MS (m/z): 586.2 (M+H$^+$)

$^1$H NMR (400 MHz, DMSO-d6) δ: 7.95 (s, 1H), 7.72-7.52 (m, 3H), 7.40-7.35 (m, 1H), 4.35-4.45 (m, 2H), 3.87 (s, 3H), 3.65-3.55 (m, 1H), 2.95-2.85 (m, 1H), 2.40-2.30 (m, 1H), 1.92-1.81 (m, 1H), 1.63-1.52 (m, 1H), 1.50-1.40 (m, 1H), 1.28-1.02 (m, 4H), 0.90-0.80 (m, 2H)

Example 2: Preparation of 2-((1RS, 4RS, 5SR)-5-((5-cyclopropyl-3-(2,6-dichlorophenyl) isoxazol-4-yl)methoxy)-2-azabicyclo[2.2.1]heptan-2-yl)benzo[d]thiazole-6-carboxylic acid (compound 2)

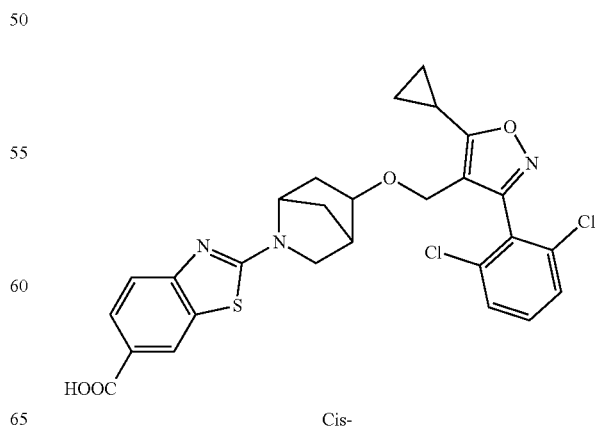

1. Preparation of tert-butyl (1RS, 4RS, 5SR)-5-((5-cyclopropyl-3-(2,6-dichlorophenyl) isoxazol-4-yl)methoxy)-2-azabicyclo[2.2.1]heptane-2-carboxylate

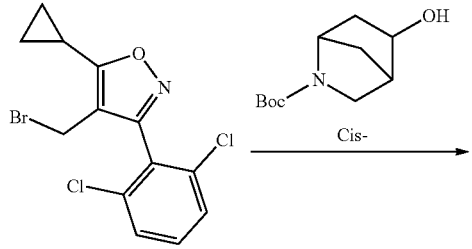
Cis-

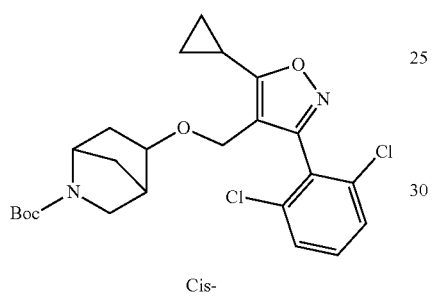
Cis-

Tert-butyl (1RS, 4RS, 5SR)-5-hydroxy-2-azabicyclo[2.2.1]heptane-2-carboxylate (213 mg, 1.0 mmol), potassium tert-butoxide (168 mg, 1.5 mmol) and 18-crown-6 (396 mg, 1.5 mmol) were added to THF (20 mL), and 25 mins later, 4-(bromomethyl)-5-cyclopropyl-3-(2,6-dichlorophenyl)isoxazole (416 mg, 1.2 mmol) was added. The mixture solution reacted at 25° C. for 16 hrs. Water (100 mL) and ethyl acetate (100 mL) were added for extraction, and the organic phase was concentrated and purified by silica-gel column chromatography (petroleum ether:ethyl acetate=3:1) to obtain the title compound (367 mg, yield: 76.7%).

2. Preparation of 4-((((1RS, 4RS, 5SR)-2-azabicyclo[2.2.1]heptan-5-yl)oxy)methyl)-5-cyclopropyl-3-(2,6-dichlorophenyl)isoxazole

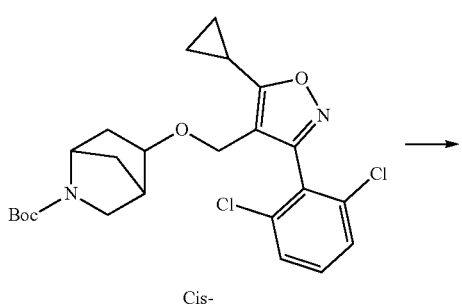
Cis-

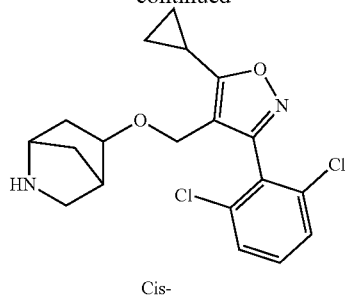
Cis-

Tert-butyl (1RS, 4RS, 5SR)-5-((5-cyclopropyl-3-(2,6-dichlorophenyl)isoxazol-4-yl)methoxy)-2-azabicyclo[2.2.1]heptane-2-carboxylate (360 mg, 0.75 mmol) was added to DCM (10 mL), and then TFA (3 mL) was added. The mixture solution reacted under an ice water bath for 2 hrs. The pH of the reaction solution was adjusted to 8 with a saturated sodium bicarbonate solution under an ice water bath, and water (100 mL) and DCM (100 mL) were added for extraction. The organic phase was dried over anhydrous sodium sulfate, and concentrated to obtain the title compound (280 mg, yield: 98.3%).

3. Preparation of methyl 2-((1RS, 4RS, 5SR)-5-((5-cyclopropyl-3-(2,6-dichlorophenyl) isoxazol-4-yl)methoxy)-2-azabicyclo[2.2.1]heptan-2-yl)benzo[d]thiazole-6-carboxylate

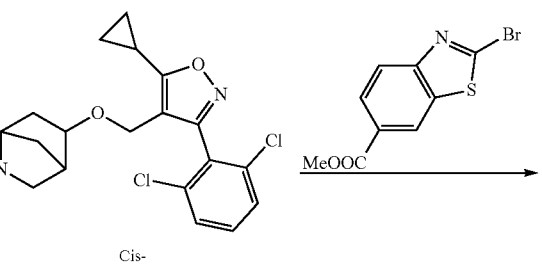
Cis-

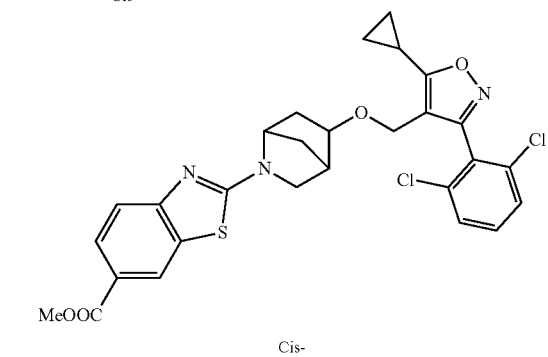
Cis- 4-((((1RS,4RS,5SR)-2-azabicyclo[2.2.1]heptan-5-yl)oxy)methyl)-5-cyclopropyl-3-(2,6-dichlorophenyl)isoxazole (280 mg, 0.74 mmol), methyl 2-bromobenzo[d]thiazole-6-carboxylate (403 mg, 1.48 mmol) and cesium carbonate (724 mg, 2.22 mmol) were added to DMA (6 mL), and the mixture solution reacted at 100° C. under microwave for 1 hr. Water (100 mL) and ethyl acetate (100 mL) were added for extraction, and the organic phase was concentrated, and purified by silica-gel column chromatography (petroleum ether:ethyl acetate=10:1) to obtain the title compound (305 mg, yield: 72.6%).

4. Preparation of 2-((RS, 4RS, 5SR)-5-((5-cyclopropyl-3-(2,6-dichlorophenyl) isoxazol-4-yl) methoxy)-2-azabicyclo[2.2.1]heptan-2-yl)benzo[d]thiazole-6-carboxylicacid

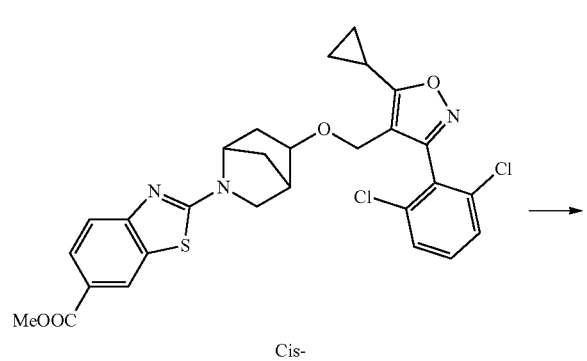

Cis-

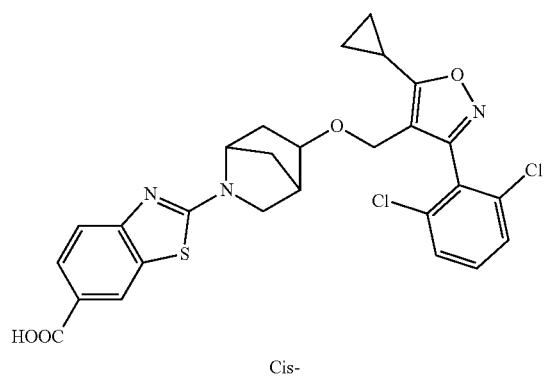 [SMILES: O=C(O)c1ccc2nc(N3CC4CC3CC4OCc3c(-c4c(Cl)cccc4Cl)noc3C3CC3)sc2c1]

Cis-

Methyl 2-((1RS,4RS,5SR)-5-((5-cyclopropyl-3-(2,6-dichlorophenyl)isoxazol-4-yl) methoxy)-2-azabicyclo[2.2.1]heptan-2-yl)benzo[d]thiazole-6-carboxylate (300 mg, 0.53 mmol) and lithium hydroxide monohydrate (111 mg, 2.64 mmol) were added to the mixed solution of methanol (6 mL), THF (6 mL) and water (3 mL), and the resultant mixture was stirred and reacted at 55° C. for 3 hrs. The pH of the reaction solution was adjusted to 2 with 1 M hydrochloric acid, and water (100 mL) and ethyl acetate (100 mL) were then added for extraction. The organic phase was washed with a saturated sodium chloride solution (100 mL), concentrated, and purified by reverse-phase preparative chromatography (methanol/water=70%) to obtain the title compound (78 mg, yield: 26.7%).

Molecular formula: $C_{27}H_{23}Cl_2N_3O_4S$ Molecular weight: 555.1 LC-MS (m/z): 556.2 (M+H$^+$)

$^1$H NMR (400 MHz, DMSO-d6) δ: 8.31 (s, 1H), 7.90-7.82 (m, 1H), 7.75-7.55 (m, 3H), 7.56-7.35 (m, 1H), 4.32-4.25 (m, 2H), 3.62-3.58 (m, 1H), 2.98-2.88 (m, 1H), 2.55-2.52 (m, 2H), 2.40-2.30 (m, 1H), 2.10-1.99 (m, 1H), 1.98-1.85 (m, 1H), 1.65-1.54 (m, 1H), 1.52-1.42 (m, 1H), 1.30-1.25 (m, 1H), 1.20-1.10 (m, 2H), 1.10-1.05 (m, 2H).

Example 2-1: Preparation of 2-((1S, 4S, 5R)-5-((5-cyclopropyl-3-(2,6-dichlorophenyl) isoxazol-4-yl) methoxy)-2-azabicyclo[2.2.1]heptan-2-yl)benzo[d]thiazole-6-carboxylic acid (compound 2-1)

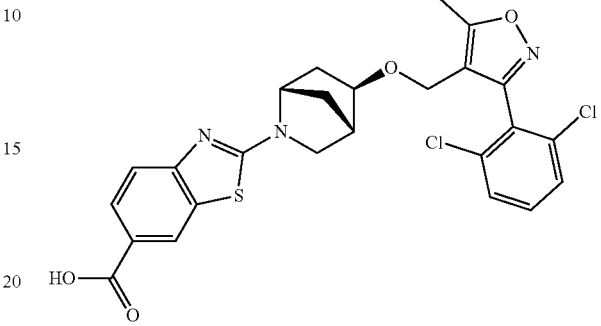

1. Preparation of tert-butyl (1S, 4R)-2-azabicyclo[2.2.1]heptan-5-en-2-carboxylate

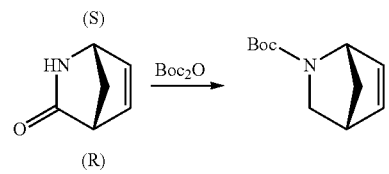

(1S, 4R)-2-azabicyclo[2.2.1]heptan-5-en-3-one (3.0 g, 27.5 mmol) was dissolved in THF (80 mL), and LiAlH$_4$ (1.36 g, 35.8 mmol) was added at 0° C. The reaction solution reacted at 25° C. for 3 hrs, and then reacted at an elevated temperature of 60° C. for 4 hrs. Then, water (2 mL) was added at 0° C. to quench the reaction. The reaction solution was filtered through celite, the filter cake was washed with ethyl acetate (50 mL), and the filtrate was concentrated to 50 mL. Boc$_2$O (9.0 g, 41.2 mmol) was added to the concentrated filtrate, and the mixture solution reacted at 25° C. for 16 hrs. The reaction solution was concentrated, and purified by silica-gel column chromatography (petroleum ether:ethyl acetate=10:1) to obtain the product (3.0 mg, two-step yield: 55.9%).

2. Preparation of tert-butyl (1S, 4S, 5R)-5-hydroxy-2-azabicyclo[2.2.1]heptane-2-carboxylate

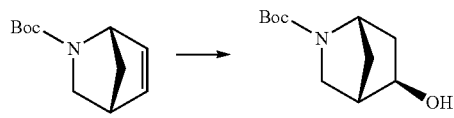 [SMILES: CC(C)(C)OC(=O)N1C[C@H]2C=C[C@@H]1C2 ; CC(C)(C)OC(=O)N1C[C@@H]2C[C@H]1C[C@H]2O]

Tert-butyl (1S, 4R)-2-azabicyclo[2.2.1]heptan-5-en-2-carboxylate (1.5 g, 7.68 mmol) and NaBH$_4$ (0.24 g, 6.3 mmol) were added to THF (20 mL), and the mixture solution reacted at 25° C. and under a nitrogen atmosphere for 0.5 hr. The solution of dimethyl sulfate (0.57 mL, 6.3 mmol) in THF (2 mL) was then added, and the mixture solution reacted at 35° C. for 4 hrs. The reaction solution was cooled to 0° C., and water (5 mL) was added for quenching. H₂O₂ (0.96 mL, 30%) and a aqueous solution of 1 M sodium hydroxide (15 mL, 15 mmol) was then added dropwise, and the mixture solution reacted at 25° C. for 1 hr. Ethyl acetate (100 mL) was added for extraction, and the organic layer was concentrated, and purified by silica-gel column chromatography (petroleum ether:ethyl acetate=2:1) to obtain the product (700 mg, yield: 42.7%).

3. Preparation of tert-butyl (1S, 4S, 5R)-5-((5-cyclopropyl-3-(2,6-dichlorophenyl) isoxazol-4-yl) methoxy)-2-azabicyclo[2.2.1]heptane-2-carboxylate

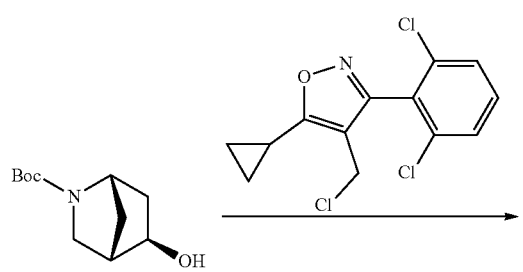

Tert-butyl (1S, 4S, 5R)-5-hydroxy-2-azabicyclo[2.2.1]heptane-2-carboxylate (0.2 g, 0.94 mmol) was dissolved into THF (30 mL), and potassium tert-butoxide (158 mg, 1.4 mmol) and 18-crown-6-ether (248 mg, 0.94 mmol) were added, and then the mixture solution reacted at 25° C. for 0.5 hr. 4-(chloromethyl)-5-cyclopropyl-3-(2,6-dichlorophenyl) isoxazole (427 mg, 1.4 mmol) and KI (232.4 mg, 1.4 mmol) were added, and the mixture solution reacted at 40° C. for 2 hrs. The reaction solution was concentrated, and purified by silica-gel column chromatography (petroleum ether:ethyl acetate=2:1) to obtain a product (300 mg, yield: 66.6%).

4. Preparation of 4-((((1S, 4S, 5R)-2-azabicyclo[2.2.1]heptan-5-yl)oxy)methyl)-5-cyclopropyl-3-(2,6-dichlorophenyl)isoxazole trifluoroacetate

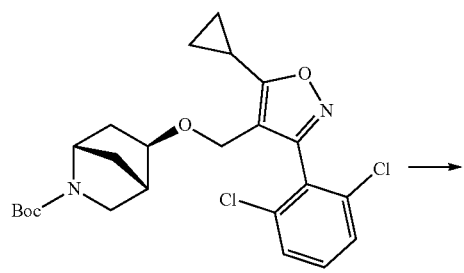

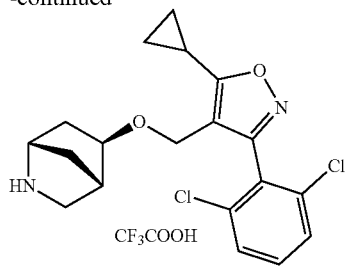

Tert-butyl (1S, 4S, 5R)-5-((5-cyclopropyl-3-(2,6-dichlorophenyl)isoxazol-4-yl) methoxy)-2-azabicyclo[2.2.1]heptane-2-carboxylate (0.25 g, 0.52 mmol) was added to DCM (8 mL), TFA (2 mL) was added, and the mixture solution reacted at 25° C. for 2 hrs. The reaction solution was concentrated to obtain a crude product (400 mg), which would be directly used in the next step without being purified.

5. Preparation of methyl 2-((1S, 4S, 5R)-5-((5-cyclopropyl-3-(2,6-dichlorophenyl) isoxazol-4-yl) methoxy)-2-azabicyclo[2.2.1]heptan-2-yl)benzo[d]thiazole-6-carboxylate

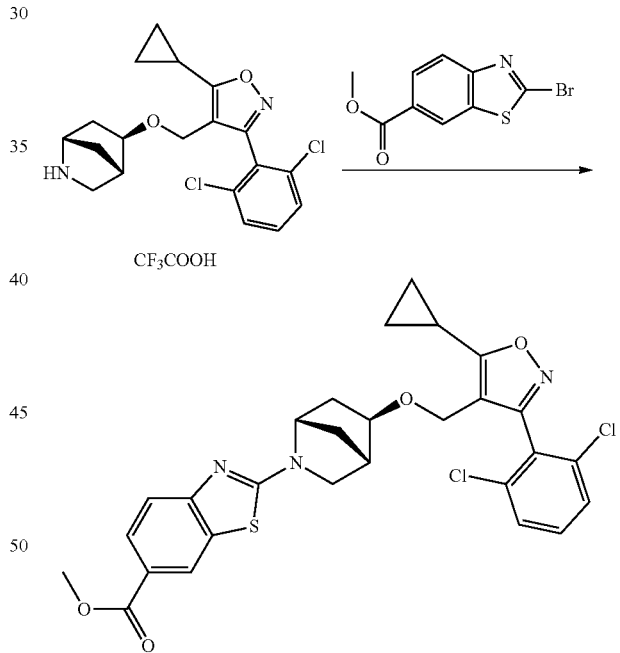

4-((((1S, 4S, 5R)-2-azabicyclo[2.2.1]heptan-5-yl)oxy)methyl)-5-cyclopropyl-3-(2,6-dichlorophenyl)isoxazole trifluoroacetate (400 mg, crude product), methyl 2-bromobenzo[d]thiazole-6-carboxylate (212 mg, 0.78 mmol) and cesium carbonate (508 mg, 1.56 mmol) were added to dimethyl adipate (8 mL), and the mixture solution reacted at 120° C. under microwave for 0.5 hr. The reaction solution was then poured into water (20 mL), and filtrated. The filter cake was purified by silica-gel column chromatography (dichloromethane:methanol=20:1) to obtain a product (200 mg, two-step yield: 67.4%).

6. Preparation of 2-((1S, 4S, 5R)-5-((5-cyclopropyl-3-(2,6-dichlorophenyl)isoxazol-4-yl)methoxy)-2-azabicyclo[2.2.1]heptan-2-yl)benzo[d]thiazole-6-carboxylicacid

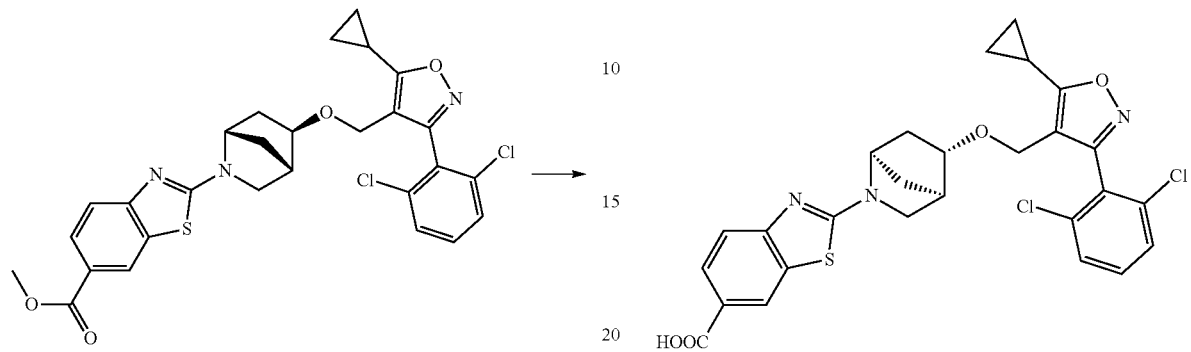

Methyl 2-((1S, 4S, 5R)-5-((5-cyclopropyl-3-(2,6-dichlorophenyl)isoxazol-4-yl) methoxy)-2-azabicyclo[2.2.1]heptan-2-yl)benzo[d]thiazole-6-carboxylate (200 mg, 0.35 mmol) and lithium hydroxide monohydrate (103 mg, 2.45 mmol) were dissolved into the mixed solvent of methanol (8 mL), tetrahydrofuran (8 mL) and water (8 mL), and the mixture solution was stirred at 40° C. for 2 hrs. The reaction solution was concentrated, and water (20 mL) was added to the residue. Then pH of the solution was adjusted to 2 with 1 M dilute hydrochloric acid, and ethyl acetate (50 mL×2) was added for extraction. The organic phases were combined and concentrated, and the residue was purified by $C_{18}$ reverse-phase silica-gel column chromatography (methanol:water=0%-70%) to obtain a product (70 mg, yield: 35.9%).

Molecular formula: $C_{27}H_{23}Cl_2N_3O_4S$ Molecular weight: 555.1 LC-MS (m/z): 556.1 (M+H$^+$)

$[\alpha]_D^{20}$=−84.97 (C=1.0, CH$_3$OH)

$^1$H-NMR (400 MHz, CDCl$_3$) δ 8.34 (s, 1H), 8.05 (dd, J=1.6 Hz, J=8.4 Hz, 1H), 7.55 (d, J=8.8 Hz, 1H), 7.32-7.45 (m, 3H), 4.26-4.33 (m, 2H), 3.61 (d, J=7.2 Hz, 1H), 3.50 (s, 2H), 3.03 (s, 1H), 2.60 (s, 1H), 2.10-2.15 (m, 1H), 2.01-2.10 (m, 1H), 1.65-1.69 (m, 1H), 1.44 (d, J=13.6 Hz, 1H), 1.26-1.30 (m, 2H), 1.11-1.17 (m, 2H).

Example 2-2: Preparation of 2-((1R, 4R, 5S)-5-((5-cyclopropyl-3-(2,6-dichlorophenyl) isoxazol-4-yl) methoxy)-2-azabicyclo[2.2.1]heptan-2-yl)benzo[d] thiazole-6-carboxylic acid (compound 2-2)

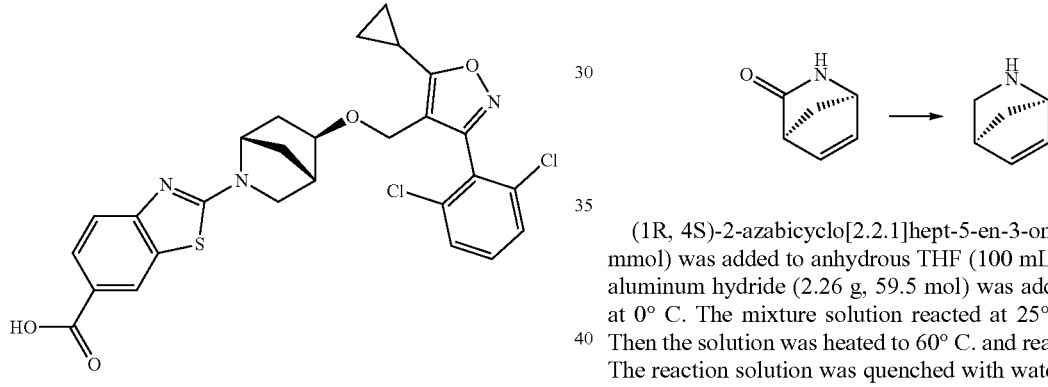

1. Preparation of (R, 4S)-2-azabicyclo[2.2.1]hept-5-ene (1R, 4S)-2-azabicyclo[2.2.1]hept-5-en-3-one (5.0 g, 45.8 mmol) was added to anhydrous THF (100 mL), and lithium aluminum hydride (2.26 g, 59.5 mol) was added in batches at 0° C. The mixture solution reacted at 25° C. for 3 hrs. Then the solution was heated to 60° C. and reacted for 4 hrs. The reaction solution was quenched with water at 0° C. EA (100 mL) and sodium chloride aqueous solution (80 mL) were added for extraction, and the organic phase was dried over anhydrous sodium sulfate to obtain a crude product which would be directly used in the next step without being purified.

2. Preparation of tert-butyl (1R, 4S)-2-azabicyclo[2.2.1]hept-5-ene-2-carboxylate (1R, 4S)-2-azabicyclo[2.2.1]hept-5-ene (4.35 g, 45.8 mmol) was added to THF 100 mL), (Boc)$_2$O (15.0 g, 68.7 mmol) was then added, and the mixture solution reacted at 25° C. for 1 hr. The system was spin-dried directly, and purified by silica-gel column chromatography (PE:EA=10:1) to obtain a product (7.0 g, two-step yield: 78.4%).

3. Preparation of tert-butyl (1R, 4R, 5S)-5-hydroxy-2-azabicyclo[2.2.1]heptane-2-carboxylate

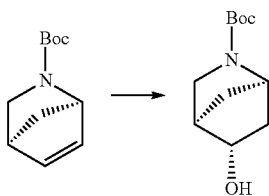 [SMILES: CC(C)(C)OC(=O)N1C[C@@H]2C=C[C@H]1C2 ; CC(C)(C)OC(=O)N1C[C@H]2C[C@@H]1C[C@@H]2O]

Tert-butyl (1R, 4S)-2-azabicyclo[2.2.1]hept-5-ene-2-carboxylate (1.5 g, 7.68 mmol) and sodium borohydride (0.24 g, 6.30 mmol) were added to THF (9 mL), and the mixture solution was stirred and reacted at 23° C. and under a nitrogen atmosphere for 0.5 hr. The solution of dimethyl sulfate (0.57 mL, 6.30 mmol) in THF (2 mL) was added at 35° C., and the mixture solution reacted at 35° C. for 4 hrs with vigorous stirring. The reaction solution was cooled to 0° C., and quenched with water (5.0 mL). 1M NaOH (15 mL) and hydrogen peroxide (30 wt % in $H_2O$, 0.96 mL) were then added in sequence, and the mixture solution reacted at 23° C. for 1 hr. EA (100 mL) and water (50 mL) were added for extraction. The organic phase was spin-dried, and purified by silica-gel column chromatography (PE: EA=2:1) to obtain a product (600 mg, yield: 36.7%).

4. Preparation of tert-butyl (1R, 4R, 5S)-5-((5-cyclopropyl-3-(2,6-dichlorophenyl) isoxazol-4-yl) methoxy)-2-azabicyclo[2.2.1]heptane-2-carboxylate

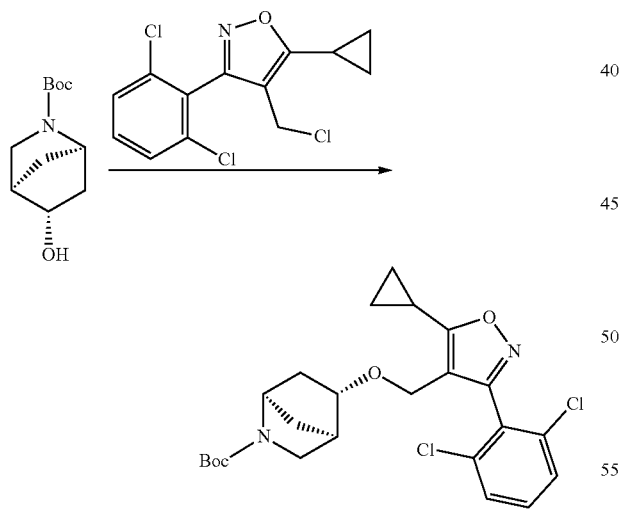

Tert-butyl (1R, 4R, 5S)-5-hydroxy-2-azabicyclo[2.2.1] heptane-2-carboxylate (600 mg, 2.8 mmol), 18-crown-6-ether (739 mg, 2.8 mmol) and potassium tert-butoxide (627 mg, 5.6 mmol) were added to THF (80 mL), and the mixture solution reacted at 25° C. for 0.5 hr. 4-(chloromethyl)-5-cyclopropyl-3-(2,6-dichlorophenyl)isoxazole (1.28 g, 4.2 mmol) and potassium iodide (697 mg, 4.2 mmol) were then added, and the mixture solution reacted at 50° C. for 4 hrs. EA (100 mL) and water (50 mL) were added for extraction. The organic phase was spin-dried, and purified by column chromatography (PE:EA=2:1) to obtain a product (700 mg, yield: 52.2%).

5. Preparation of 4-(((((1R, 4R, 5S)-2-azabicyclo[2.2.1]heptan-5-yl)oxy)methyl)-5-cyclopropyl-3-(2,6-dichlorophenyl)isoxazole

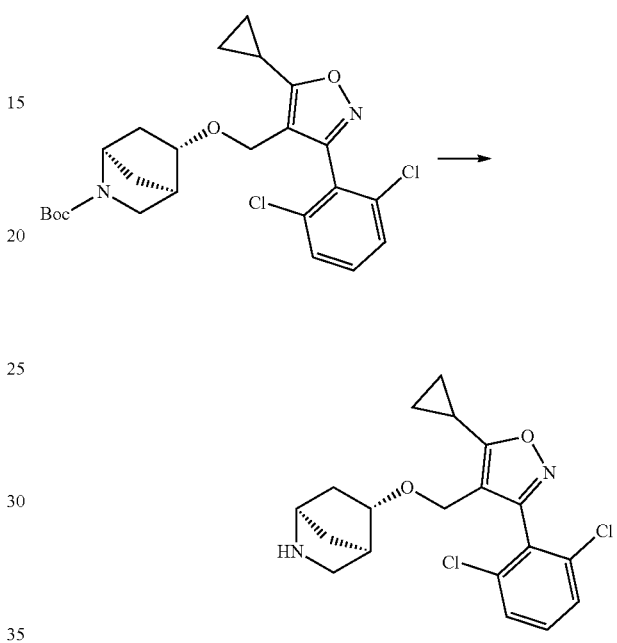

Tert-butyl (1R, 4R, 5S)-5-((5-cyclopropyl-3-(2,6-dichlorophenyl)isoxazol-4-yl) methoxy)-2-azabicyclo[2.2.1]heptane-2-carboxylate (700 mg, 1.46 mmol) was slowly added to a ethanol solution (6 mL) containing 4 M HCl at 0° C., and the mixture solution reacted at 0° C. for 4 hrs. After the reaction was completed, the pH of the reaction solution was adjusted to 8 with a saturated sodium bicarbonate solution at 0° C. The organic solvent in the system was distilled out in spin-dry manner. Ethyl acetate (100 mL) and water (50 mL) were added for extraction. The organic phase was dried over anhydrous sodium sulfate, filtrated, and spin-dried to obtained a product (400 mg, yield: 72.3%).

6. Preparation of methyl 2-((1R, 4R, 5S)-5-((5-cyclopropyl-3-(2,6-dichlorophenyl) isoxazol-4-yl) methoxy)-2-azabicyclo[2.2.1]benzo[d]thiazol-6-carboxylate

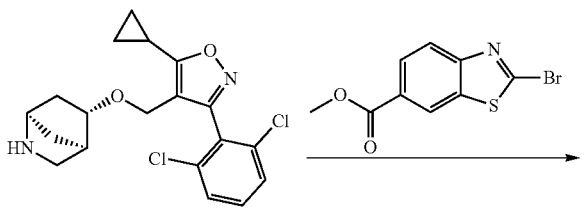

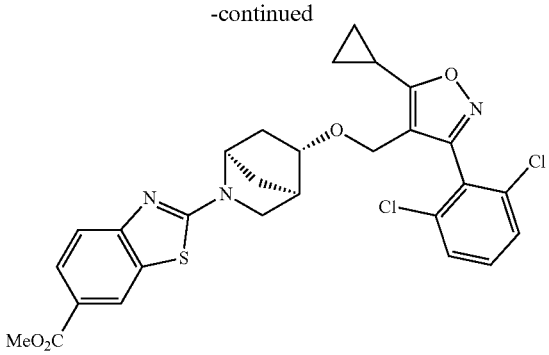

4-((((1R, 4R, 5S)-2-azabicyclo[2.2.1]heptan-5-yl)oxy)methyl)-5-cyclopropyl-3-(2,6-dichlorophenyl)isoxazole (400 mg, 1.06 mmol), methyl 2-bromobenzo[d]thiazole-6-formate (431 mg, 1.58 mmol) and cesium carbonate (691 mg, 2.12 mmol) were added to DMA (10 mL), and the mixture solution reacted at 110° C. under microwave for 0.5 hr. After the reaction was completed, the reaction solution was cooled to 25° C. Ethyl acetate (100 mL) and water (50 mL) were then added for extraction. The organic phase was spin-dried, and purified by silica-gel column chromatography (PE:EA=5:1) to obtain a product (450 mg, yield: 74.5%).

7. Preparation of 2-((1R, 4R, 5S)-5-((5-cyclopropyl-3-(2,6-dichlorophenyl)isoxazol-4-yl) methoxy)-2-azabicyclo[2.2.1]heptan-2-yl)benzo[d]thiazole-6-carboxylic acid

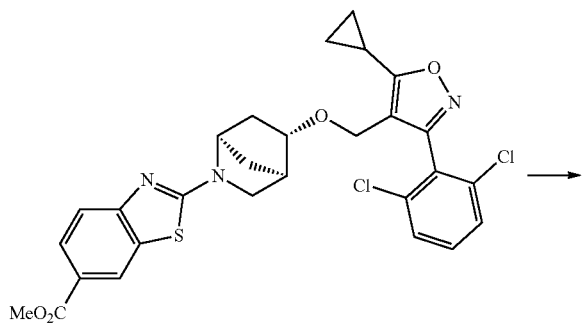

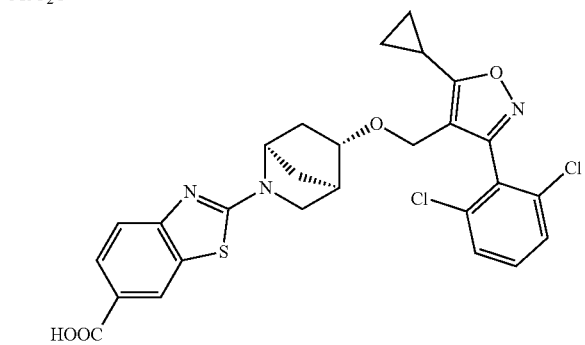

Methyl 2-((1R, 4R, 5S)-5-((5-cyclopropyl-3-(2,6-dichlorophenyl)isoxazol-4-yl) methoxy)-2-azabicyclo[2.2.1]benzo[d]thiazole-6-carboxylate (450 mg, 0.79 mmol) was added to the mixed solution of methanol (5 mL) and THF (5 mL), the mixture solution was then added to an aqueous solution (2 mL) containing lithium hydroxide monohydrate (133 mg, 3.2 mmol), and the system was heated to 50° C. and reacted for 12 hrs. After the reaction was completed, the reaction solution was cooled to 25° C., and the pH of the system was adjusted to 4 with 1 N HCl. The solvent was distilled out in spin-dry manner. Ethyl acetate (100 mL) and a sodium chloride aqueous solution (50 mL) were added for extraction. The organic phase was spin-dried, and purified by silica-gel column chromatography (DCM:MeOH=40:1) to obtain a product (390 mg, yield: 89.1%).

Molecular formula: $C_{27}H_{23}C_2N_3O_4S$ Molecular weight: 555.1 LC-MS (m/z): 556.1 (M+H$^+$)

$[\alpha]_D^{20}$=+76.2 (C=1.0, CH$_3$OH)

$^1$H-NMR (400 MHz, CDCl$_3$) δ: 8.25 (s, 1H), 8.08-8.04 (m, 1H), 7.62 (m, 1H), 7.47-7.34 (m, 3H), 4.35-4.28 (m, 2H), 3.71-3.68 (m, 2H), 2.68 (s, 1H), 2.15-2.08 (m, 2H), 1.85-1.70 (m, 2H), 1.55-1.48 (m, 1H), 1.30-1.21 (m, 3H), 1.20-1.09 (m, 2H).

Example 3: Preparation of 2-((1RS, 4RS, 5RS)-5-((5-cyclopropyl-3-(2,6-dichlorophenyl) isoxazol-4-yl)methoxy)-2-azabicyclo[2.2.1]heptan-2-yl)benzo[d]thiazole-6-carboxylic acid (compound 3)

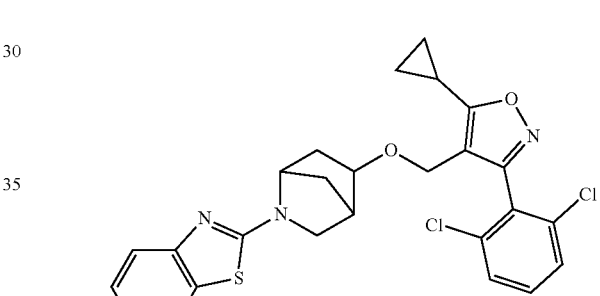

1. Preparation of tert-butyl (1RS, 4RS, 5RS)-5-((5-cyclopropyl-3-(2,6-dichlorophenyl) isoxazol-4-yl) methoxy)-2-azabicyclo[2.2.1]heptane-2-carboxylate

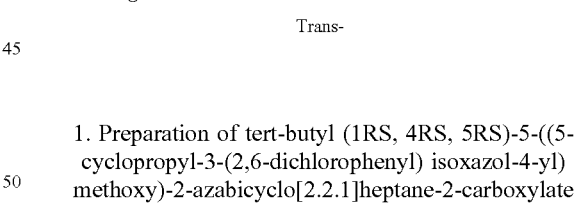

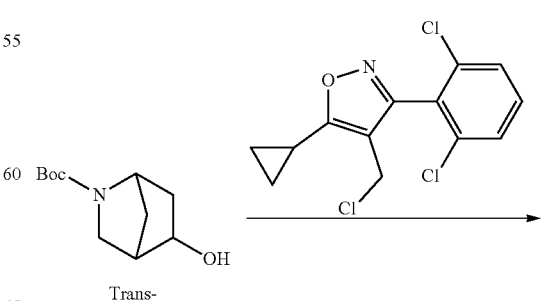

-continued

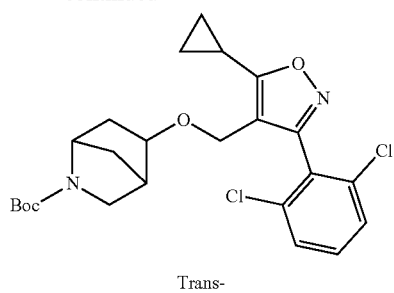
Trans-

Tert-butyl (1RS, 4RS, 5RS)-5-hydroxy-2-azabicyclo [2.2.1]heptane-2-carboxylate (0.25 g, 1.17 mmol) was dissolved into THF (30 mL), potassium tert-butoxide (196 mg, 1.75 mmol) and 18-crown-6 (310 mg, 1.17 mmol) were added, and the mixture solution reacted at 25° C. for 0.5 hr. 4-(chloromethyl)-5-cyclopropyl-3-(2,6-dichlorophenyl) isoxazole (530 mg, 1.75 mmol) and KI (290 mg, 1.75 mmol) were then added, and the mixture solution reacted at 30° C. for 4 hrs. The reaction solution was concentrated, and the resulted crude product was purified by silica-gel column chromatography (petroleum ether:ethyl acetate=3:1) to obtain the target product (450 mg, yield: 80%).

2. Preparation of 4-((((1RS, 4RS, 5RS)-2-azabicyclo[2.2.1]heptan-5-yl)oxy)methyl)-5-cyclopropyl-3-(2,6-dichlorophenyl)isoxazole trifluoroacetate

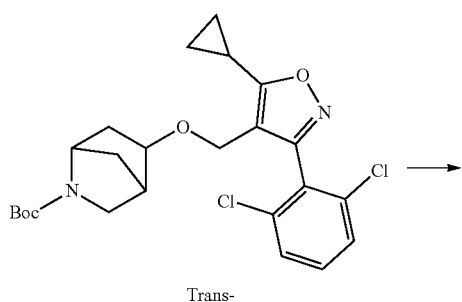
Trans-

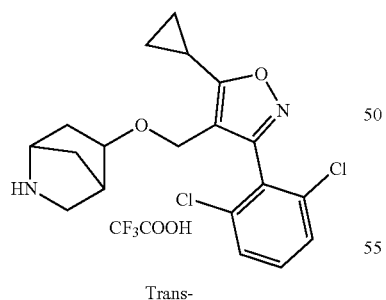
Trans-

Tert-butyl (1RS, 4RS, 5RS)-5-((5-cyclopropyl-3-(2,6-dichlorophenyl)isoxazol-4-yl) methoxy)-2-azabicyclo[2.2.1] heptane-2-carboxylate (0.4 g, 0.83 mmol) was added to dichloromethane (10 mL), trifluoroacetic acid (4 mL) was added, and the mixture solution reacted at 25° C. for 2 hrs. The reaction solution was concentrated to obtain a crude product (500 mg) which would be directly used in the next step.

3. Preparation of methyl 2-((1RS, 4RS, 5RS)-5-((5-cyclopropyl-3-(2,6-dichlorophenyl) isoxazol-4-yl) methoxy)-2-azabicyclo[2.2.1]heptan-2-yl)benzo[d]thiazole-6-carboxylate

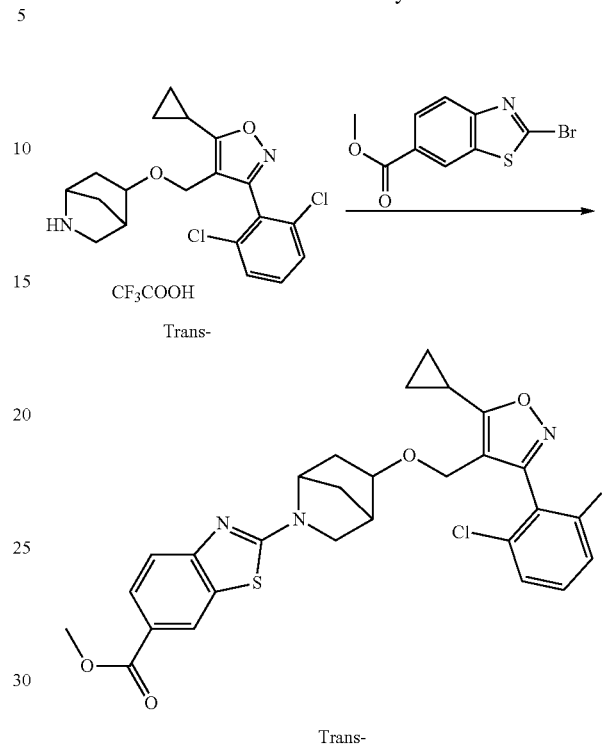

4-((((1RS, 4RS,5RS)-2-azabicyclo[2.2.1]heptan-5-yl) oxy)methyl)-5-cyclopropyl-3-(2,6-dichlorophenyl)isoxazole trifluoroacetate (500 mg, crude product), methyl 2-bromobenzo[d]thiazole-6-carboxylate (338 mg, 1.24 mmol) and cesium carbonate (811 mg, 2.49 mmol) were added to DMA (6 mL), and the mixture solution reacted at 120° C. under microwave for 0.5 hr. The reaction solution was then poured into water (20 mL), and filtered. The filter cake was purified by silica-gel column chromatography (dichloromethane:methanol=20:1) to obtain the target product (400 mg, two-step yield: 84.5%).

4. Preparation of 2-((1RS, 4RS, 5RS)-5-((5-cyclopropyl-3-(2,6-dichlorophenyl) isoxazol-4-yl) methoxy)-2-azabicyclo[2.2.1]heptan-2-yl)benzo[d]thiazole-6-carboxylic acid

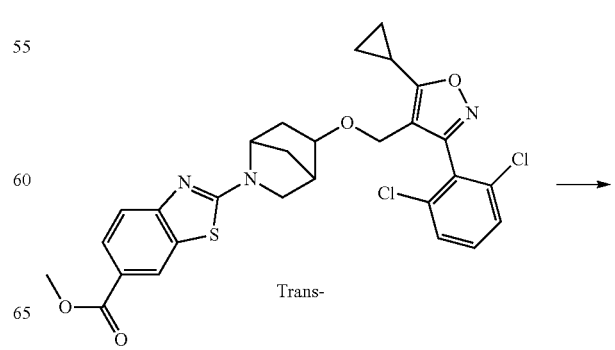
Trans-

-continued

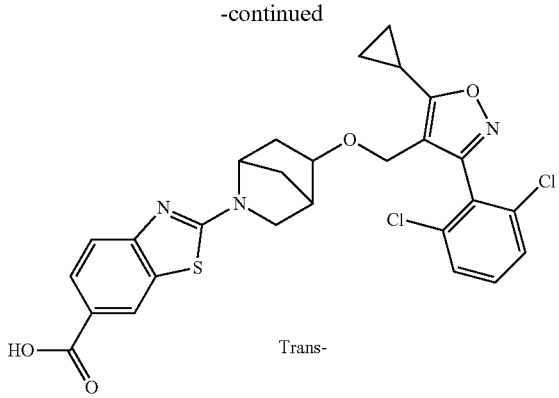

Trans-

Methyl 2-((1RS, 4RS, 5RS)-5-((5-cyclopropyl-3-(2,6-dichlorophenyl)isoxazol-4-yl) methoxy)-2-azabicyclo[2.2.1]heptan-2-yl)benzo[d]thiazole-6-carboxylate (200 mg, 0.35 mmol) and lithium hydroxide monohydrate (80 mg, 1.9 mmol) were dissolved into the mixed solvent of methanol (10 mL), tetrahydrofuran (10 mL) and water (10 mL), and the mixture solution was stirred at 40° C. for 2 hrs. The reaction solution was concentrated, and water (10 mL) was added to the residue. Then pH of the solution was adjusted to 2 with 1 M dilute hydrochloric acid, and ethyl acetate was added for extraction (100 mL×2). The organic phases were combined and concentrated, and the residue was purified by C18 reverse-phase silica-gel column chromatography (methanol: water=0%-70%) to obtain the target product (50 mg, yield: 25.7%).

Molecular formula: $C_{27}H_{23}Cl_2N_3O_4S$ Molecular weight: 555.1 LC-MS (m/z): 556.1 (M+H$^+$)

$^1$H-NMR (400 MHz, CDCl$_3$) δ 8.39 (s, 1H), 8.08 (d, J=8.0 Hz, 1H), 7.57 (d, J=8.4 Hz, 1H), 7.35 (d, J=8.0 Hz, 1H), 7.10-7.19 (m, 2H), 4.22-4.33 (m, 2H), 4.00-4.03 (m, 1H), 3.64 (s, 1H), 3.36 (s, 1H), 2.76 (s, 1H), 2.06-2.13 (m, 1H), 1.86-1.99 (m, 2H), 1.62 (d, J=10.0 Hz, 1H), 1.20-1.47 (m, 4H), 1.07-1.12 (m, 2H).

Example 4: Preparation of 2-((1RS, 4RS, 5SR)-5-((5-cyclopropyl-3-(2,6-dichlorophenyl) isoxazol-4-yl)methoxy)-2-azabicyclo[2.2.1]heptan-2-yl)-4-fluorobenzo[d]thiazole-6-carboxylic acid (compound 4)

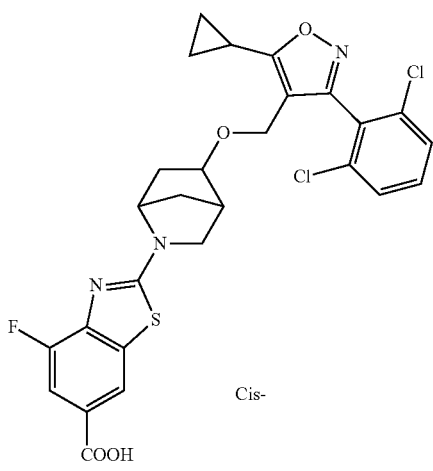 [SMILES: O=C(O)c1cc(F)c2nc(N3CC4CC3CC4OCc3c(-c4c(Cl)cccc4Cl)noc3C3CC3)sc2c1]

Cis-

1. Preparation of methyl 4-amino-3-fluorobenzoate

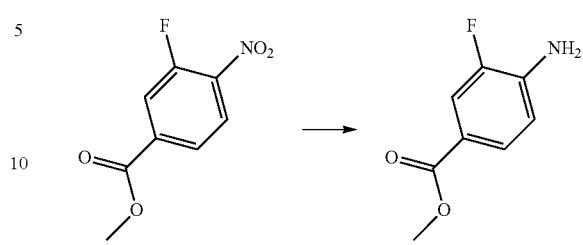

Methyl 3-fluoro-4-nitrobenzoate (1.99 g, 10.0 mol) was added to methanol (200 mL), Pd/C (200 mg) was added, and the mixture solution underwent hydrogenation for 16 hrs. After suction filtration of the reaction solution, the filtrate was concentrated to obtain the title compound (1.68 g, yield: 99.4%).

2. Preparation of methyl 2-amino-4-fluorobenzo[d]thiazole-6-carboxylate

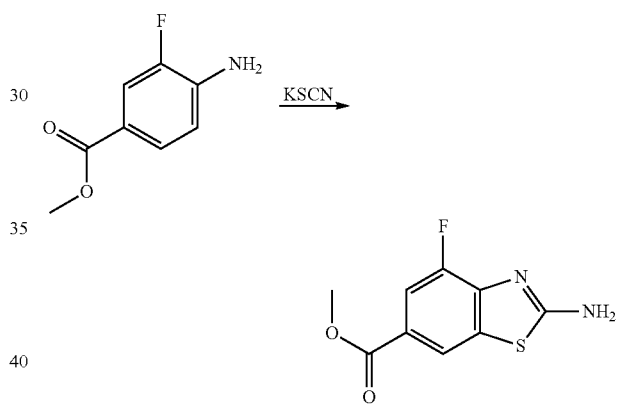

Methyl 4-amino-3-fluorobenzoate (1.68 g, 9.9 mmol) and KSCN (3.84 g, 39.6 mmol) were added to glacial acetic acid (20 mL), and 15 mins later, bromine (1.58 g, 9.9 mmol) was added. The mixture solution reacted at 25° C. for 16 hrs. Water (100 mL) was added, and the pH of the reaction solution was adjusted to 8 with ammonium hydroxide. After suction filtration, the solid was dried to obtain a crude title compound (2.30 g), which would be directly used in the next step.

3. Preparation of methyl 2-bromo-4-fluorobenzo[d]thiazole-6-carboxylate

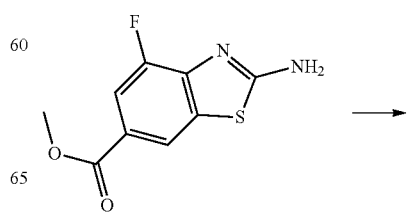

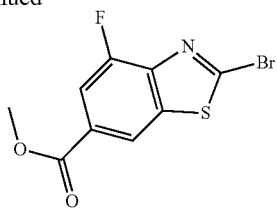

Crude methyl 2-amino-4-fluorobenzo[d]thiazole-6-carboxylate (2.30 g, 9.9 mmol) and copper bromide (3.31 g, 14.9 mmol) were added to acetonitrile (20 mL). Tert-butyl nitrite (1.53 g, 14.9 mmol) was added dropwise at 0° C., and after the addition was completed, the mixture solution was stirred and reacted at 25° C. for 1 hr. The reaction solution was concentrated directly, and purified by silica-gel column chromatography (petroleum ether:ethyl acetate=10:1) to obtain the title compound (480 mg, two-step total yield: 16.7%).

4. Preparation of methyl 2-((1RS, 4RS, 5SR)-5-((5-cyclopropyl-3-(2,6-dichlorophenyl) isoxazol-4-yl)methoxy)-2-azabicyclo[2.2.1]heptan-2-yl)-4-fluorobenzo[d]thiazole-6-carboxylate

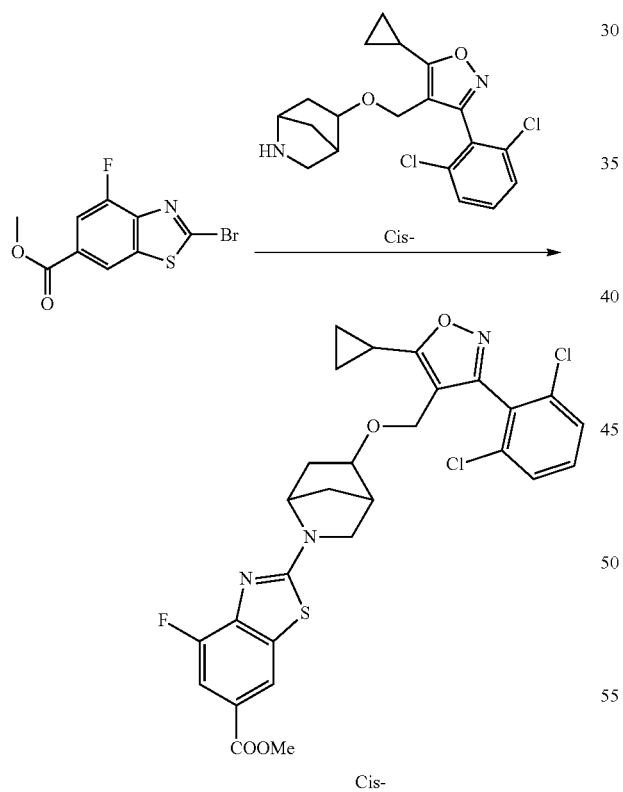

Methyl 2-bromo-4-fluorobenzo[d]thiazole-6-carboxylate (151 mg, 0.52 mmol), 4-((((1RS, 4RS, 5SR)-2-azabicyclo[2.2.1]heptan-5-yl)oxy)methyl)-5-cyclopropyl-3-(2,6-dichlorophenyl)isoxazole (100 mg, 0.26 mmol) and cesium carbonate (254 mg, 0.78 mmol) were added to DMA (2 mL), and the mixture solution reacted at 110° C. for 16 hrs. Water (50 mL) and ethyl acetate (50 mL) were added for extraction, and the organic phase was concentrated, and purified by silica-gel column chromatography (petroleum ether:ethyl acetate=8:1) to obtain the title compound (50 mg, yield: 32.3%).

5. Preparation of 2-((1RS, 4RS, 5SR)-5-((5-cyclopropyl-3-(2,6-dichlorophenyl) isoxazol-4-yl)methoxy)-2-azabicyclo[2.2.1]heptan-2-yl)-4-fluorobenzo[d]thiazole-6-carboxylic acid

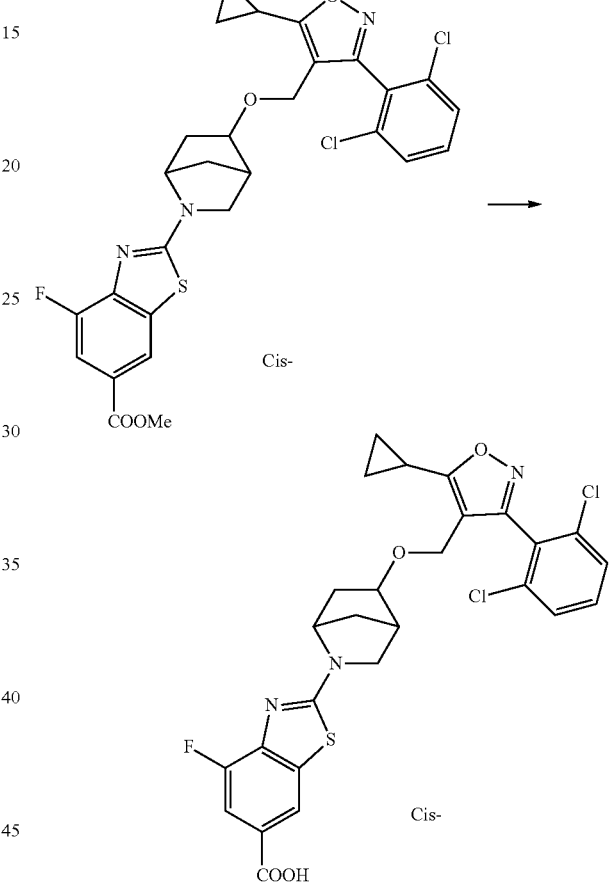

Methyl 2-((1RS,4RS,5SR)-5-((5-cyclopropyl-3-(2,6-dichlorophenyl)isoxazol-4-yl) methoxy)-2-azabicyclo[2.2.1]heptan-2-yl)-4-fluorobenzo[d]thiazole-6-carboxylate (50 mg, 0.09 mmol) was dissolved into the mixed solution of THF (2 mL) and methanol (2 mL), and 1 M lithium hydroxide (0.9 mL) was then added. The mixture solution was stirred and reacted at 40° C. for 1 hr, and the pH of the reaction solution was then adjusted to 4 with 1 M hydrochloric acid. Ethyl acetate (30 mL) was added for extraction, and the organic phase was concentrated, and purified by silica gel column chromatography (dichloromethane:methanol=15:1) to obtain the title compound (30 mg, yield: 61.5%).

Molecular formula: $C_{27}H_{22}Cl_2FN_3O_4S$ Molecular weight: 573.1 LC-MS (m/z): 574.1 (M+H+)

$^1$H-NMR (400 MHz, DMSO-d6) δ 8.18 (s, 1H), 7.76-7.48 (m, 4H), 4.32-4.20 (m, 2H), 3.65-3.58 (m, 1H), 3.45-3.40 (m, 2H), 2.58-2.52 (m, 1H), 2.40-2.28 (m, 1H), 1.95-1.85

(m, 1H), 1.65-1.55 (m, 1H), 1.53-1.42 (m, 1H), 1.20-1.13 (m, 2H), 1.13-1.09 (m, 2H), 0.90-0.78 (m, 2H).

Example 5: Preparation of 2-((1RS, 4RS, 5SR)-5-((5-cyclopropyl-3-(2,6-dichlorophenyl) isoxazol-4-yl)methoxy)-2-azabicyclo[2.2.1]heptan-2-yl)-4-methylbenzo[d]thiazole-6-carboxylic acid (compound 5)

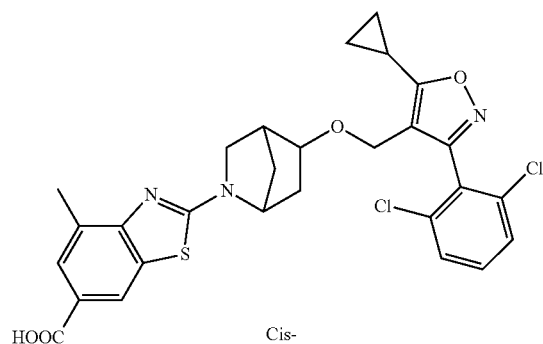 [SMILES: Cc1cc(C(=O)O)cc2sc(N3CC4CC3CC4OCc3c(-c4c(Cl)cccc4Cl)noc3C3CC3)nc12]

1. Preparation of methyl 2-amino-4-methylbenzo[d]thiazole-6-carboxylate

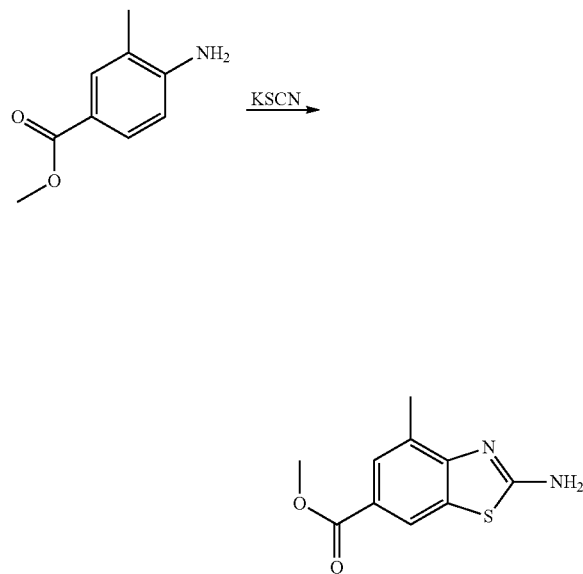

Methyl 4-amino-3-methylbenzoate (33.0 g, 0.2 mol) and KSCN (68.0 g, 0.7 mol) were added to glacial acetic acid (200 mL) at 0° C., and bromine (31.9 g, 0.2 mol) was slowly added dropwise at 0° C. After the dropwise addition was completed, the mixture solution was heated to 25° C. and reacted for 10 hrs. The reaction solution was then poured into an ice water, and pH of the solution was adjusted to 8 with ammonium hydroxide. A solid was precipitated, filtered out under reduced pressure, and dried. The resulted solid would be directly used in the next step.

2. Preparation of methyl 2-bromo-4-methylbenzo[d]thiazole-6-carboxylate

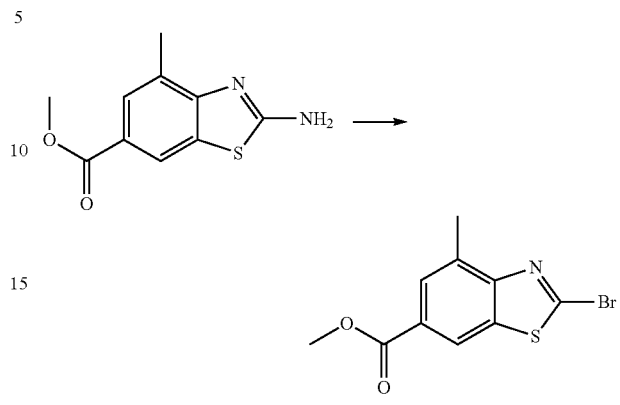

Methyl 2-amino-4-methylbenzo[d]thiazole-6-carboxylate (44.5 g, 0.20 mol) and copper bromide (75.9 g, 0.34 mol) were dissolved into acetonitrile (300 mL) at 0° C., and tert-butyl nitrite (24.7 g, 0.24 mol) was slowly added dropwise. After the dropwise addition was completed, the mixture solution was stirred and reacted at 25° C. for 3 hrs. The reaction solution was poured into an ice water, and the solid was precipitated and filtered out under reduced pressure. The filter cake was washed with a mixed solvent (PE:EA=5:1, 600 mL), and the filtrate was concentrated to obtain the target product (34.3 g, two-step yield: 60.0%).

3. Preparation of 4-((((1RS, 4RS, 5SR)-2-azabicyclo[2.2.1]heptan-5-yl)oxy)methyl)-5-cyclopropyl-3-(2,6-dichlorophenyl)isoxazole

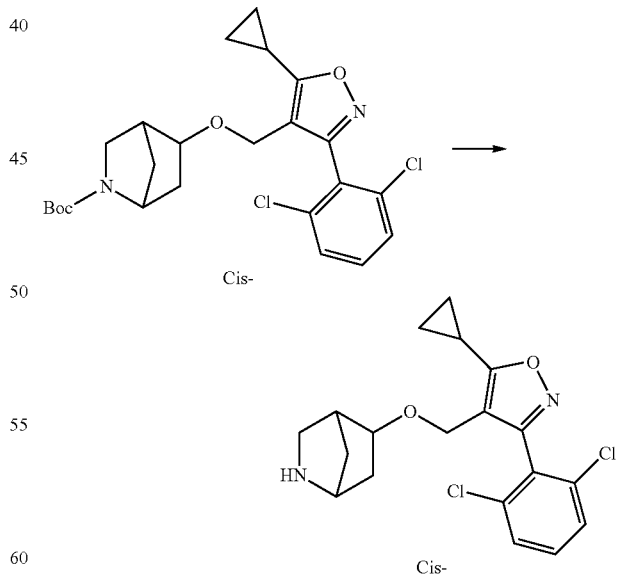

Tert-butyl (1RS, 4RS, 5SR)-5-((5-cyclopropyl-3-(2,6-dichlorophenyl)isoxazol-4-yl) methoxy)-2-azabicyclo[2.2.1]heptane-2-carboxylate (200 mg, 0.42 mmol) was added to dichloromethane (20 mL), and trifluoroacetic acid (10 mL) was then added. The mixture solution reacted at 25° C. for 2 hrs, and then the reaction solution was concentrated and directly used in the next step.

4. Preparation of methyl 2-((1RS, 4RS, 5SR)-5-((5-cyclopropyl-3-(2,6-dichlorophenyl) isoxazol-4-yl) methoxy)-2-azabicyclo[2.2.1]heptan-2-yl)-4-methyl-benzo[d]thiazol-6-carboxylate

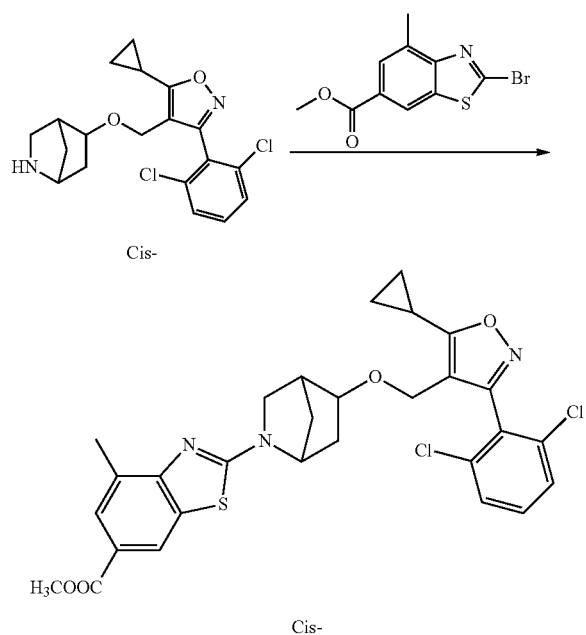

Methyl 2-bromo-4-methylbenzo[d]thiazole-6-carboxylate (120 mg, 0.42 mmol), 4-((((1RS, 4RS, 5SR)-2-azabicyclo[2.2.1]heptan-5-yl)oxy)methyl)-5-cyclopropyl-3-(2,6-dichlorophenyl)isoxazole (160 mg, 0.42 mmol) and cesium carbonate (410 mg, 1.26 mmol) were added to acetonitrile (30 mL), and the mixture solution reacted at 90° C. for 10 hrs. The reaction solution was cooled and filtrated, and the filtrate was concentrated, and purified by silica-gel column chromatography (PE:EA=3:1) to obtain the title compound (45 mg, two-step yield: 18.4%).

5. Preparation of 2-((1RS, 4RS, 5SR)-5-((5-cyclopropyl-3-(2,6-dichlorophenyl) isoxazol-4-yl) methoxy)-2-azabicyclo[2.2.1]heptan-2-yl)-4-methyl-benzo[d]thiazole-6-carboxylic acid

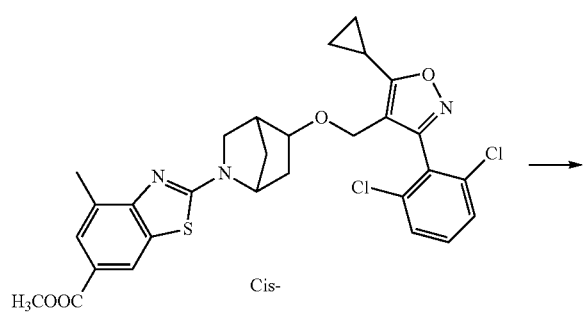

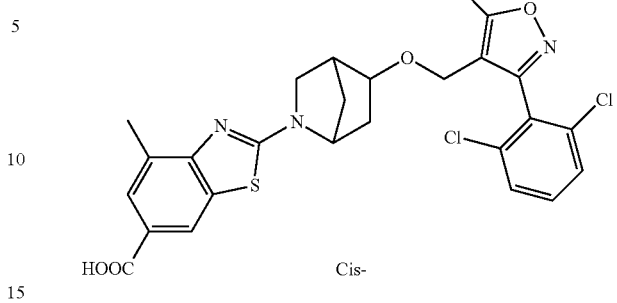

Methyl 2-((1RS, 4RS, 5SR)-5-((5-cyclopropyl-3-(2,6-dichlorophenyl)isoxazol-4-yl) methoxy)-2-azabicyclo[2.2.1]heptan-2-yl)-4-methylbenzo[d]thiazol-6-carboxylate (45 mg, 0.077 mmol) and lithium hydroxide monohydrate (16 mg, 0.38 mmol) were added to the mixed solution of methanol (8 mL), THF (8 mL) and water (4 mL), and the mixture solution reacted at 25° C. for 5 hrs. The pH of the reaction solution was adjusted to 5 with dilute hydrochloric acid, and the resulted solution was then concentrated to obtain the target product (34 mg, yield: 77.4%).

Molecular formula: $C_{28}H_{25}C_2N_3O_4S$ Molecular weight: 569.1 LC-MS (m/z): 570.2 (M+H+)

$^1$H NMR (400 MHz, CDCl$_3$) δ: 8.19 (s, 1H), 7.84 (s, 1H), 7.56-7.50 (m, 3H), 4.36 (s, 2H), 3.63-3.48 (m, 2H), 3.17-3.08 (m, 1H), 2.69-2.62 (m, 1H), 2.55 (s, 3H), 2.48-2.35 (m, 1H), 2.15-2.03 (m, 2H), 1.75-1.68 (m, 1H), 1.49-1.46 (m, 1H), 1.40-1.32 (m, 2H), 1.18-1.21 (m, 2H)

Example 6: Preparation of 2-((1RS, 4SR, 6RS)-6-((5-cyclopropyl-3-(2,6-dichlorophenyl) isoxazol-4-yl)methoxy)-2-azabicyclo[2.2.1]heptan-2-yl)benzo[d]thiazole-6-carboxylic acid (compound 6)

1. Preparation of tert-butyl (1RS, 4SR, 6RS)-6-hydroxy-2-azabicyclo[2.2.1]heptane-2-carboxylate

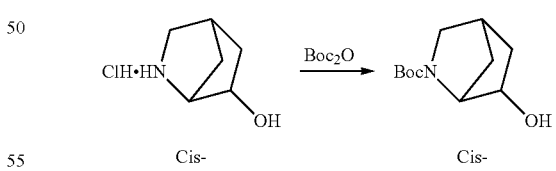

(1RS, 4SR, 6RS)-2-azabicyclo[2.2.1]heptan-6-ol hydrochloride (0.5 g, 3.3 mmol) was dissolved into dichloromethane (20 mL), and di-tert-butyl dicarbonate (0.73 g, 3.3 mmol) and triethylamine (0.37 g, 3.7 mmol) were added. The mixture solution reacted at 25° C. for 3 hrs. The solvent was distilled out in spin-dry manner, and the residue was purified by column chromatography (petroleum ether:ethyl acetate=2:1) to obtain the target compound (0.65 g, yield: 91.5%).

2. Preparation of tert-butyl (1RS, 4SR, 6RS)-6-((5-cyclopropyl-3-(2,6-dichlorophenyl) isoxazol-4-yl)methoxy)-2-azabicyclo[2.2.1]heptane-2-carboxylate

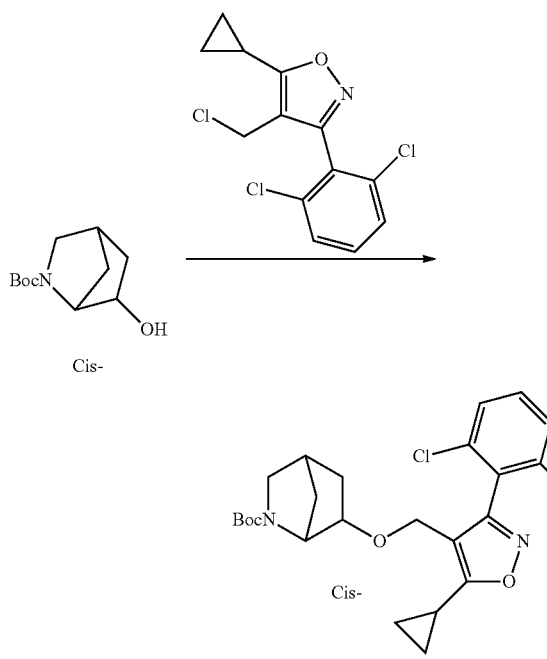

Tert-butyl (1RS, 4SR, 6RS)-6-hydroxy-2-azabicyclo[2.2.1]heptane-2-carboxylate (0.1 g, 0.47 mmol), 4-(chloromethyl)-5-cyclopropyl-3-(2,6-dichlorophenyl)isoxazole (0.21 g, 0.69 mmol), potassium tert-butoxide (79 mg, 0.70 mmol), 18-crown-6 (0.15 g, 0.57 mmol) and potassium iodide (0.12 g, 0.72 mmol) were dissolved into tetrahydrofuran (10 mL), and the mixture solution was heated to 60° C. and reacted for 3 hrs with stirring. Water (20 mL) and ethyl acetate (20 mL) were added for extraction, and the water phase was extracted with ethyl acetate (20 mL×3). The organic phases were combined, dried over anhydrous sodium sulfate, and filtrated. The filtrate was concentrated, and the resulted crude product was purified by silica-gel column chromatography (petroleum ether:ethyl acetate=5:1) to obtain the compound (0.2 g, yield: 90.9%).

3. Preparation of 4-((((1RS, 4SR, 6RS)-2-azabicyclo[2.2.1]heptan-6-yl)oxy) methyl)-5-cyclopropyl-3-(2,6-dichlorophenyl)isoxazole

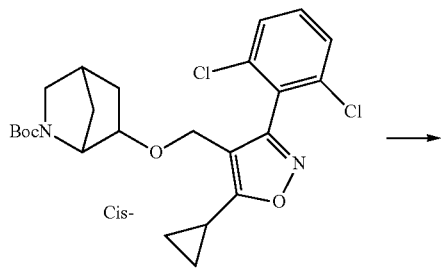

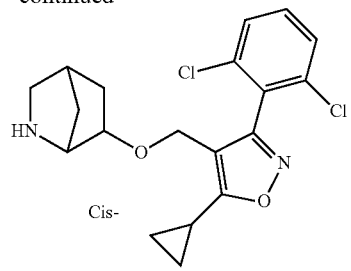

Tert-butyl (1RS, 4SR, 6RS)-6-((5-cyclopropyl-3-(2,6-dichlorophenyl)isoxazol-4-yl)methoxy)-2-azabicyclo[2.2.1]heptane-2-carboxylate (0.20 g, 0.42 mmol) was dissolved into dichloromethane (2 mL), and a solution (2 mL) of hydrochloric acid in ethanol was added after the mixture solution was cooled to 0° C. The resulted mixture solution reacted for 3 hrs. The pH of the reaction system was adjusted to 7 to 8 with a saturated sodium bicarbonate solution, and the reaction solution was then extracted with dichloromethane (10 mL×2). The organic phase was dried over anhydrous sodium sulfate and filtrated, and the filtrate was concentrated to obtain a crude compound (0.158 g, yield: 100%) which would be directly used in the next step.

4. Preparation of methyl 2-((1RS, 4SR, 6RS)-6-((5-cyclopropyl-3-(2,6-dichlorophenyl) isoxazol-4-yl)methoxy)-2-azabicyclo[2.2.1]heptan-2-yl)benzo[d]thiazole-6-carboxylate

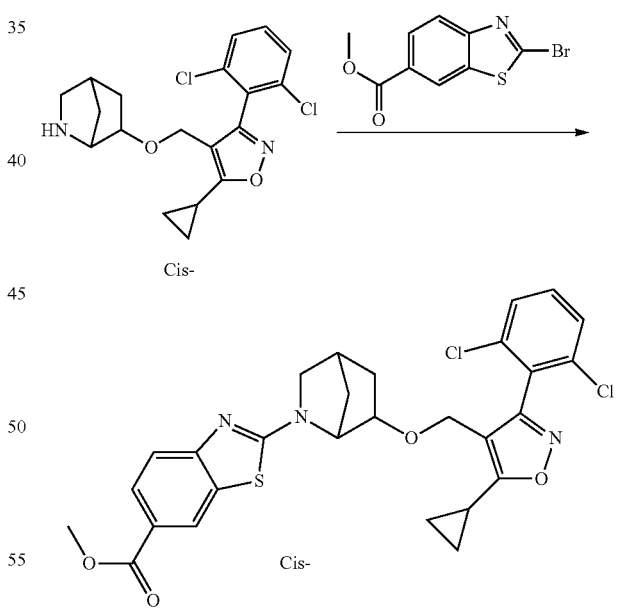

4-((((1RS,4SR,6RS)-2-azabicyclo[2.2.1]heptan-6-yl)oxy)methyl)-5-cyclopropyl-3-(2,6-dichlorophenyl)isoxazole (0.158 g, 0.42 mmol) was dissolved into N,N-dimethylacetamide (3 mL), and then methyl 2-bromobenzo[d]thiazole-6-carboxylate (0.23 g, 0.84 mmol) and cesium carbonate (0.41 g, 1.3 mmol) were added. The mixture solution was heated to 100° C. under microwave, and reacted for 30 mins. Water (30 mL) were added, and the solution was extracted with ethyl acetate (20 mL×2). The organic phases were combined, dried over anhydrous sodium sulfate, and filtrated. The filtrate was concentrated, and the resulted crude product was purified by silica-gel column chromatography (petroleum ether:ethyl acetate=2:1) to obtain the compound (0.15 g, yield: 62.5%).

5. Preparation of 2-((1RS, 4SR, 6RS)-6-((5-cyclopropyl-3-(2,6-dichlorophenyl)isoxazol-4-yl)methoxy)-2-azabicyclo[2.2.1]heptan-2-yl)benzo[d]thiazole-6-carboxylicacid

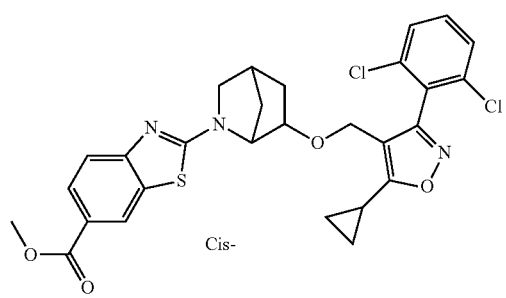 [SMILES: O=C(O)c1ccc2nc(N3CC4CC(OCc5c(-c6c(Cl)cccc6Cl)noc5C5CC5)C3C4)sc2c1]

Methyl 2-((1RS, 4SR, 6RS)-6-((5-cyclopropyl-3-(2,6-dichlorophenyl)isoxazol-4-yl) methoxy)-2-azabicyclo[2.2.1] heptan-2-yl)benzo[d]thiazole-6-carboxylate (0.15 g, 0.26 mmol) was dissolved into the mixed solution of tetrahydrofuran (2 mL) and methanol (2 mL), and a solution of sodium hydroxide (52 mg, 1.3 mmol) in water (1 mL) was added. The mixture solution was stirred and reacted at 60° C. for 3 hrs. The pH of the reaction system was adjusted to 3 to 4 with 1 N hydrochloric acid. Water (10 mL) was added, and the solution was extracted with ethyl acetate (10 mL×2). The organic phases were combined, dried over anhydrous sodium sulfate, and filtrated. The filtrate was concentrated, and the resulted crude product was purified by silica-gel column chromatography (dichloromethane:methanol=20:1) to obtain the compound (0.11 g, yield: 73.3%).

Molecular formula: $C_{27}H_{23}Cl_2N_3O_4S$ Molecular weight: 555.1 LC-MS (m/z): 556.1 (M+H+)

$^1$H-NMR (400 MHz, MeOD) δ: 8.33 (s, 1H), 7.98 (dd, $J_1$=8.8 Hz, $J_2$=1.6 Hz, 1H), 7.49-7.51 (m, 2H), 7.41-7.46 (m, 2H), 4.38-4.47 (m, 2H), 3.57-3.58 (m, 1H), 3.42-3.44 (m, 1H), 2.95-3.01 (m, 1H), 2.62-2.65 (m, 1H), 2.32-2.36 (m, 1H), 1.75-1.79 (m, 1H), 1.61-1.69 (m, 2H), 1.33-1.36 (m, 1H), 1.07-1.19 (m, 4H)

Example 7: Preparation of 2-((1RS, 4SR, 6SR)-6-((5-cyclopropyl-3-(2,6-dichlorophenyl) isoxazol-4-yl)methoxy)-2-azabicyclo[2.2.1]heptan-2-yl)benzo[d]thiazole-6-carboxylic acid (compound 7)

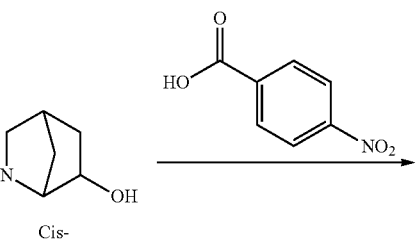

1. Preparation of tert-butyl (1RS, 4SR, 6SR)-6-((4-nitrobenzoyl)oxy)-2-azabicyclo[2.2.1]heptane-2-carboxylate

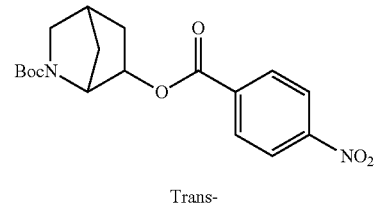

Tert-butyl (1RS, 4SR, 6RS)-6-hydroxy-2-azabicyclo[2.2.1]heptane-2-carboxylate (0.2 g, 0.94 mmol), p-nitrobenzoic acid (0.172 g, 1.03 mmol), diethyl azodicarboxylate (0.24 g, 1.38 mmol) and triphenylphosphine (0.37 g, 1.41 mmol) were dissolved into tetrahydrofuran (10 mL), and the mixture solution reacted at 25° C. for 3 hrs. The solvent was distilled out in spin-dry manner, and the resulted crude product was purified by silica-gel column chromatography (petroleum ether:ethyl acetate=5:1) to obtain the target product (0.32 g, yield: 94.1%).

2. Preparation of tert-butyl (1RS, 4SR, 6SR)-6-hydroxy-2-azabicyclo[2.2.1]heptane-2-carboxylate

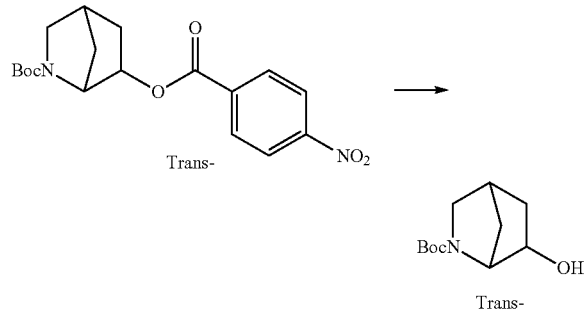

Tert-butyl (1RS, 4SR, 6SR)-6-((4-nitrobenzoyl)oxy)-2-azabicyclo[2.2.1]heptane-2-carboxylate (0.32 g, 0.88 mmol) and potassium hydroxide (0.5 g, 8.9 mmol) were dissolved into the mixed solvent of tetrahydrofuran (30 mL) and water (3 mL), and the mixture solution was stirred and reacted at 25° C. for 16 hrs. The solvent was distilled out in spin-dry manner, and the resulted crude product was purified by silica-gel column chromatography (petroleum ether:ethyl acetate=2:1) to obtain the target product (0.13 g, yield: 68.4%).

3. Preparation of tert-butyl (1RS, 4SR, 6SR)-6-((5-cyclopropyl-3-(2,6-dichlorophenyl) isoxazol-4-yl) methoxy)-2-azabicyclo[2.2.1]heptane-2-carboxylate

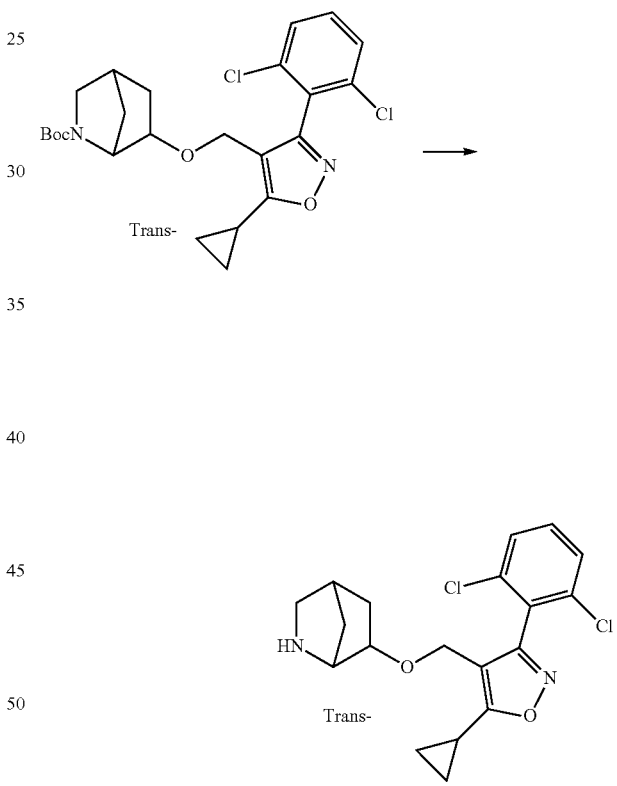

Tert-butyl (1RS, 4SR, 6SR)-6-hydroxy-2-azabicyclo[2.2.1]heptane-2-carboxylate (0.13 g, 0.61 mmol), 4-(chloromethyl)-5-cyclopropyl-3-(2,6-dichlorophenyl)isoxazole (0.28 g, 0.92 mmol), potassium tert-butoxide (0.1 g, 0.89 mmol), 18-crown-6 (0.2 g, 0.76 mmol) and potassium iodide (0.15 g, 0.90 mmol) were dissolved into tetrahydrofuran (20 mL), and the mixture solution was heated to 60° C. and reacted for 3 hrs with stirring. Water (20 mL) and ethyl acetate (20 mL) were added for extraction, and the water phase was extracted with ethyl acetate (20 mL×3). The organic phases were combined, dried over anhydrous sodium sulfate, and filtrated. The filtrate was concentrated, and the resulted crude product was purified by silica-gel column chromatography (petroleum ether:ethyl acetate=5:1) to obtain the target product (0.25 g, yield: 86.2%).

4. Preparation of 4-((((1RS, 4SR, 6SR)-2-azabicyclo[2.2.1]heptan-6-yl)oxy)methyl)-5-cyclopropyl-3-(2,6-dichlorophenyl)isoxazole

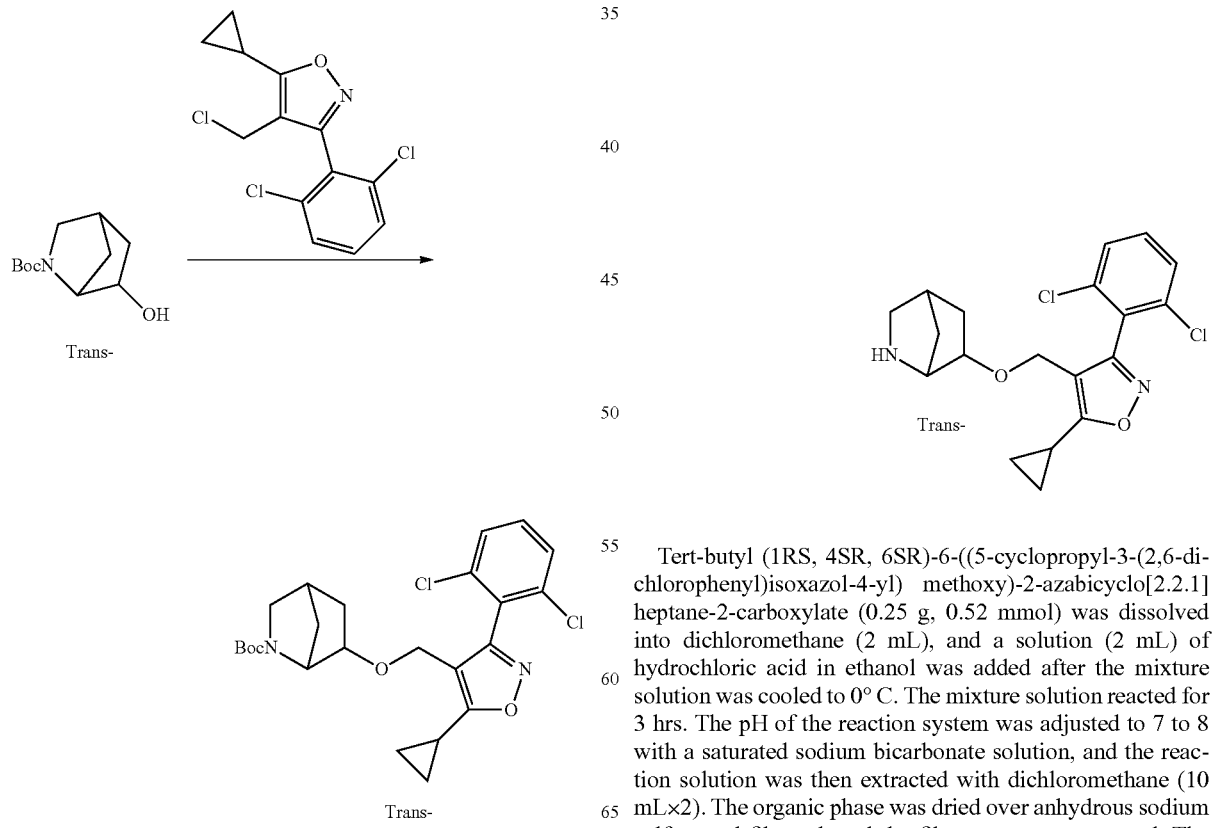

Tert-butyl (1RS, 4SR, 6SR)-6-((5-cyclopropyl-3-(2,6-dichlorophenyl)isoxazol-4-yl) methoxy)-2-azabicyclo[2.2.1]heptane-2-carboxylate (0.25 g, 0.52 mmol) was dissolved into dichloromethane (2 mL), and a solution (2 mL) of hydrochloric acid in ethanol was added after the mixture solution was cooled to 0° C. The mixture solution reacted for 3 hrs. The pH of the reaction system was adjusted to 7 to 8 with a saturated sodium bicarbonate solution, and the reaction solution was then extracted with dichloromethane (10 mL×2). The organic phase was dried over anhydrous sodium sulfate and filtrated, and the filtrate was concentrated. The residue would be directly used in the next step.

5. Preparation of methyl 2-((1RS, 4SR, 6SR)-6-((5-cyclopropyl-3-(2,6-dichlorophenyl) isoxazol-4-yl)methoxy)-2-azabicyclo[2.2.1]heptan-2-yl)benzo[d]thiazole-6-carboxylate

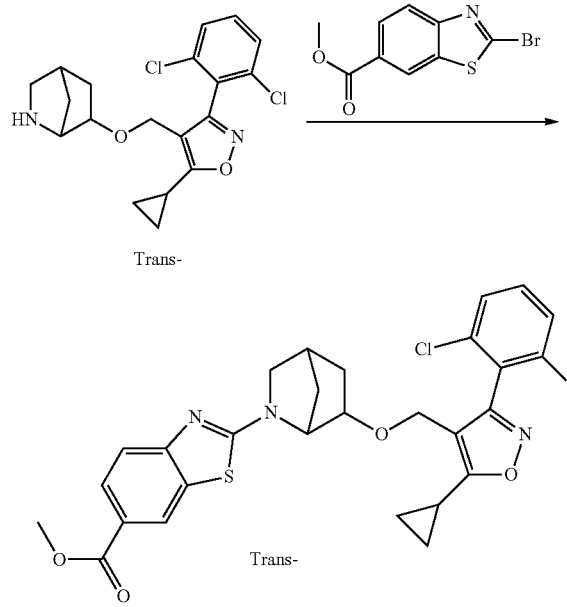

4-((((1RS, 4SR, 6SR)-2-azabicyclo[2.2.1]heptan-6-yl)oxy)methyl)-5-cyclopropyl-3-(2,6-dichlorophenyl)isoxazole (crude product from the last step, 0.52 mmol) was dissolved into N,N-dimethylacetamide (3 mL), and then methyl 2-bromobenzo[d]thiazole-6-carboxylate (0.28 g, 1.0 mmol) and cesium carbonate (0.51 g, 1.6 mmol) were added. The mixture solution was heated to 100° C. under microwave, and reacted for 30 mins. Water (30 mL) was added, and the solution was extracted with ethyl acetate (20 mL×2). The organic phases were combined, dried over anhydrous sodium sulfate, and filtrated. The filtrate was concentrated, and the resulted crude product was purified by silica-gel column chromatography (petroleum ether:ethyl acetate=2:1) to obtain the target product (0.24 g, yield: 80.0%).

6. Preparation of 2-((1RS, 4SR, 6SR)-6-((5-cyclopropyl-3-(2,6-dichlorophenyl) isoxazol-4-yl)methoxy)-2-azabicyclo[2.2.1]heptan-2-yl)benzo[d]thiazole-6-carboxylicacid

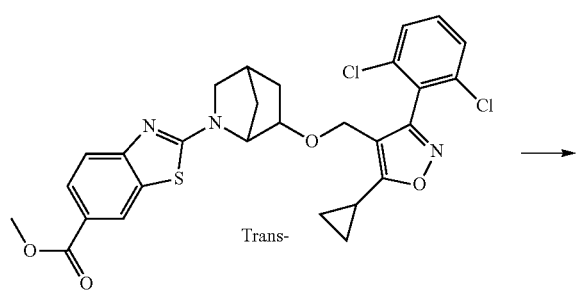

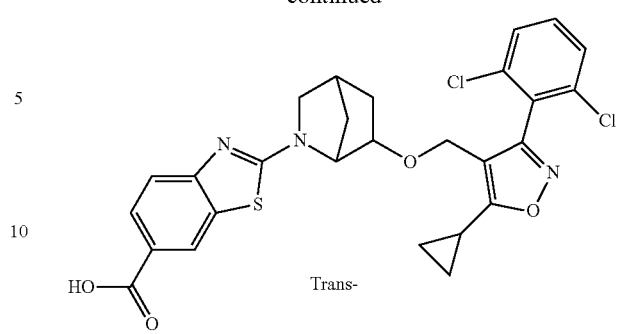

Methyl 2-((1RS,4SR,6SR)-6-((5-cyclopropyl-3-(2,6-dichlorophenyl)isoxazol-4-yl)methoxy)-2-azabicyclo[2.2.1]heptan-2-yl)benzo[d]thiazole-6-carboxylate (0.24 g, 0.42 mmol) was dissolved into the mixed solution of tetrahydrofuran (2 mL) and methanol (2 mL), and a solution of sodium hydroxide (80 mg, 2.0 mmol) in water (1 mL) was added. The mixture solution was stirred and reacted at 60° C. for 3 hrs. The pH of the reaction solution was adjusted to 3 to 4 with 1 N hydrochloric acid, and water (10 mL) was added. The solution was extracted with ethyl acetate (10 mL×2). The organic phases were combined, dried over anhydrous sodium sulfate, and filtrated. The filtrate was concentrated, and the resulted crude product was purified by silica-gel column chromatography (dichloromethane:methanol=20:1) to obtain the target product (0.13 g, yield: 56.5%).

Molecular formula: $C_{27}H_{23}C_2N_3O_4S$ Molecular weight: 555.1 LC-MS (m/z): 556.1 (M+H+)

$^1$H-NMR (400 MHz, MeOD) δ: 8.33 (s, 1H), 7.98 (dd, $J_1$=8.8 Hz, $J_2$=1.6 Hz, 1H), 7.49-7.51 (m, 2H), 7.41-7.46 (m, 2H), 4.39-4.47 (m, 2H), 3.57-3.59 (m, 1H), 3.43-3.45 (m, 1H), 2.95-3.01 (m, 1H), 2.62-2.65 (m, 1H), 2.32-2.36 (m, 1H), 1.75-1.79 (m, 1H), 1.61-1.69 (m, 2H), 1.33-1.36 (m, 1H), 1.07-1.20 (m, 4H)

Example 8: Preparation of 2-((1S, 4S, 5R)-5-((5-cyclopropyl-3-(2-(trifluoromethoxy) phenyl)isoxazol-4-yl)methoxy)-2-azabicyclo[2.2.1]heptan-2-yl)-4-fluorobenzo[d]thiazole-6-formic acid (compound 8)

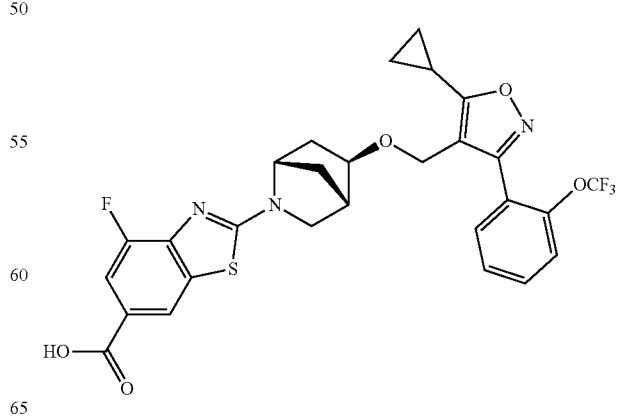

1. Preparation of methyl 4-amino-3-fluorobenzoate

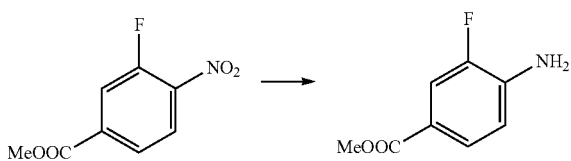 [SMILES: COC(=O)c1ccc([N+](=O)[O-])c(F)c1 ; COC(=O)c1ccc(N)c(F)c1]

Methyl 3-fluoro-4-nitrobenzoate (3.0 g, 15.1 mmol) was dissolved into MeOH (50 mL), and Pd/C (1.2 g) was added at an $N_2$ atmosphere. The mixture solution underwent hydrogenation at 25° C. for 3 hrs. Pd/C was filtered off through celite, and the residue was concentrated to obtain the product (2.5 g, yield: 98.0%).

2. Preparation of methyl 2-amino-4-fluorobenzo[d]thiazole-6-formate

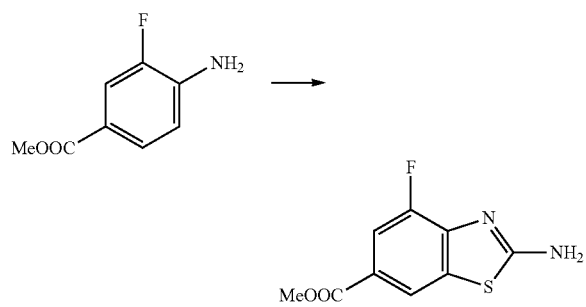

Methyl 4-amino-3-fluorobenzoate (2.5 g, 14.8 mmol) and KSCN (5.7 g, 59.1 mmol) were dissolved into glacial acetic acid (50 mL), and the solution was stirred at 25° C. for 15 mins. Then bromine (2.4 g, 14.9 mmol) was added dropwise, and the mixture solution continued to react at 25° C. for 16 hrs. The reaction solution was filtrated, and the filtrate was diluted with water (50 mL). The pH of the filtrate was adjusted to 8 with ammonium hydroxide. Then the resulted solution was filtrated, and the filter cake was purified by silica-gel column chromatography (petroleum ether:ethyl acetate=5:1) to obtain the product (200 mg, yield: 6.0%).

3. Preparation of methyl 2-bromo-4-fluorobenzo[d]thiazole-6-formate

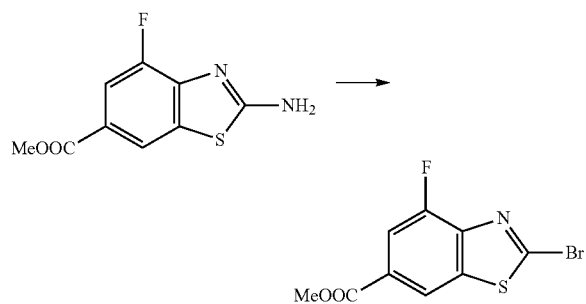

Methyl 2-amino-4-fluorobenzo[d]thiazole-6-formate (200 mg, 0.88 mmol) and $CuBr_2$ (395 mg, 1.77 mmol) were dissolved into acetonitrile (10 mL), and tert-butyl nitrite (182 mg, 1.77 mmol) was added dropwise at 0° C. After the addition was completed, the mixture solution reacted at 25° C. for 1 hr. The reaction solution was diluted with EA (50 mL), washed with water (50 mL×3), dried and concentrated. The residue was purified by silica-gel column chromatography (petroleum ether:ethyl acetate=5:1) to obtain a product (230 mg, yield: 89.7%).

4. Preparation of (E)-2-trifluoromethoxybenzaldoxime

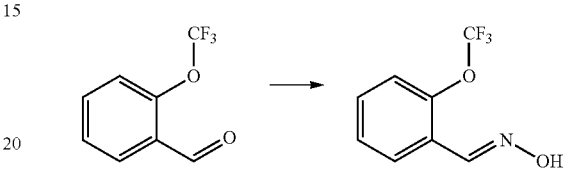

Hydroxylamine hydrochloride (5.88 g, 84.7 mmol) was dissolved in water (60 mL), and the solution was stirred at 0° C. NaOH (3.5 g, 87.6 mmol) was dissolved in water (60 mL), and then added dropwise to the reaction flask. 2-trifluoromethoxybenzaldehyde (14 g, 73.6 mmol) was dissolved in an anhydrous ethanol solution (60 mL), and then added dropwise to the reaction flask. After the addition was completed, the mixture solution reacted at 25° C. for 1 hr. The reaction solution was diluted with water (300 mL), and extracted with ethyl acetate (500 mL×3). The organic phases were combined, dried and concentrated to obtain the crude product (15.4 g).

5. Preparation of N-hydroxy-2-(trifluoromethoxy)benzimidoyl chloride

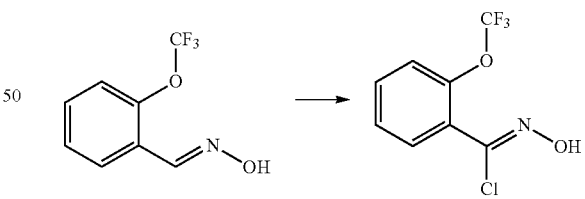

(E)-2-trifluoromethoxybenzaldoxime (15.4 g, crude product) was dissolved in DMF (150 mL), and NCS (11.23 g, 84.1 mmol) was then added in batches at a temperature not higher than 25° C. After the addition was completed, the mixture solution reacted at 25° C. for 1 hr. The reaction solution was diluted with water (150 mL), and extracted with ethyl acetate (500 mL×3). The organic phases were combined, dried over anhydrous sodium sulfate, and concentrated to obtain the crude product (16.6 g).

6. Preparation of methyl 5-cyclopropyl-3-(2-(trifluoromethoxy)phenyl)isoxazol-4-formate

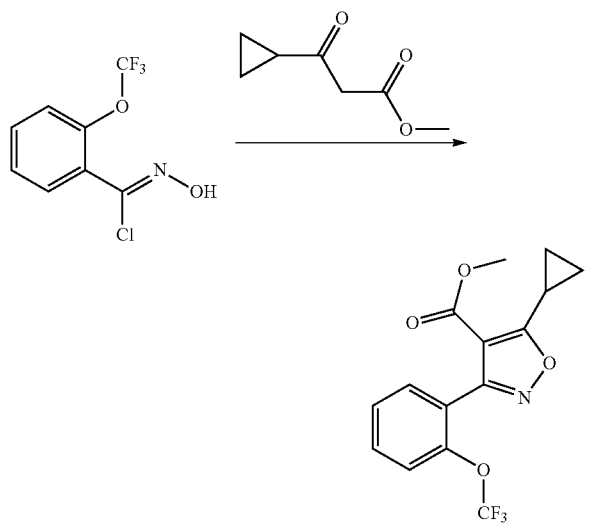

Potassium carbonate (10.44 g, 75.52 mmol) was added to THF (100 mL), and the solution of methyl 3-cyclopropyl-3-oxopropionate (10.44 g, 73.4 mmol) in THF (50 mL) was added to the reaction system. The system was stirred at −10° C. for 30 mins. The solution of N-hydroxy-2-(trifluoromethoxy)benzimidoyl chloride (16.6 g, crude product) in THF (50 mL) was then added to the reaction system at −5° C., and the system reacted at 35° C. for 6 hrs. The reaction solution was diluted with water (200 mL), and extracted with ethyl acetate (500 mL×3). The organic phase was dried, concentrated, and purified by a silica-gel column (petroleum ether:ethyl acetate=5:1) to obtain a product (11.3 g, yield: 47.1%).

7. Preparation of (5-cyclopropyl-3-(2-(trifluoromethoxy)phenyl)isoxazol-4-yl)-methanol

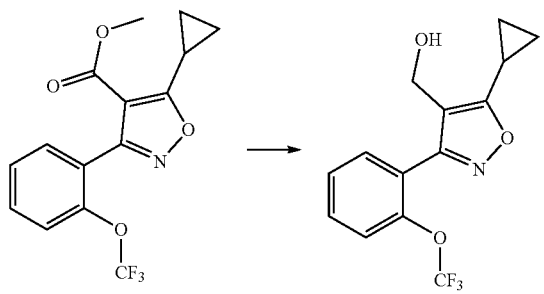 [SMILES: COC(=O)c1c(-c2ccccc2OC(F)(F)F)noc1C1CC1 ; OCc1c(-c2ccccc2OC(F)(F)F)noc1C1CC1]

Methyl 5-cyclopropyl-3-(2-(trifluoromethoxy)phenyl) isoxazol-4-formate (2.4 g, 7.33 mmol) was dissolved into anhydrous THF (50 mL), and DIBAL-H (1.5 M methylbenzene solution, 15 mL) was added dropwise at 0° C. After the addition was completed, the mixture solution reacted at 25° C. for 2 hrs. MeOH (2 mL) was added dropwise to the reaction system at 0° C. for quenching, and water (50 mL) and ethyl acetate (100 mL) were then added. The resulted solution was filtrated through celite, the filtrate was then separated by standing, and the water phase was extracted with ethyl acetate (100 mL×2). The organic phases were combined, dried, concentrated, and purified by silica-gel column chromatography (petroleum ether:ethyl acetate=5:1) to obtain a product (1.0 g, yield: 45.6%).

8. Preparation of 4-(bromomethyl)-5-cyclopropyl-3-(2-(trifluoromethoxy)phenyl) isoxazole

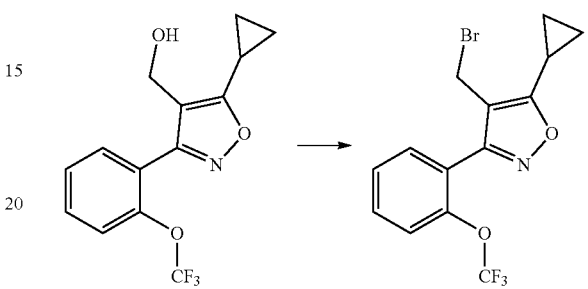

(5-cyclopropyl-3-(2-(trifluoromethoxy)phenyl)isoxazol-4-yl)-methanol (1 g, 3.34 mmol) was dissolved into dichloromethane (20 mL), and triphenylphosphine (1.31 g, 5.01 mmol) was added. Carbon tetrabromide (1.66 g, 5.07 mmol) was added in batches at 0° C., and after the addition was completed, the mixture solution reacted at 25° C. for 2 hrs. The reaction solution was concentrated, and purified by a silica-gel column (petroleum ether:ethyl acetate=10:1) to obtain a product (860 mg, yield: 72.0%).

9. Preparation of tert-butyl (1S, 4S, 5R)-5-((5-cyclopropyl-3-(2-(trifluoromethoxy) phenyl)isoxazol-4-yl)methoxy)-2-azabicyclo[2.2.1]heptane-2-formate

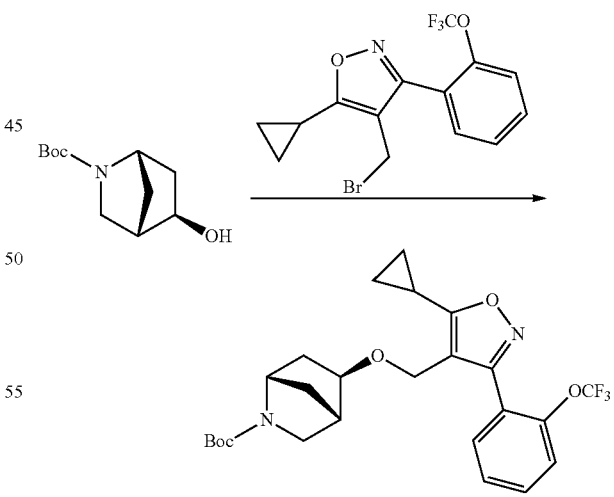

Tert-butyl (1S, 4S, 5R)-5-hydroxy-2-azabicyclo[2.2.1] heptane-2-formate (0.15 g, 0.7 mmol), potassium tert-butoxide (118 mg, 1.05 mmol) and 18-crown-6 (93 mg, 0.35 mmol) were dissolved into THF (20 mL), and the mixture solution reacted at 25° C. for 5 mins. 4-(bromomethyl)-5-cyclopropyl-3-(2-(trifluoromethoxy)phenyl)isoxazole (280 mg, 0.77 mmol) was then added, and the resulted solution reacted at 25° C. for 3 hrs. The reaction solution was concentrated, and purified by silica-gel column chromatography (petroleum ether:ethyl acetate=10:1) to obtain the product (200 mg, yield: 57.7%).

10. Preparation of 4-(((((1S, 4S, 5R)-2-azabicyclo[2.2.1]heptan-5-yl)oxy)methyl)-5-cyclopropyl-3-(2-(trifluoromethoxy)phenyl)isoxazole trifluoroacetate

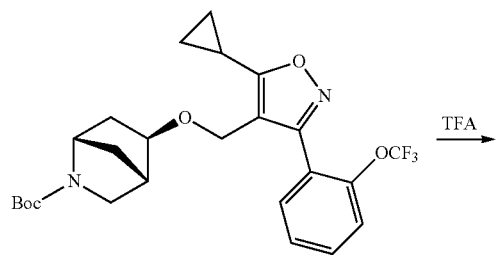

Tert-butyl (1S, 4S, 5R)-5-((5-cyclopropyl-3-(2-(trifluoromethoxy)phenyl) isoxazol-4-yl)methoxy)-2-azabicyclo[2.2.1]heptane-2-formate (0.2 g, 0.4 mmol) was added to DCM (10 mL), and TFA (4 mL) was added. The mixture solution reacted at 25° C. for 2 hrs, and the reaction solution was concentrated to obtain the crude product (300 mg).

11. Preparation of methyl 2-((1S, 4S, 5R)-5-((5-cyclopropyl-3-(2-(trifluoromethoxy) phenyl)isoxazol-4-yl)methoxy)-2-azabicyclo[2.2.1]heptan-2-yl)-4-fluorobenzo[d]thiazole-6-formate

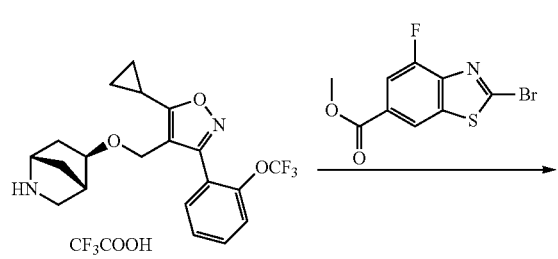

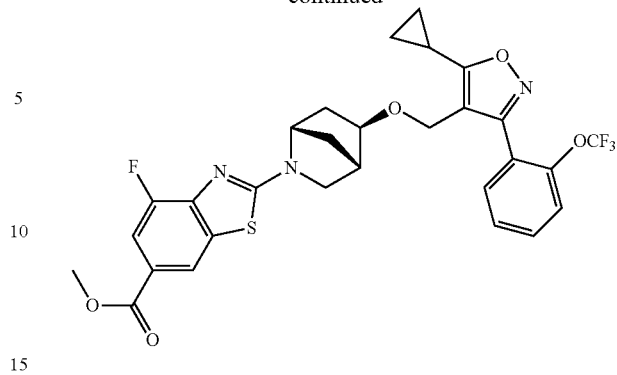

4-(((((1S,4S,5R)-2-azabicyclo[2.2.1]heptan-5-yl)oxy)methyl)-5-cyclopropyl-3-(2-(trifluoromethoxy)phenyl) isoxazole trifluoroacetate (300 mg, crude product), methyl 2-bromo-4-fluorobenzo[d]thiazole-6-formate (256 mg, 0.88 mmol) and cesium carbonate (600 mg, 1.84 mmol) were added to DMA (6 mL), and the mixture solution reacted at 110° C. under microwave for 0.5 hr. The reaction solution was poured into water (30 mL), and then filtrated. The filter cake was purified by silica-gel column chromatography (petroleum ether:ethyl acetate=2:1) to obtain the product (200 mg, two-step yield: 82.8%).

12. Preparation of 2-((1S, 4S, 5R)-5-((5-cyclopropyl-3-(2-(trifluoromethoxy)phenyl) isoxazol-4-yl)methoxy)-2-azabicyclo[2.2.1]heptan-2-yl)-4-fluorobenzo[d]thiazole-6-formic acid

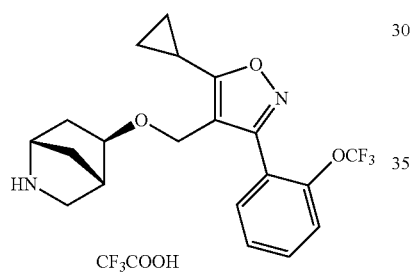

Methyl 2-((1S, 4S, 5R)-5-((5-cyclopropyl-3-(2-(trifluoromethoxy)phenyl)isoxazol-4-yl)methoxy)-2-azabicyclo[2.2.1]heptan-2-yl)-4-fluorobenzo[d]thiazole-6-formate (200 mg, 0.33 mmol) and lithium hydroxide monohydrate (70 mg, 1.65 mmol) were dissolved into the mixed solution of methanol (10 mL), tetrahydrofuran (10 mL) and water (10 mL), and the mixture solution was stirred at 25° C. for 4.6 hrs. The reaction solution was concentrated, and the pH of the water phase was adjusted to 2 with dilute hydrochloric acid (1 M), and then the water phase was extracted with ethyl acetate (50 mL×3). The organic phases were combined and concentrated, and the residue was purified by TLC (dichloromethane:methanol=10:1) to obtain the product (120 mg, yield: 61.7%).

Molecular formula: $C_{28}H_{23}F_4N_3O_5S$ Molecular weight: 589.56 LC-MS (M/e): 590.2 (M+H+)

$^1$H-NMR (400 MHz, CDCl$_3$) δ 8.09 (s, 1H), 7.72 (d, J=6.0 Hz, 1H), 7.52 (s, 2H), 7.35-7.38 (m, 2H), 4.29-4.35 (m, 2H), 3.59 (s, 1H), 3.49 (s, 1H), 3.00 (s, 1H), 2.63 (s, 1H), 2.07 (s, 2H), 1.69 (s, 2H), 1.47-1.50 (m, 1H), 1.21 (s, 2H), 1.10 (m, 2H).

What is claimed is:

1. A compound of general formula (II) a pharmaceutically acceptable salt thereof, an ester thereof or a stereoisomer:

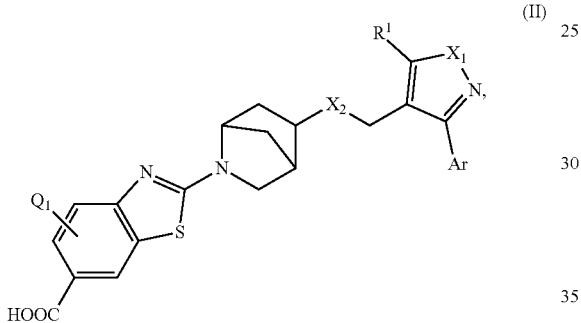

(II)

wherein $Q_1$ hydrogen;

$R^1$ is cyclopropyl;

$X_1$ and $X_2$ both are O;

Ar is phenyl optionally substituted by 1 to 2 $Q_2$; and each $Q_2$ is independently selected from chlorine and methoxy.

2. A compound, a pharmaceutically acceptable salt thereof, an ester thereof or a stereoisomer of the compound, the salt or the ester, wherein the compound is selected from:

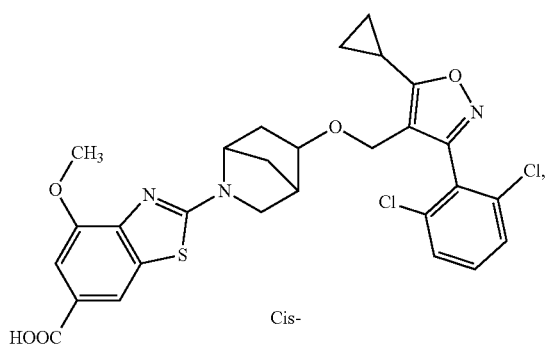

Cis-

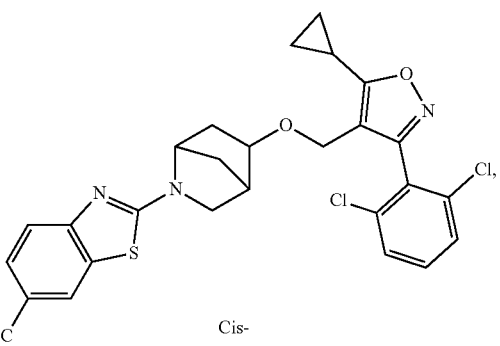

Cis-

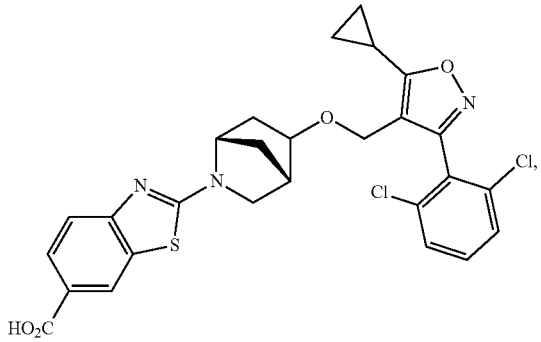

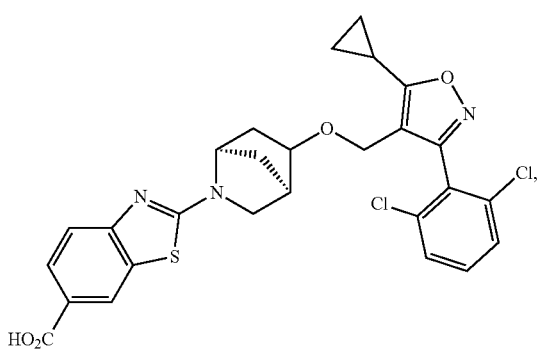

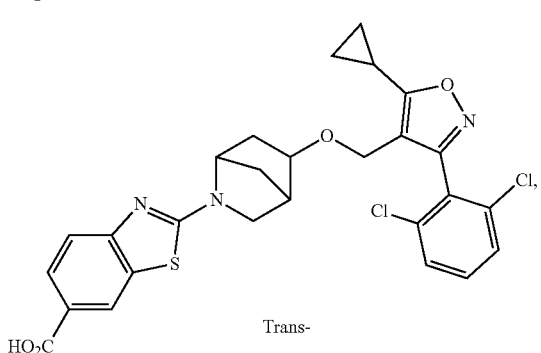

Trans-

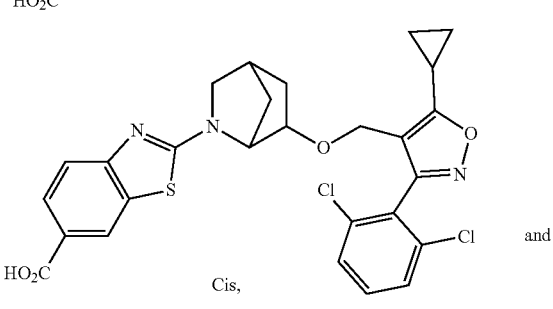

Cis, and

-continued

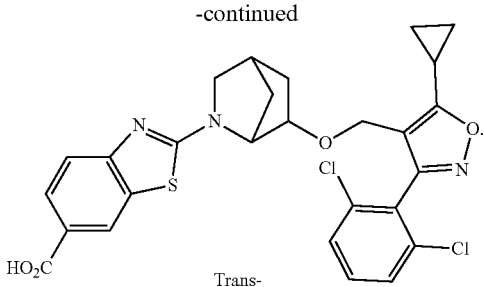

Trans-

3. A compound, a pharmaceutically acceptable salt thereof, an ester thereof or a stereoisomer of the compound, the salt or the ester thereof, wherein the compound is

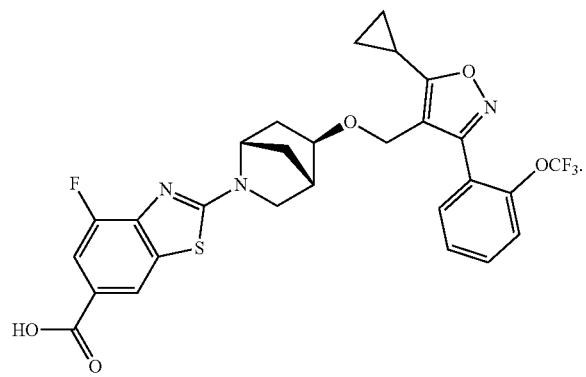 [SMILES: O=C(O)c1cc(F)c2nc(N3C[C@@H]4C[C@H]3C[C@H]4OCc3c(-c4ccccc4OC(F)(F)F)noc3C3CC3)sc2c1]

4. A pharmaceutical formulation containing the compound, a pharmaceutically acceptable salt thereof, an ester thereof or a stereoisomer of the compound, the salt or the ester of claim 1, wherein the pharmaceutical formulation contains one or more pharmaceutically acceptable carriers and/or diluents, and can be of any pharmaceutically acceptable dosage form.

5. A method for treating an FXR-mediated disease and related disease in a subject, wherein the method comprises administering to a subject in need thereof a therapeutically effective amount of the compound, a pharmaceutically acceptable salt thereof, an ester thereof or a stereoisomer of the compound, the salt or the ester of claim 1 or a pharmaceutical composition containing the compound, a pharmaceutically acceptable salt thereof, an ester thereof, or a stereoisomer of the compound, the salt or the ester of claim 1;

wherein the disease is selected from primary sclerosing cholangitis, fatty liver, cirrhosis, cholestasis, alcoholic steatohepatitis, primary biliary cirrhosis and nonalcoholic steatohepatitis.

6. The method of claim 5, wherein the diseases are selected from alcoholic fatty liver disease and nonalcoholic fatty liver disease.

\* \* \* \* \*